US011234860B2

(12) United States Patent
Scott et al.

(10) Patent No.: US 11,234,860 B2
(45) Date of Patent: Feb. 1, 2022

(54) MULTI-SECTIONAL PATIENT WARMING BLANKET

(71) Applicant: 3M INNOVATIVE PROPERTIES COMPANY, Saint Paul, MN (US)

(72) Inventors: Mark J. Scott, Maple Grove, MN (US); Jeffrey O. Emslander, Grant, MN (US); Andrew J. McGregor, Minneapolis, MN (US); Glenn R. Maharaj, Minneapolis, MN (US); Patrick J. Hager, Woodbury, MN (US); Melanie L. Collins, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/342,998

(22) PCT Filed: Oct. 18, 2017

(86) PCT No.: PCT/US2017/057082
§ 371 (c)(1),
(2) Date: Apr. 18, 2019

(87) PCT Pub. No.: WO2018/075576
PCT Pub. Date: Apr. 26, 2018

(65) Prior Publication Data
US 2019/0240067 A1    Aug. 8, 2019

Related U.S. Application Data

(60) Provisional application No. 62/504,657, filed on May 11, 2017, provisional application No. 62/411,112, filed on Oct. 21, 2016.

(51) Int. Cl.
*A61F 7/02* (2006.01)
*A61F 7/00* (2006.01)
(Continued)

(52) U.S. Cl.
CPC .......... *A61F 7/0097* (2013.01); *A47G 9/0215* (2013.01); *A61F 7/00* (2013.01);
(Continued)

(58) Field of Classification Search
CPC ...... A61F 2007/0034; A61F 2007/0036; A61F 2007/0039; A61F 2007/0045;
(Continued)

(56) References Cited

U.S. PATENT DOCUMENTS 5,097,548 A * 3/1992 Heck .................... A47G 9/0215
5/482
5,350,417 A * 9/1994 Augustine ............ A47G 9/0215
607/104

(Continued)

FOREIGN PATENT DOCUMENTS

WO    WO 95/35077     12/1995
WO    WO 97/14379     4/1997
(Continued)

OTHER PUBLICATIONS

PCT International Search Report for PCT/US2017/057082 dated Jan. 18, 2018.
(Continued)

*Primary Examiner* — Kaitlyn E Smith
*Assistant Examiner* — Yasamin Ekrami
(74) *Attorney, Agent, or Firm* — Jonathan V. Sry; Erik M. Drange

(57) ABSTRACT

Disclosed herein is a sectional warming blanket for patient warming having a structure comprising a first layer of material forming a bottom layer with openings to allow a profusion of air through the bottom layer, a second layer of material forming an upper layer wherein the upper layer is coupled to the bottom layer via a plurality of seals to form a plurality of interconnected air passageways, and an inlet
(Continued)

located on the upper or bottom layers. In an embodiment, the sectional warming blanket further comprises an opening configured to receive a coupling device for coupling the sectional warming blanket to an additional sectional warming blanket. In another embodiment, the sectional warming blanket further comprises at least one outline formed from a portion of the structure, such that a section can be removed from the blanket and the blanket is re-sealed by a bonding mechanism along its periphery.

13 Claims, 25 Drawing Sheets

(51) Int. Cl.
*A47G 9/02* (2006.01)
*A61F 7/08* (2006.01)

(52) U.S. Cl.
CPC .................. *A61F 7/08* (2013.01); *A61F 7/02* (2013.01); *A61F 2007/006* (2013.01); *A61F 2007/0244* (2013.01)

(58) Field of Classification Search
CPC ...... A61F 2007/0054; A61F 2007/0059; A61F 2007/0236; A61F 2007/0257; A61F 2007/0258; A61F 2007/0269; A61F 2007/0276; A61F 2007/0295; A61F 7/03; A61F 7/034; A47G 9/0215; A61B 46/00; A61B 2046/205; A61B 90/50; A41D 13/1236; A41D 13/0051; A41D 13/1245; A61H 2201/0242; A61H 9/0092; A61H 1/008; A61H 2201/0103; A61H 2201/0192; A61H 2201/0207; A61H 2201/0214; A61H 2201/50; A61H 2205/02; A61H 2205/04; A61H 2205/06; A61H 2205/08; A61H 2205/10; A61H 2205/102; A61H 2205/12; A61H 9/005
See application file for complete search history.

(56) References Cited

U.S. PATENT DOCUMENTS

| | | |
|---|---|---|
| 5,443,488 A | 8/1995 | Namenye |
| 5,545,194 A | 8/1996 | Augustine |
| 5,735,890 A | 4/1998 | Kappel |
| 5,773,275 A * | 6/1998 | Anderson ............. A61F 7/0097 435/197 |
| 5,824,025 A | 10/1998 | Augustine |
| 5,964,792 A | 10/1999 | Augustine |
| 7,520,889 B2 | 4/2009 | Van Duren |
| 2003/0135251 A1 | 7/2003 | Schuessler |
| 2007/0073368 A1 | 3/2007 | Cazzini |
| 2010/0161012 A1 | 6/2010 | Van Liebergen |
| 2010/0211141 A1 | 8/2010 | Pierre |
| 2014/0277307 A1* | 9/2014 | Gammons ............. A61F 7/0097 607/107 |
| 2014/0316494 A1 | 10/2014 | Augustine |
| 2015/0196422 A1 | 7/2015 | Teunissen |

FOREIGN PATENT DOCUMENTS

| | | |
|---|---|---|
| WO | WO 99/08631 | 2/1999 |
| WO | WO 2010/093458 | 8/2010 |
| WO | WO 2010/096161 | 8/2010 |
| WO | WO 2016/069551 | 5/2016 |
| WO | WO 2016/105462 | 6/2016 |
| WO | WO 2018/075575 | 4/2018 |
| WO | WO 2018/075579 | 4/2018 |

OTHER PUBLICATIONS

PCT International Search Report for PCT/US2017/057079 dated Apr. 7, 2018.
Covidien AG. © 2013 Covdien. "*WarmTouch™ Convective Warming System*" brouchure.
Tyco Healthcare UK Ltd. © 2007 Nellcor Puritan Bennett LLC. "*WarmTouch® Convective Air Warming System*" brochure.
PCT International Search Report for PCT/US2017/057085 dated Jan. 18, 2018.

\* cited by examiner

A-A

MULTI-SECTIONAL PATIENT WARMING BLANKET

CROSS REFERENCE TO RELATED APPLICATIONS

This application is a national stage filing under 35 U.S.C. 371 of PCT/US2017/157082, filed Oct. 18, 2017, which claims the benefit of both U.S. Provisional Application No. 62/411,112, filed Oct. 21, 2016 and U.S. Provisional Application, filed May 11, 2017, the disclosures of which are incorporated by reference in their entirety herein.

TECHNICAL FIELD

The disclosure relates to patient warming blankets or pads.

BACKGROUND

Patients who are preparing for, undergoing and recovering from a surgical procedure often require and are under the influence of anesthesia as part of the procedure. Due to the effects of the anesthesia, a patient may become unable to regulate their own core body temperature, a condition known as poikilothermia. Under these conditions, and when for example in an air-conditioned environment such as an operating room or a recovery area in a hospital or in a clinic, the lower air temperature and the need for the patient to be at least partially undressed may lead to the patient becoming hypothermic, wherein the core body temperature of the patient may begin to drop in an unintentional and undesirable manner.

One technique used to prevent hypothermia or other undesirable losses in body temperature of a patient when under the influence of an anesthetic is by the use of a forced air warming blanket or pad. The blankets or pads are generally constructed of a series of air passages and interconnected airways formed between two layers of material. The first layer of material is generally non-porous, and is formed on one side of the blanket or pad, and a second layer that is porous, or that includes distributed air-holes (e.g., perforations), is bonded in some fashion to the first layer of material to form the air passages and/or airways. The blanket or pad is configured to be coupled to a device that warms a flow of air to a predefined temperature range, and then directs that warmed air, using a relatively low pressure, into the air passages and/or airways, often through a flexible tube or duct that may also be formed of a non-porous material. The warm air provided into the air passages and/or airways is expelled at a slow rate though the porous material or out through the distributed air-holes provided by the second layer of material due to the low level of air pressure generated between the first and second layers of material.

By placing the blanket or pad for example over, underneath or in proximity to at least some portion or portions of the patient, the warmed air may be directed to the patient in a manner that assists the body of the patient in maintaining an acceptable core body temperature. Contact with the blanket or pad itself by a portion or portions of the body of the patient may also help assist the body in maintaining the core body temperate within acceptable limits.

SUMMARY

In general, systems, devices, and techniques are described herein allowing a disposable multi-sectional warming blanket to be configured for a variety of patient warming and/or cooling applications. In some examples, the multi-sectional blanket is configured to include a plurality of individual sectional warming blankets, each sectional warming blanket comprising at least a first air inlet and at least one air outlet (opening) configured to allow the air outlet to be coupled to an air inlet of another sectional warming blanket. In various examples, a sectional warming blanket may be configured to be couple to a plurality of additional sectional warming blankets. The coupling of a plurality of sectional warming blankets may be accomplished by coupling the sectional warming blankets is a series configuration, or in multiple-branching configurations, such as a parallel or a "Y" shaped configuration, as star shaped configuration, or a circular configuration, and any combination thereof.

Various examples described in the present disclosure are directed to a sectional warming blanket for patient warming, the sectional warming blanket comprising: a structure comprising a first layer of material and a second layer of material, the first layer of material forming a bottom layer of the warming blanket, the bottom layer configured to allow a profusion of air to pass through the bottom layer, and the second layer of material forming an upper layer of the warming blanket, the upper layer coupled to the bottom layer around a periphery of the bottom layer to form an initial shape of the warming blanket and to form an interior space between the first layer of material and the second layer of material comprising a plurality of interconnected air passageways, wherein the passageways are defined by a plurality of seals formed between the upper layer and the bottom layer within the area defined by the periphery; an inlet located on the upper layer or the bottom layer, the inlet comprising an inlet passageway configured to receive a flow of air from a source and to provide the flow of air to the interconnected air passageways; and an opening located on the upper layer or the bottom layer, the opening comprising a removable seal configured to seal an opening passageway coupled to the interconnected air passageways, the removable seal configured to maintain an air seal when in place over the opening passageway.

Other examples described in the present disclosure are directed to a multi-sectional warming blanket system, the system comprising a plurality of sectional warming blankets coupled together through one or more air flow couplings and arranged into a predetermined arrangement, the predetermined arrangement specific to a designated patient position in patient treatment procedure; and a source of a flow of air coupled to at least one of the plurality of sectional warming blankets, the source configured to deliver a flow of air to the multi-sectional warming blanket at a rate of flow adequate to inflate each of the plurality of sectional warming blankets; wherein each of the sectional warming blankets comprises a structure comprising a first layer of material and a second layer of material, the first layer of material forming a bottom layer of the warming blanket, the bottom layer configured to allow a profusion of air to pass through the bottom layer, and the second layer of material forming an upper layer of the warming blanket, the upper layer coupled to the bottom layer around a periphery of the bottom layer to form an initial shape of the warming blanket and to form an interior space between the first layer of material and the second layer of material comprising a plurality of interconnected air passageways, wherein the passageways are defined by a plurality of seals formed between the upper layer and the bottom layer within the area defined by the periphery, and an inlet located on the upper layer or the bottom layer, the inlet comprising an inlet passageway configured to receive a flow of air from a source and to provide the flow of air to the interconnected air passageways; and an opening located on the upper layer or the bottom layer, the opening comprising a removable seal configured to seal an opening passageway coupled to the interconnected air passageways, the removable seal configured to maintain an air seal when in place over the opening passageway.

Other examples described in the present disclosure are directed to A method of forming a multi-sectional warming blanket, the method comprising: configuring a plurality of sectional warming blankets into a predetermined arrangement, the predetermined arrangement, the predetermined arrangement specific to a designated patient position in patient treatment procedure; forming an air flow coupling between at least two of the plurality of sectional warming blankets to form a multi-sectional warming blanket; and providing a flow of air to at least one of the plurality of sectional warming blankets to inflate each of the sectional warming blankets included in the multi-sectional warming blanket.

Additional examples described in the present disclosure are directed to a method comprising: A method comprising: forming a plurality of sectional warming blankets along a length of web material, each of the sectional warming blankets comprising a bottom layer configured to provide a profusion of air through the bottom layer; forming a set of cutlines, each cutline provided across a width dimension of the web material and located between two of the warming blankets along a longitudinal dimension of the web material; and folding the web material including the sectional warming blankets along the set of cutlines form a stack of sectional warming blankets coupled at the cutlines, each of the sectional warming blankets comprising an inlet located on an upper layer couple to the bottom layer, the inlet comprising an inlet passageway configured to receive a flow of air from a source and to provide the flow of air to an interconnected air passageway located between the upper layer and the bottom layer; and each of the sectional warming blankets further comprising an opening located on the bottom layer, the opening comprising a removable seal configured to seal an opening passageway coupled to the interconnected air passageways, the removable seal configured to maintain an air seal when in place over the opening passageway and to be removed to allow the opening to be coupled to an additional sectional warming blanket to form a multi-sectional warming blanket.

Figure 1:
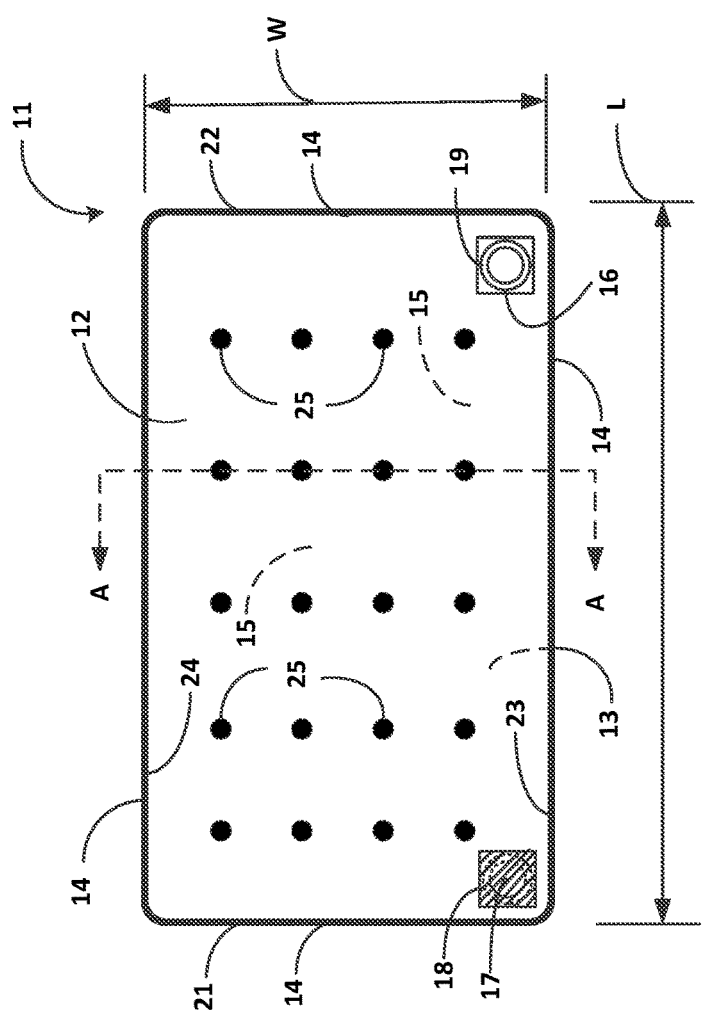
FIG. 1 illustrates a top view and a cutaway view of various dimensional aspects and other characteristics of an example sectional warming blanket 11 according to various techniques described in this disclosure.
Figure 1:
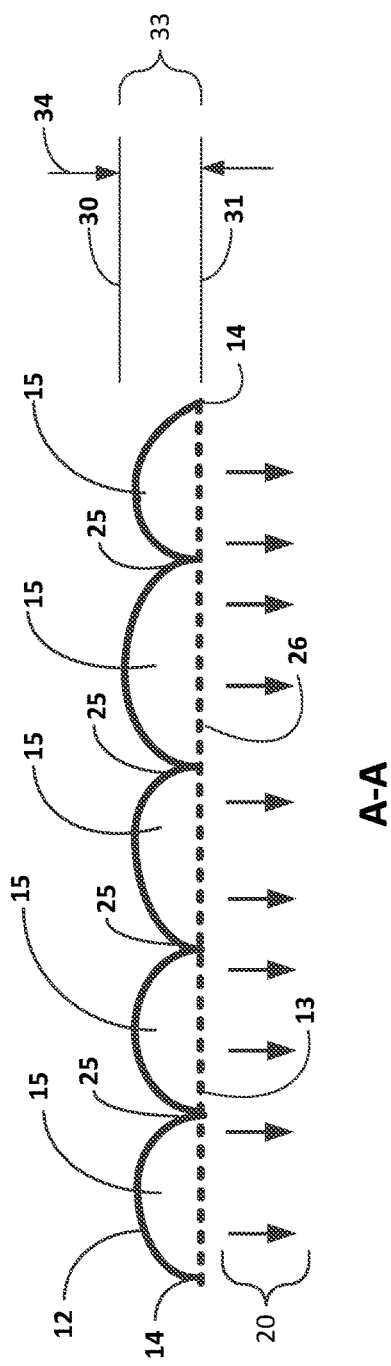

The drawings and the description provided herein illustrate and describe various examples of the inventive methods, devices, and systems of the present disclosure. However, the methods, devices, and systems of the present disclosure are not limited to the specific examples as illustrated and described herein, and other examples and variations of the methods, devices, and systems of the present disclosure, as would be understood by one of ordinary skill in the art, are contemplated as being within the scope of the present application. In addition, one or more reference numbers may be first introduced in a figure of the application to refer to a device, a method step, or some other aspect related to the figure, wherein the same reference number may then be used in a subsequent figure or figures to refer to the same device, method step, or other aspect as described with respect to the original figure, but without a particular reference to the same reference numbers in the description corresponding to the subsequent figure(s). In such instances and unless stated otherwise, the reference numbers as used in the subsequent figure or figures incorporate all of the features, functions, and the equivalents thereof of the devices, method steps, or other aspects described with respect to the reference number where first introduced and described.

DETAILED DESCRIPTION

In general, systems, devices, and techniques are described herein allowing a disposable multi-sectional warming blanket to be configured for a variety of patient warming applications. In some examples, the multi-sectional blanket is configured to include a plurality of individual sectional warming blankets, each sectional warming blanket comprising at least a first air inlet and at least one air outlet (opening) configured to allow the air outlet to be coupled to an air inlet of another sectional warming blanket. In various examples, a sectional warming blanket may be configured to be coupled to a plurality of additional sectional warming blankets. Although described in various examples as a patient warming blanket, depending on the temperature of the air provided to inflate the selection warming blanket or blankets, the examples described herein may also be utilized in patient cooling applications. For example, warm air may be provided to inflate a sectional warming blanket or a multi-sectional warming blanket for warming a patient, and in other examples or at certain times, ambient temperature or cooler air may be provide to the sectional warming blanket or multi-sectional warming blanket to cool a patient.

Once coupled together and provided with a source of air, the multi-sectional warming blanket may be placed adjacent to and/or covering certain portions of the body of the patient, the configuration of the multi-sectional warming blanket arranged to provide efficient warming of the patient or cooling of the patient, while also allowing access to portions of the patient, for example by personnel such as a physician or a medical profession, who is performing a procedure on the patient. The multi-sectional warming blanket is also configured to be reconfigurable, for example by adding or removing sections of the warming blanket, or by rearranging the positions and/or orientations of the sections of the warming blanket relative to each other. These features of the multi-sectional warming blanket, and additional features as described in this disclosure, provide flexibility in configuring a warming blanket for a particular patient and/or for a particular procedure being performed on the patient. For example, due to the different sizes of patients, e.g., the size of a child patient versus an adult patient, and/or because of the variations in the positions a patient may need to be placed into according to the specific procedure being performed on the patient, many different sizes, shapes and configurations of warming blankets have been developed.

However, the variations in needs related to different sizes and configurations of patients often leads to a need for an institution, such as a hospital or a clinic that performs various procedures, to stock a variety of different configurations of warming blankets and pads. In addition, depending on the particular procedures being performed on the patient, a warming blanket or pad may not exist that adequately covers the patient and provides warming without undue interference with the procedure. Further, a particular procedure may require work to be done first on one portion of the patient, while other portions of the patient may require use of the warming blanket or pad having a first configuration or shape, and the one or more later parts of the procedure may require access to different portions of the patient, wherein the warming blanket would need to be moved or otherwise reconfigured. With conventional warming blankets, the particular configuration of the warming blanket used during the first portion of this illustrative example procedure may not be configurable for use during the second or later portions of the procedure, thus requiring use of two or more separate warming blankets, adding to the cost of performing the overall procedure.

Systems, devices, and techniques described in this disclosure provide examples of patient warming blankets that may be arranged in a wide variety of configurations using a same type, or a limited number of types of building block sectional warming blankets. The ability to provide a wide variety of configurations for patient warming blankets based on a single type of sectional warming blankets, or with a limited number of types of sectional warming blankets, may allow the institution using the warming blankets to reduce the total number of different types and sizes of warming blankets the institution needs to stock, thus reducing cost and simplifying inventory control procedures. Further, that ability to reconfigure the arrangement of the multi-sectional warming blanket, including the ability to reconfigure the arrangement of the multi-sectional warming blanket at various stages of a procedure being performed on the patient while the warming blanket is in use may provide an added level of convenience, cost savings, and efficiency in warming the patient that may not be provided when using convention warming blankets, for examples with blankets comprising just one piece or one section as the convective portions of the warming blanket.

Although examples of the systems, devices and techniques described throughout this disclosure refer to forced air warming blankets, these systems, devices, and techniques are not necessarily limited to forced air warming blankets, and may be equally applicable to warming pad, warming tubes, and other patient warming devices, and the equivalents thereof, as would be understood by one or ordinary skill in the art.

FIG. 1 illustrates a top view and a cutaway view of various dimensional aspects and other characteristics of an example sectional warming blanket 11 according to the techniques described in this disclosure. Sectional warming blanket 11 (hereinafter referred to as "warming blanket 11") comprises upper layer 12 comprising a first sheet of material, and a bottom layer 13 comprising a second sheet of material. In various examples, upper layer 12 is a separate sheet of material that is bonded to bottom layer 13 along a periphery 14 of each of the layers 12, 13. In other examples, upper layer 12 is a same sheet of material folded over bottom layer 13, or formed as a tube, and then bonded (sealed) along portions of the periphery 14, such as at the end 21 and the end 22, where the material is not already part of a continuous sheet. Upper layer 12 may also be bonded to bottom layer 13 at portions of the upper layer 12 not along periphery 14 to form seals 25 where upper layer 12 contacts bottom layer 13. The seals 25 form spaces between upper layer 12 and bottom layer 13 between the seals 25, the spaces forming a plurality of interconnected passageways, generally indicated as passageways 15, for a flow of air between layers 12 and 13. Seals 25 as shown in FIG. 1 illustrated staked seals, wherein the uppers layer 12 and bottom layer 13 are bonded at a generally circular shaped boding areas. However, seals 25 are not limited to staked types seals, and may include other forms of seals, such as seals formed along linear lines having a length dimension, such as seals 156 shown in FIG. 6A and a peripheral seal around periphery 14. In various examples, warming blanket 11 may include a combination of staked and linear seals.

As illustrated in FIG. 1. passageways 15 are coupled to an inlet 16 comprising an opening to the passageways 15 from outside the warming blanket 11, in some examples to receive a coupling (not shown in FIG. 1). In various examples, inlet 16 includes a rigid collar 19 surrounding the opening in inlet 16, and that engages and/or secures the coupling to inlet 16. The coupling that may be received at inlet 16, and also to be coupled to a tubular air hose (not shown in FIG. 1), the hose coupled to a source (not shown in FIG. 1), the source to generate a flow of air that is provided to warming blanket 11. The source may be any device that is configured to warm a flow of air to a temperature that may be applied to a patient (not shown in FIG. 1) safely while the patient is for example preparing for, undergoing, and/or recovering from a procedure where the patient may or may not be under the influence of an anesthetic. The warm air from the source is provided through a connective hose to inlet 16 at a relatively low pressure, for example a pressure less than 100 mm Hg, and flows through inlet 16, where the air flow continues into the passageways 15 of warming blanket 11, and inflating the warming blanket to fill the passageways 15 via the low pressure air flow provided to inlet 16. Throughout the disclosure reference to a flow of warmed are may include a flow of air at various temperatures, including a flow of air provided at an ambient temperature, and is not limited to a flow of air provided at any particular temperature or within any particular range of temperatures.

Each of the upper layer 12 and the bottom layer 13 may include one or more sheets, where each sheet may be formed from a different material. In some implementations, the upper layer 12 and/or the bottom layer 13 may include an underside sheet formed from a flexible, fibrous, preferably non-woven structure composed of polymeric materials capable of bonding to an upper side sheet of a heat-sealable polymeric material. For example, the underside sheet may be a non-woven, hydroentangled polyester material and the upper side layer may include a polyolefin such as a polypropylene film which is extrusion-coated, thermally laminated, or adhesively laminated onto the polyester layer. Alternatively, the underside sheet may comprise a non-woven, paper-based material to which the upper side layer, including either a polyethylene or polypropylene film, has been glue laminated. In one embodiment, the upper side and underside sheets can be made with a stratum of absorbent tissue paper prelaminated with a layer of heat-sealable plastic. In some cases, both the first layer and the second layer can include a same polymer material.

In some embodiments, the bottom layer 13 includes the upper side sheet and the underside sheet, and the upper layer 12 comprises the same material as the upper side sheet of the second layer. The upper layer 13 thus may include a sheet of plastic bonded to the plastic upper side of the second layer. It is preferably attached by a continuously-running web process including stations that provide an interruptible heat-sealing process. This interruptible heat sealing process can be controlled to form the stake seals 25 and/or elongated linear heat seals that define the inflatable channels therebetween. The seals can be formed as continuous air impervious seals or discontinuous air permeable seals. The interruptible heat sealing process can be used to form the continuous seams, one of which is the seam at the peripheral of the second layer and the first layer. In some cases, the interruptible heat sealing process can be used to form the discontinuous heat seals. In some cases, absorbent material can be applied to the convective device, for example, applied as a single material layer. The absorbent material can be bonded to the upper plastic layer by heat processing or by adhesive bonding.

In some embodiments, the warming blanket 11 is enabled to bathe a patient in the thermally controlled inflation medium introduced into the warming blanket 11 when inflated, via an air permeable layer, the first layer and/or the second layer. A layer can be air permeable using various materials or mechanical structures, for example, air-permeable materials, apertures, interstices, slits, or the like. In some implementations of an air permeable sheet with apertures, the density of apertures can vary among areas and/or inflatable sections.

In some embodiments, the upper layer 12 and/or the bottom layer 13 are made from a polyolefin non-woven extrusion coated, each with a coating of polypropylene on one side. In some other embodiments, the upper layer 12 and/or the bottom layer 13 can be poly lactic acid spunbond with polyolefin based extrusion coat. One of the upper layer 12 and bottom layer 13 may have holes formed by punching, slitting, or cutting to permit the flow of pressurized inflation medium from the inflated section through the layer. In some cases, the holes can be opened through both layers. In some cases, when the warming blanket 11 is assembled, the polypropylene-coated side of the upper layer 12 is sealed to the polypropylene-coated side of the bottom layer at the periphery 14, and at the one or more locations such as seals 25 to form the construction. The sealing process can use various techniques, for example, ultrasonic welding, radio frequency welding, heat sealing, or the like. Alternatively, the upper layer 12 and bottom layer 13 may each include a laminate of polypropylene and polyolefin web with holes formed in at least one of the layers to support passage of pressurized air. In yet another embodiment, at least one of the layers can use air permeable material, for example, spunbond-meltblown-spunbond (SMS) nonwoven material, or the like.

Upper layer 12 of the warming blanket 11 is some examples comprises a material that is non-porous, and thus does not provide a path for air to flow from passageways 15 through the upper layer 12 to areas outside the warming blanket 11. The non-porous characteristics of the upper layer 12 may help maintain a low level of air pressure within the passageways 15 based on the air flow and air pressure provided to inlet 16. In these examples, bottom layer 13 is porous, either by virtue of being formed from a porous material, such as a woven or nonwoven material, or by being formed from a non-porous material that has been further processed to include a plurality of perforations (e.g., through-holes in bottom layer 13, not specifically shown in FIG. 1) that allow air to flow from passageways 15 to an area outside the warming blanket, the airflow generally indicated by arrows 20 in FIG. 1. This airflow, and/or by virtue of contact with bottom layer 13, provides the warming to a patient when warming blanket 11 is placed in proximity to the patient and is receiving a flow of warmed air at inlet 16. However, in some examples both upper layer 12 and bottom layer 13 are porous and provide a flow of air from passageways 15 through each layer and to an area or areas outside the warming blanket 11.

In instances were bottom layer 13 is a porous material, the air flow generally indicated by arrow 20 will be distributed across most of the surface area comprising the bottom surface 13, wherein the porosity and the surface area of bottom layer 13 are configured to allow enough backpressure for inflation of passageways 15, and thus to provide a gentle and warming air flow when a source is providing an air flow to inlet 16 within a predetermined range of pressures and rates of air flow. In instances were bottom layer 13 is a non-porous material but has been further processed to include perforations (e.g., through-holes) extending through the material forming the bottom layer 13, the perforations may be sized and distributed over the surface areas of the bottom layer 13. The sizing and distributing of the perforations is configured to allow the air flow, generally indicated by arrows 20, to be provided across substantially most of surface area comprising the bottom layer 13, while providing enough backpressure and to allow for inflation of passageways 15, and thus to provide a gentle and warming air flow (e.g., arrows 20) when a source is providing the air flow to inlet 16 within a predetermined range of pressures and rates of air flow.

Warming blanket 11 may also include one or more additional opening, illustratively shown as opening 17 in FIG. 1. As shown, opening 17 is located on upper layer 12, and provides a passage from outside warming blanket 11 through opening 17 to passageways 15. Opening 17 may be configured to receive a coupling device, such as a hose or a coupling (neither shown in FIG. 1), that allows air flow from passageways 15 to exit warming blanket 11 through opening 17 and flow on to another sectional warming blanket (not shown in FIG. 1). Using opening 17 to couple air flow from passageways 15 of warming blanket 11 to another sectional warming blanket allows multi-sectional warming blankets to be coupled together to form various configurations of sectional warming blankets, which may also be inflated and provided a flow of warmed air from a common source of air flow, for example the air flow provided to inlet 16. In addition, instead of inlet 16 being coupled directly to an air source, inlet 16 of warming blanket 11 may to couple to another sectional warming blanket, for example through an opening similar to opening 17, and receive an air flow at inlet 16 from this other section warming blanket. In some examples, opening 17 is located on the bottom layer 13 of warming blanket 11 and is configured to be overlapped with another sectional warming blanket so that opening 17 of warming blanket 11 aligns with and can be coupled to an inlet, similar to inlet 16, of the other warming blanket. In various examples, the type of coupling used between warming blanket 11 and another sectional warming blanket comprises a rotationally sealing mechanism or technique that allows for rotational orientation between the relative positions of the coupled warming blankets, for example relative to each of the longitudinal axes of the warming blankets, so that when coupled the angle and overlap between the two coupled warming blankets may adjusted to a variety to angles relative to one another.

Examples of warming blanket 11 are not limit to having a single additional opening 17, and may comprise one or more openings on the upper layer 12, one or more openings on the bottom layer 13, or one or more opening on both the upper layer 12 and the bottom layer 13. In various examples, the passage through opening 17 includes a layer of material, such as the layer of material used to form either the upper layer 12 or the bottom layer 13 where the opening 17 is located. The material seals opening 17 relative to air flows through the passage when the material is in place in the passage. In these examples the material may provide a weakened or perforated pattern that allow the material to be opened, for example by pushing through or otherwise breaking through the material, for example by tearing the material along the weakened or perforated pattern, and to at least partially open the passage though opening 17 to allow air to flow through the opening formed in the passage. In various examples, warming blanket 11 is initially provided with a removable seal 18 covering and sealing the opening 17. For example, when originally packaged, warming blanket 11 may have a removable seal 18 provided over opening 17 so that a source of a flow of air may be directly coupled to inlet 16 of the warming blanket, and warming blanket can be used alone in a patient warming configuration without being coupled to any other sectional warming blanket. In this example, the seal 18 would simply remain in place sealing opening 17. In other examples warming blanket 11 receives a flow of warmed air at inlet 16 from another sectional warming blanket, but is not further coupled to any additional sectional warming blankets. In such examples, again seal 18 may be left in place over opening 17 in order to allow warming blanket 11 to be properly pressured by the air flow received at inlet 16. In still other example, warming blanket 11 is coupled, either directly or through another sectional warming blanket, to a source providing a flow of warmed air, and also is to provide the air from for one or more additional sectional blankets. In these examples, seal 18 may be removed from opening 17 in order to allow opening 17 to be coupled to another sectional warming blanket. It would be understood by one of ordinary skill in the art that additional openings, if provided with warming blanket 11 may also be sealed in any of the manners described herein and the equivalents thereof for sealing opening in a warming blanket.

The sealing of an opening in a sectional warming blanket is not limited to any particular device or method of sealing the opening. In various examples, a layer of film formed of plastic or formed of a paper product may be affixed to a housing plate surrounding opening 17 by a semi-permanent adhesive, such as adhesives described below. The adhesive may allow the film to be held in place to seal opening 17 again the air pressures provided in passageways 15 of warming blanket 11, and may also be peeled off or otherwise removed to allow access to opening 17, for example to insert a coupling device into opening 17. In some examples, the semi-permanent adhesive is a selective adhesive that only strongly adheres to itself, or to some other particular types of materials. In these examples, two openings 17 in different warming blankets both having the selective adhesive applied to the openings can be coupled together by bringing the selective adhesives on each opening into contact. Examples of selective adhesives include those described in U.S. Pat. No. 6,531,021 and incorporated here by reference. In some examples, the semi-permeant adhesive allows the openings to be initially coupled in a first coupled position, and then separated and recoupled, again by the semi-permeant adhesive, in a second coupled positon that is different from the first coupled position. This capability provides the useful feature of being able to reposition and/or reorient of the warming blankets relative to one another for examples during different stages of a procedure being performed on a patient while using the warming blankets to warm the patient.

In other examples, seal 18 may include a threaded portion that engaged a corresponding threaded portion of opening 17, and may be configured to seal opening 17 when screwed in place in the opening, and can be unscrewed to remove seal 18 and allow access to opening 17. Other method and techniques for removably sealing opening 17 would be understood by one of ordinary skill in the art, and are contemplated for use as a removable seal for opening 17 as part of this disclosure.

FIG. 1 includes a cutaway view A-A showing a view of warming blanket 11 looking into the central portion of the warming blanket in a direction towards end 21. As shown in view A-A, upper layer 12 is sealed or otherwise in contact and bonded with bottom layer 13 at the periphery 14, and also at seals 25, to form passageways 15 between upper layer 12 and bottom layer 13. Bottom layer 13 comprises a porous material, or may be a perforated non-porous material, having passages or through-holes, generally indicated as perforations 26, that allow a flow of air, generally indicated by arrows 20, to exit passageways 15 through bottom layer 13 when warming blanket 11 is provided a flow of air to passageways 15. Bottom layer 13 is generally a sheet of material having a planar configuration within periphery 14, generally coplanar with plane 31, and upper layer 12 is generally a sheet of material, having ridges formed by seals 25 and passageways 15, but generally having peaks falling with a planar area indicated by plane 30. However, bottom layer 13 is not limited to having a substantially flat planar configuration, and may have some variations, for examples created by seals 25, in a similar manner described for upper layer 12. The upper layer 12 and the bottom layer 13 are generally contained within an area between planes 30 and 31, generally indicated by area 33, and having a thickness dimension 34. In various examples of warming blanket 11, thickness dimension 34 comprises a thickness value having a range between 3 and 15 inches.

Referring back to the top view in FIG. 1, warming blanket 11 is illustrated has having a generally rectangular shape defined by periphery 14. Warming blanket 11 has a longitudinal dimension L running parallel to a longitudinal axis of the warming blanket, and a width dimension W that is perpendicular to the longitudinal axis and the longitudinal dimension L. The longitudinal and width dimensions of warming blanket 11 are not limited to any particular dimensions. In some examples, the value of the longitudinal dimension L may be in a range of 18 to 50 inches. In some examples the value of the width dimension W may in a range of 10 to 36 inches. However, dimensions other than these dimensions may be provided in a warming blanket 11, and are contemplated by the examples of warming blankets as described herein. In addition, the shape of the warming blanket 11 is not limited to being a rectangular shape, and may comprise other shapes based on the periphery 14, such as a square shape, a round shape, or some any other enclosed polygonal shape. These and other shapes are contemplated as shapes for warming blankets according the examples described in this disclosure.

In use, once inflated with the proper flow of warmed air, warming blanket 11 may be placed over a patient (not shown in FIG. 1) and proximate to portions of the body of the patient, so that the bottom layer 13 is facing the portions of the patient that are to be warmed. For example, warming blanket 11 may be place over the upper torso and arms of a patient, for example during times when direct or immediate access to these portions of the patient are not required by other personnel, such as a physician or a surgeon. In other examples, the warming blanket may be detachably made as part of a gown (not shown in FIG. 1) that may be worn by the patient while waiting for the process that is to be performed on the patient to begin. In such instances, the detachable warming blanket may be detached from the gown when the gown is fully or partially removed from the patient in preparation for the actual procedure, and the warming blanket repositioned proximate to the patient to provide patient warming. Once in place, the air flow from the warming blanket 11 (generally indicated by arrows 20) may be directed to the portions of the patient proximate to the warming blanket, and thus provide a gentle and warming air flow and or a warm surface provided by the external surface of bottom layer 13 that warms the patient.

However, a single blanket 11 having a particular shape may not be effective in providing warming for a patient when the patient is required to be in some particular position, or for example when the patient may need to be positioned in various different positions over the course of a procedure. As discussed above, this may require for example a hospital or a clinic to stock a variety of different warming blankets that may be required for different procedures, thus adding to inventory costs. In addition, certain procedures may require multiple different patient positions that may not be accommodated by use of a single conventional warming blanking having for example a relatively fixed initial configuration and shape when inflated. The systems, devices, and techniques described in this disclosure allow sectional warming blankets to be coupled together in various configurations to form multi-sectional warming blankets. The multi-sectional warming blanket may be arranged and in some instances rearranged either before, during and/or following a procedure performed on a patient to provide a flexible and cost efficient patient warming system. Examples of these systems, devices, and techniques are further described below as part of this disclosure.

Figure 2:
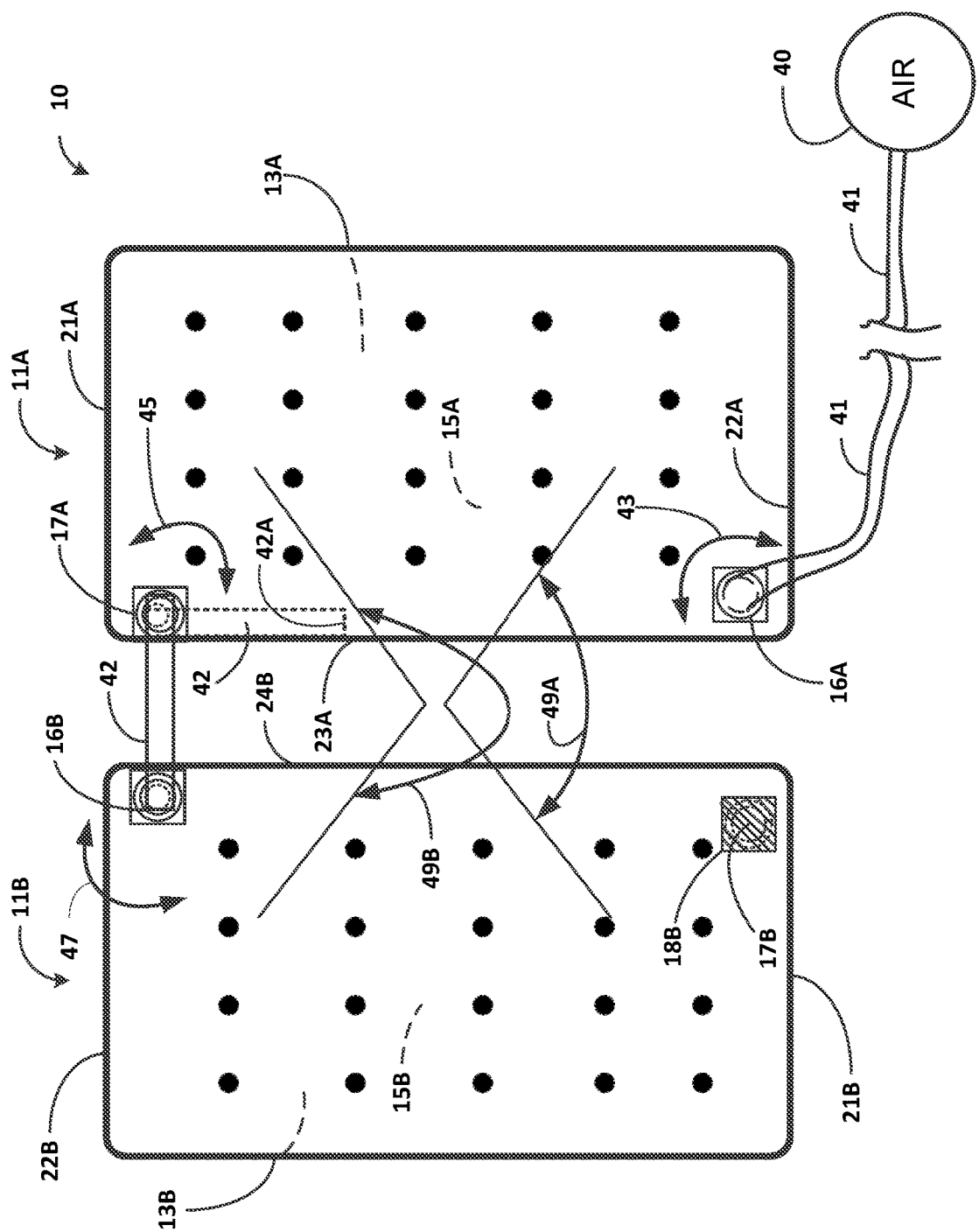
FIG. 2 illustrates a top view of an example patient warming system according to various techniques described in this disclosure.

FIG. 2 illustrates a top view of an example patient warming system 10 according to the techniques described in this disclosure. As illustrated, system 10 comprises a first sectional warming blanket 11A (hereinafter referred to as "warming blanket 11A"), and a second sectional warming blanket 11B (hereinafter referred to as "warming blanket 11B"). Warming blankets 11A and 11B are not limited to any particular type of sectional warming blankets, and may include any of the examples of the sectional warming blanket 11 illustrated and described with respect to FIG. 1.

As illustrated in FIG. 2, system 10 further includes an air source 40 (hereinafter referred to as 'source 40"). Source 40 is not limited to any particular type or configuration of a source of a flow of air, and may be a source configured to provide a flow of air that has been warmed to within a range of temperatures and provided at a flow rate that is within a proper range to be provided to warming blankets 11A and 11B for the purpose of providing patient warming are located in proximity to a patient. In various examples, warming blankets 11A and 11B are a same type and a same size sectional warming blanket, although examples of system 10 may also include having warming blanket 11A and warming blanket 11B including different types and/or different sizes of sectional warming blankets.

As illustrated in FIG. 2, warming blanket 11A includes an inlet 16A located near a first end 22A of warming blanket 11A, and an opening 17A located near an opposite end 21A of warming blanket 11A. Similarly, warming blanket 11B includes an inlet 16B located near a first end 22B of warming blanket 11B, and an opening 17B located near an opposite end 21B of warming blanket 11A. As shown for system 10, inlet 16A and opening 17A of warming blanket 11A are located near a side 23A of the warming blanket, and inlet 16B and opening 17B of warming blanket 11B are located near a side 24B of warming blanket 11B. Warming blanket 11B is positioned so that side 24B is located adjacent to side 23A of warming blanket 11A, and substantially co-planar to warming blanket 11A, thus providing inlet 16B of warming blanket 11B in close proximity to opening 17A of warming blanket 11A.

With respect to a flow of warmed air generated by source 40, a flexible hose 41 is coupled to source 40 at one end of hose 41, and is coupled to inlet 16A of warming blanket 11A at the opposite end of hose 41. Hose 41 is configured to deliver a flow of warmed air generated by source 40 though hose 41 to inlet 16A. The connection between hose 41 and inlet 16A may be a rotatable sealing connection, as illustratively shown by double-headed arrow 43, to allow the angle of connection between hose 41 and inlet 16A to be adjusted. In addition, a flexible duct 42 configured to provide a flow of air through the duct is coupled to opening 17A of warming blanket 11A at one end of the duct, and is coupled to inlet 16B of warming blanket 11B at an opposite end of the duct. The connection between duct 42 and opening 17A of warming blanket 11A may be a rotatable sealing connection, as illustratively shown by double-headed arrow 45, to allow the angle of connection between duct 42 and opening 17A to be adjusted. The connection between duct 42 and inlet 16B of warming blanket 11B may be a rotatable sealing connection, as illustratively shown by double-headed arrow 47, to allow the angle of connection between duct 42 and inlet 16B to be adjusted. As illustrated in system 10, opening 17B of warming blanket 11B is sealed with seal 18B. In various example, flexible duct 42 is formed as a partially detachable portion of the warming blanket, such as a partially detachable portion of the upper layer 12, as illustrated by the dashed line 42 illustratively representing the partially detachable duct affixed to upper layer 12. When not used, the partially detachable duct 42 remains affixed to upper layer 12, and seals the opening 17. If used to couple warming blanket 11A to another warming blanket, such as warming blanket 11B, the partially detachable duct 42 is partially detached from upper layer 12, and the end 42A is coupled to the inlet of another warming blanket, such as inlet 16B of warming blanket 11B. When partially detached, the end of partially detachable duct 42 oppose end 42A remains attached to opening 17A, allowing a flow of air to pass through opening 17A and through the now partially detached duct 42 to be received at the warming blanket coupled to end 42A.

As configured, source 40 may provide a flow of warmed air through hose 41 that is received at inlet 16A of warming blanket 11A. The flow of warmed air received at inlet 16A passes through inlet 16A and inflates the passageways 15A of warming blanket 11A, and is distributed out through bottom layer 13A of warming blanket 11A via the porous material or perforations provided in bottom layer 13A. In addition, a portion of the flow of warmed air moving through passageways 15A will also arrive at opening 17A of warming blanket 11A, and will flow out through opening 17A and through duct 42 to be received at inlet 16B of warming blanket 11B. The flow of air received at inlet 16B will continue to flow through inlet 16B and will inflate warming blanket 11B by flowing throughout the passageways 15B. The air flowing through passageways 15B will then be distributed out through bottom layer 13B of warming blanket 11B via the perforations provided in bottom layer 13B. Further, because opening 17B of warming blanket 11B is sealed, no air flow will pass out of warming blanket 11B through opening 17B.

When configured as shown in FIG. 2, system 10 provides a way for a single source of a flow of warmed air, such as source 40, to provide the flow of air to a plurality of warming blankets, such as warming blankets 11A and 11B, by coupling the warming blankets together. In addition, warming blankets 11A and 11B may be located for example so that at least some portion of side 23A of warming blanket 11A is in physical contact with at least some portion of side 24B of warming blanket 11B, thus providing an overall larger surface made up of the bottom layers 13A and 13B of both warming blankets for warming a patient. In various examples, one or both of sides 23A and 24B incudes a mechanism, such as tie strips, or an adhesive strip, that is arranged to allow at least some portion of sides 23A and 24B to be affixed to one another in order to secure warming blankets 11A and 11B in a side-by-side flat configuration. In another examples, rotatable sealing connections provided at opening 17A of warming blanket 11A and at inlet 16B of warming blanket 11B may be manipulated, for example rotated relative to duct 42, so that end 21A of warming blanket 11A is brought into a position that is proximate to end 22B of warming blanket 11B. By positioning warming blankets 11A and 11B in this configuration, an extended length sectional warming blanket may be formed having a length of approximately the longitudinal lengths of warming blankets 11A and 11B combined. In various examples, one or both of ends 21A and 22B comprise a mechanism to allow these ends to be affixed to one another, as described above with respect to side 23A and 24B. In still another example, end 21A of warming blanket 11A may be rotated to a 90-degree position relative to warming blanket 11B and so that end 21A is located proximate to a portion of side 24B of warming blanket 11B. In various examples of this configuration, end 21A may or may not be affixed to a portion of side 24B of warming blanket 11B. The configurations may be used to form a multi-sectional warming blanket including warming blankets 11A and 11B having substantially a right angle between the longitudinal axes of the warming blankets. Similarly, warming blanket 11B may be rotated so that end 22B of warming blanket 11B is located proximate to side 23A of warming blanket 11A, and may or may not be affixed to side 23A, to form a configuration of the warming blankets 11A and 11B, again including a right angle between the longitudinal axes of the warming blankets. These 90-degree configurations may be used for example to cover a torso and one arm extended from the torso of a patient during a procedure that requires patient warming while having access to the second arm of the patient.

In another example, an angle (e.g., an angle less than 90-degrees) as illustrated by double-headed arrow 49 may be as an acute angle formed relative to side 23A of warming blanket 11A and side 24B of warming blanket 11B. In this example, warming blankets 11A and 11B may comprise a "butterfly wing" configuration that is useful for various patient warming applications, such as covering and warming the arms of a patient when the arm is extended outward from the torso of the patient, or for example to cover both legs of the patient. In another example, an angle (e.g., angle greater than 90-degrees but less that 180-degrees) as illustrated by double-headed arrow 49 may be as an obtuse angle formed relative to side 23A of warming blanket 11A and side 24B of warming blanket 11B. This configuration would result in a "butterfly wing" configuration similar to that described above with respect to rotation angles of less than 90-degrees, but for example provides inlet 16A and opening 17B on outside edges of the configurations as compared to configurations using the acute angles.

Other configuration of system 10 are possible and are contemplated by the systems described in the disclosure. For example, hose 41 may include more than one outlet, allowing hose 41 to be coupled directly to multiple sectional warming blankets directly at the same time. For example, hose 41 may include a first branch coupled directly to inlet 16A of warming blanket 11A, and a second branch coupled directly to inlet 16B of warming blanket 11B. In another example, opening 17B is not sealed, and is coupled as an air outlet to provide a flow of air to another sectional warming blanket (not shown in FIG. 2) either directly or via another coupling duct (not shown in FIG. 2). In various examples, instead of inlet 16A being coupled to hose 41, inlet 16A is coupled to the flow of air provided by source 40 by being coupled to another sectional warming blanket that is coupled, either direct or through still another sectional warming blanket, to source 40.

In each of these example configurations, system 10 may be placed in proximity to a patient so that the bottom surfaces of bottom layers 13A and 13B of the warming blanket 11A, 11B are located in proximity to some portion or portions of the body of the patient, and thus provide the warming air flow to the patient. Use of a standardized sectional warming blanket that can be coupled to other sectional warming blankets and configured as described with respect to FIG. 2 and as described throughout this disclosure to provide a versatile system that may be arranged in various configurations to provide patient warming for various sizes of patients and for the various positions that these patients may need to be positioned during different procedures.

Figure 3:
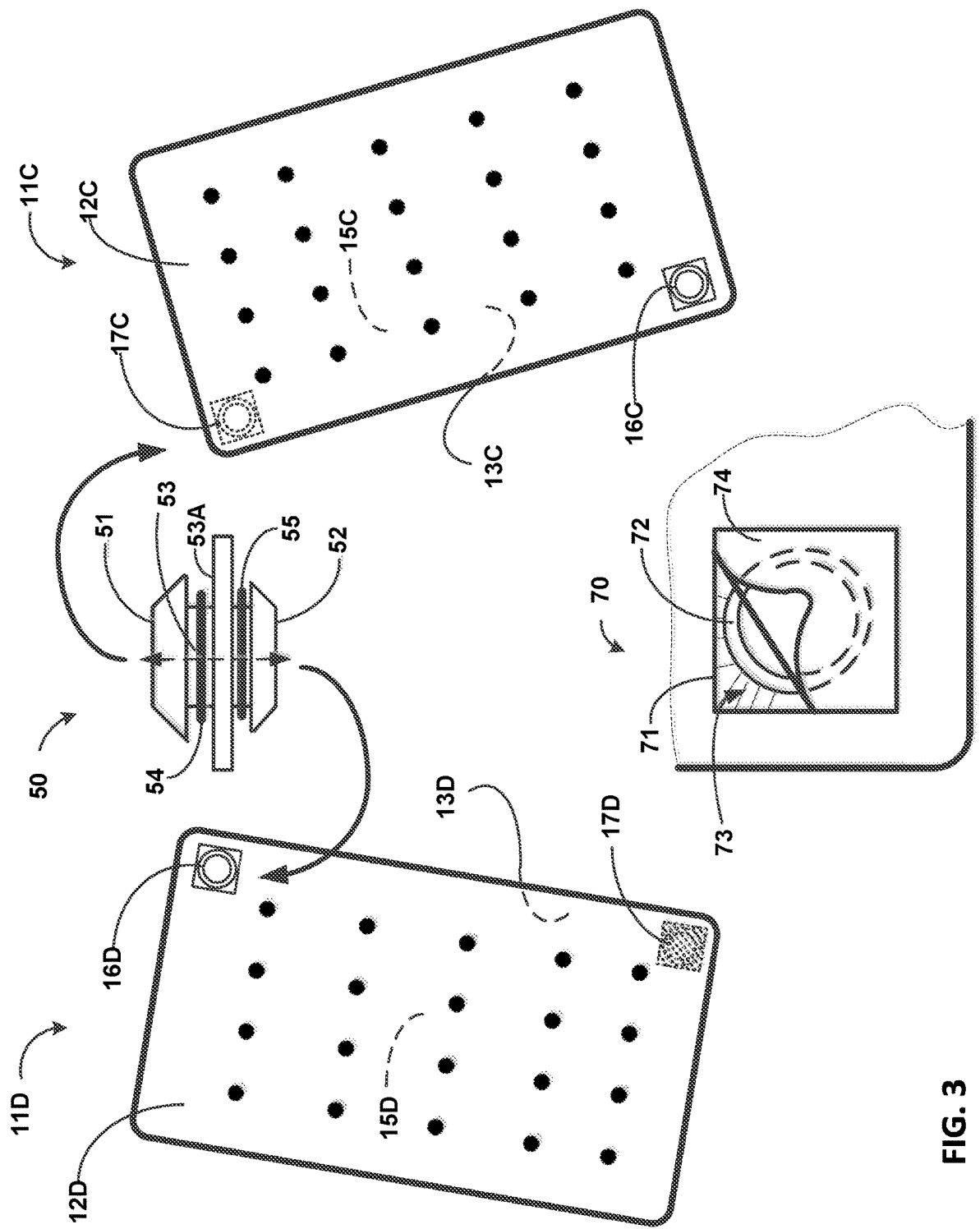
FIG. 3 illustrates devices and techniques for coupling sectional warming blankets together in accordance with one or more example implementations and techniques described in this disclosure.

FIG. 3 illustrates devices and techniques for coupling sectional warming blankets 11C and 11D together in accordance with one or more example implementations and techniques described in this disclosure. Warming blanket 11C includes a non-porous upper layer 12 and a porous or perforated bottom layer 13C that allows profusion of air through bottom layer 13C for patient warming. Although in some examples both upper layer 12 and bottom layer 13C are both formed from a porous or perforated material. Warming blanket 11C includes an inlet 16C located on upper layer 12C, and providing an opening through upper layer 12C to the interior air passageways 15C within the warming blanket, and an opening 17C located on the bottom layer 13C, which provides an opening through bottom layer 13 to the passageways 15C. Similarly, warming blanket 11D includes an inlet 16D located on upper layer 12D, and providing an opening through upper layer 12 to the interior air passageways 15D within the warming blanket, and an opening 17D located on the bottom layer 13D. As illustrated in FIG. 3, opening 17D is sealed, and thus does not provide an opening through bottom layer 13D. As also illustrated in FIG. 3, the upper corner of warming blanket 11C having opening 17C on bottom surface 13C is positioned nearby the upper corner of warming blanket 11D having inlet 16D on upper surface 12D.

In one example, a coupling device 50 may be used to couple opening 17C to inlet 16D, and thus couple warming blankets 11C and 11D together to share a flow of air provided to inlet 16C of warming blanket 11C. Coupling device 50 includes a first tapered end 51 at one end of a shaft 53, and a second tapered end 52 at an opposite end of shaft 53. Shaft 53 is hollow (i.e., non-solid or having a tubular cavity formed from walls of the shaft) to allow a flow of air through the shaft, as illustrated by the dashed double-headed arrow running through shaft 53. In addition, shaft 53 included a stop ring 53A located on shaft 53 approximately midway between tapered end 51 and tapered end 52. Examples of coupling device 50 may also include one or more sealing rings, including for example an O-ring made of some type of flexible material, illustrated by seals 54, 55 surrounding shaft 53.

Tapered end 52 may be dimensioned, in conjunction with shaft 53 and stop ring 53A, so that the tapered end 52 may be inserted into inlet 16D of warming blanket 11D, the tapered end 52 securing the coupling device 50 to inlet 16D, and the stop ring 53A preventing the coupling device from extending into inlet 16D beyond the stop ring 53A. In various examples, seal 55 provides an air seal between tapered end 52 and inlet 16D when the coupling device 50 is fully received in inlet 16D. Similarly, tapered end 51 may be dimensioned, in conjunction with shaft 53 and stop ring 53A, so that the tapered end 51 may be inserted into opening 17C of warming blanket 11C, the tapered end 51 securing the coupling device 50 to opening 17C, and the stop ring 53A preventing the coupling device 50 from extending into opening 17C beyond the stop ring 53A. In various examples, seal 54 provides an air seal between tapered end 51 and opening 17C when the coupling device 50 is fully received in opening 17C.

Coupling device 50 may be used to couple warming blankets 11C and 11D by first inserting tapered end 52 into inlet 16D until the tapered end is fully receiving in inlet 16D, and in some examples having stop ring 53A contact inlet 16D. Following insertion of coupling device 50 into inlet 16D, warming blanket 11C may be located so that opening 17C is positioned over tapered end 51 of coupling device 50, and may be lowered onto coupling device 50 so that coupling device 50 is received in opening 17C, and in some examples to the extent that stop ring 53A has been brought into contact with opening 17C. Once the coupling is completed to both inlet 16D and opening 17C as described above, the hollow through shaft 53 provides an air flow passageway between the passageways 15C of warming blanket 11C and the passageways 15D of warming blanket 11D. This coupling of the warming blankets is secured by the coupling device, and in some examples may be otherwise sealed with respect to air leak around the outside portion of shaft 53 by seals 54, 55.

In various examples, coupling device 50, inlet 16D, and opening 17C are dimensioned so that either of the tapered ends 51, 52 may be inserted into inlet 16D and opening 17C, e.g. coupling device is reversible end-to-end and still capable of being used as described above. Further, coupling device may be inserted in any order with respect to inlet 16D and opening 17C. Further, coupling device 50, and inlet 16D, and opening 17C may be dimensioned so that once inserted, coupon device 50 provides a rotatable and sealing coupling between warming blankets 11C and 11D that allows the orientation of one warming blanket to be rotatably adjusted relative to the other warming blanket. This adjustable orientation feature may be accomplished by rotation of inlet 16D and/or rotation of opening 17C around the shaft portion of the coupling device 50. Thus, coupling device 50 may provide a fast, easy method to couple two sectional warming blankets together to form all or some part of a multi-sectional warming blanket, and allowing for adjustment, via rotational orientation, of the configuration of the multi-sectional warming blanket. Examples of some of these adjustable orientations are illustrated and described with respect to FIGS. 4A-4D.

Referring again to FIG. 3, connective opening is another example of a technique that may be used to couple warming blankets 11C and 11D to provide an air flow passageway between the warming blankets. Connective opening 70 in some examples is opening 17C of warming blanket 11C. As illustrated, connective opening incudes a plate 71 bonded or otherwise affixed to a layer, e.g. bottom layer 13C of warming blanket 11C. Plate 71 further includes a collar 72 surrounded by a top surface 73 surrounding collar 72. Top surface 73 is coated with an adhesive, such as a semi-permanent adhesive, or a selective adhesive, that allows top surface 73 to be affixed to an inlet, such as inlet 16D of warming blanket 11D, when top surface 73 is brought into contact with the inlet. Top surface 73 may be covered with a cover sheet or release liner 74 that covers the top surface 73 to protect the adhesive, but may be peeled or otherwise removed from top surface 73 in order to expose the adhesive, as illustrated by the partially peeled back cover sheet 74 shown in FIG. 3.

In various examples, opening 70 as originally provided includes cover sheet 74, which if not removed or peeled from top surface 73 provides an air seal that is adequate to withstand and seal opening 70 relative to the air pressure level that would normally be provided within the warming blanket where opening 70 and cover sheet 74 are provided. However, cover sheet 74 when removed from top surface 73 exposes the adhesive layer of top surface 73. Once exposed, the adhesive may be brought into contact with inlet, such as inlet 16D of warming blanket 11D. When brought into contact with another inlet or opening, the adhesive affixes top surface 73 to the inlet or opening that is contacted, and provides a secure coupling of opening 70 with the other opening, e.g., inlet 16D. Dimensions of collar 72 and portions of inlet 16D may also be arranged to engage each other in a manner that also helps secure opening 70 and inlet 16D together. As one example, collar 72 may be dimensioned to be insertable, to some extent, into an opening or a rim portion of inlet 16D.

In some examples, both opening 70 and inlet 16D comprise an adhesive that affixes to itself, or affixes to a different adhesive or other compounds when brought into contact with one another. In such examples one adhesive or compound may be provided with opening 70, and a same or a corresponding adhesive or compound may be provided by inlet 16D so that when the adhesives and/or compounds are brought into contact with each other, they affix opening 70 to inlet 16D. The adhesive and/or other compounds may provide an air seal to prevent air leaks between opening 70 and inlet 16D relative to areas outside the interior passageways 15C and 15D of the coupled warming blankets.

In some examples, the adhesive is a pressure sensitive adhesive, and/or a non-tacky reusable adhesive. Pressure Sensitive Adhesive (PSA) typically consist of a PSA coated onto a polymer film such as plasticized polyvinyl chloride (PVC) or high quality paper stock, which are supplied on a siliconized release paper to protect the PSA. For purposes of the present disclosure, a "non-tacky adhesive" is an adhesive that bonds to certain materials by application of pressure, but does not feel tacky to the human touch. The non-tacky adhesive composition preferably consists of a terpolymer containing 35% acrylonitrile, 58% butadiene and 7% isoprene prepared by a cold process, with an average Mooney viscosity of 46, that goes under the Tradename Nipol® DN-1201L (Zeon Chemical Co). Alternately, the same terpolymer can be used with either a higher or lower Mooney viscosity. Further, a copolymer consisting of acrylonitrile and butadiene made by the cold process can be used with the weight % of acrylonitrile varying from 18.5 to 36%. The Mooney viscosity can vary from 30 to 90.

Typical examples of acceptable polymer films include, polyethylene in its various densities and chain configurations, polypropylene, ethylene-vinyl acetate copolymers and terpolymers with other monomers such as acrylic monomers, ethylene acrylic acid copolymers and ethylene-methacrylic acid copolymers with either the acid in the acid form or neutralized. For all of these polymers, the surface may be treated with an energetic method such as Corona Treatment or Flame Treatment, to improve the minimum bond strength to the non-tacky adhesive ("NTA"). Materials such as PET or plasticized PVC cannot be used unless the surface of the film contacting the NTA is coated with another material such as an EVA or a vapor coating of metal.

Non-tacky adhesives such as a terpolymer of acrylonitrile, butadiene, and isoprene, or similar copolymer of acrylonitrile and either butadiene or isoprene, commercially available under the brand Nipol® adhesives from Zeon Chemical Co, Louisville, Ky., USA. These adhesives may be "washable" in that their tackiness diminished by dirt or other deleterious surface contact can be restored after cleaning with common cleaning agents including without limitation rinsing with clean water. Thus, these latter adhesives are desired when "cleanability" is a desired feature.

In various examples the PSA or the non-tacky adhesive may be provided on one side of a carrier, such a plastic or substrate. A first side of the carrier may be durably bonded, e.g., permanently affixed, to some portion of the opening 70, such as top surface 73 a second surface of the carrier opposite the first surface of the carrier may be coated with tee PSA or non-tacky adhesive. Coating weights of such adhesives on adhesive carrier can range from about 10 gm/m² to about 300 gm/m² and preferably about 20 gm/m² to about 150 gm/m². Typical substrates to which this embodiment of system 10 is applied include painted metal, polymeric foam board, and the like.

Once coupled in any of the manners described above or otherwise, the passageway through opening 17C and inlet 16D provide an air flow path coupling the passageways 15C of warming blanket 11C to the passageways 15D of warming blanket 11D. Once coupled together by any of the devices or techniques as described above, or the equivalents thereof, a flow of warmed air may provide at inlet 16C of warming blanket 11C, passing through inlet 16C to inflate the passageways 15C of warming blanket 11C, and flowing other through the coupling connection including opening 17C and inlet 16D to inflate the passageways 15D of warming blanket 11D. The coupled warming blankets 11C and 11D may form part or all of a multi-section warming blanket that may then be used for a variety of patient warming applications. Further, if opening 17D of warming blanket 11D is sealed, no air flow will pass out of warming blanket 11D through opening 17D. In the alternative, opening 17D can be further coupled, for example by any of the devices and/or techniques described above or otherwise to an additional sectional warming blanket (not shown in FIG. 3).

FIGS. 4A-4D illustrate example configurations of coupled warming blankets 11C and 11D in accordance with one or more example implementations and techniques described in this disclosure.

Figure 4B:
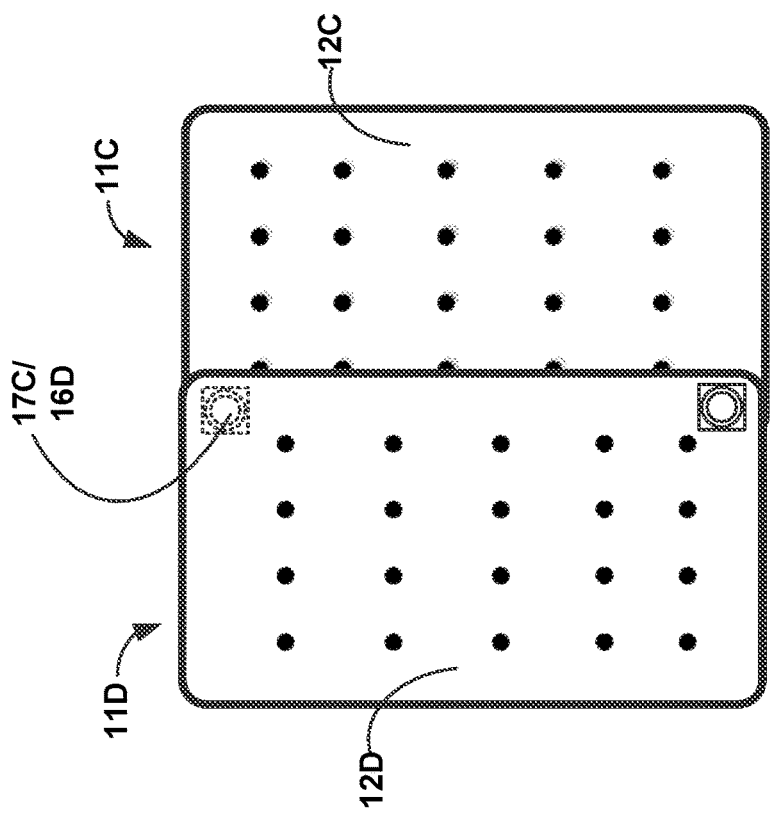
FIGS. 4A-4D illustrate example configurations of coupled warming blankets in accordance with one or more example implementations and techniques described in this disclosure.
Figure 4A:
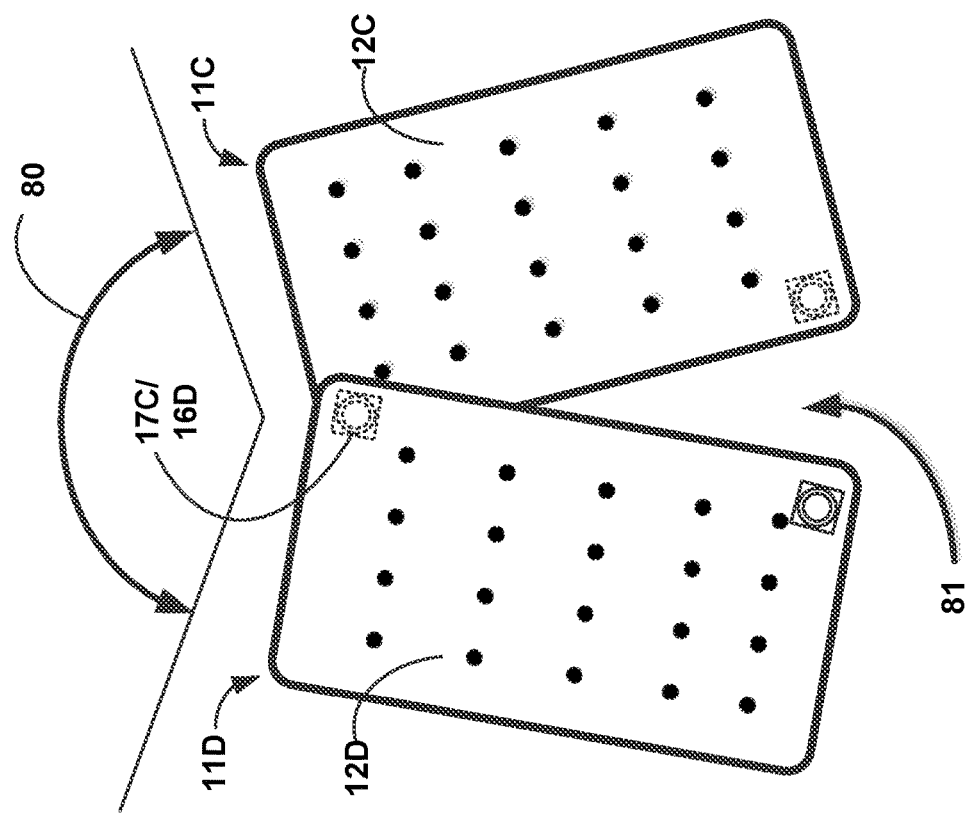

FIG. 4A illustrates first warming blanket 11C coupled through opening 17C to inlet 16D of second warming blanket 11D. The coupling may be accomplished by a coupling device, such as coupling device 50, or may be accomplished by using adhesive(s) as illustrated and described above with respect to FIG. 3. As shown in FIG. 4A, warming blankets 11C and 11D are rotatably oriented relative to coupling 17C/16D so that the top edges of the warming blankets form an obtuse angle represented by double-headed arrow 80. Top layer 12C of warming blanket is partially overlapped in an upper corner of warming blanket 11C by warming blanket 11D. This orientation also creates a space, generally indicated by arrow 81, between the lower portions of the warming blankets.

FIG. 4B illustrates another configuration having first warming blanket 11C coupled through opening 17C to inlet 16D of warming blanket 11D. As described above, the coupling may be accomplished by a coupling device, such as coupling device 50, or may be accomplished by using adhesive(s) as illustrated and described above with respect to FIG. 3. As shown in FIG. 4B, warming blankets 11C and 11D are rotatably oriented relative to coupling 17C/16D so that the top edges of the warming blankets are substantial in-line with each other. A longitudinal side of upper layer 12C of warming blanket 11C is overlapped by a portion of a longitudinal side of warming blanket 11D, and in contrast to FIG. 4A, no space is created between warming blankets 11C and 11D due to the extent of this overlap. In various examples, the orientation illustrated in FIG. 4B may have resulted from an initial orientation as illustrated in FIG. 4A for these warming blankets, and then rotating one or both of the warming blankets around the coupling 17C/16D to achieve the configuration of the warming blankets as illustrated in FIG. 4B.

Figure 4D:
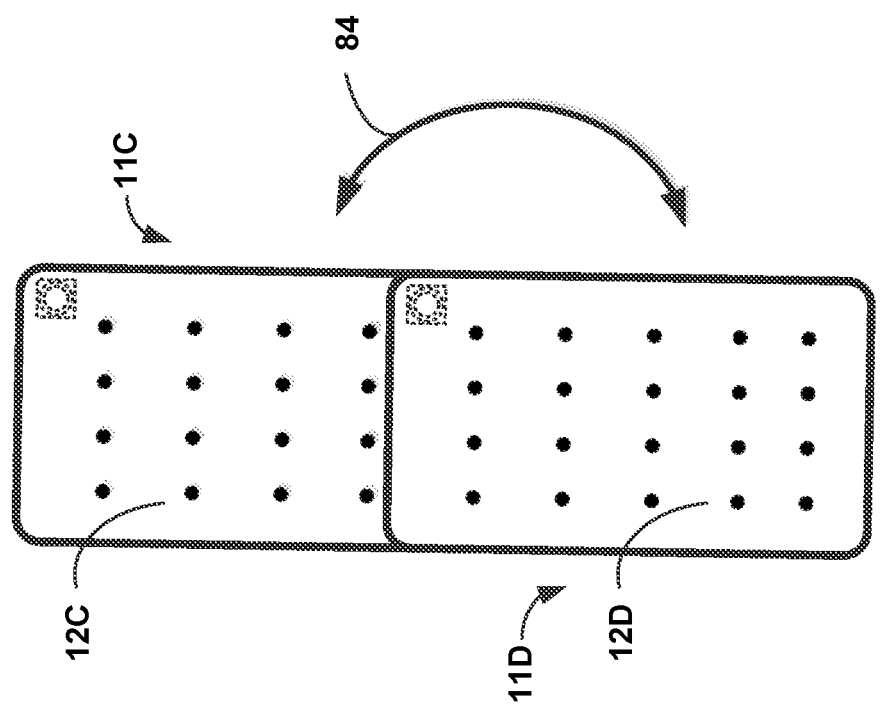
Figure 4C:
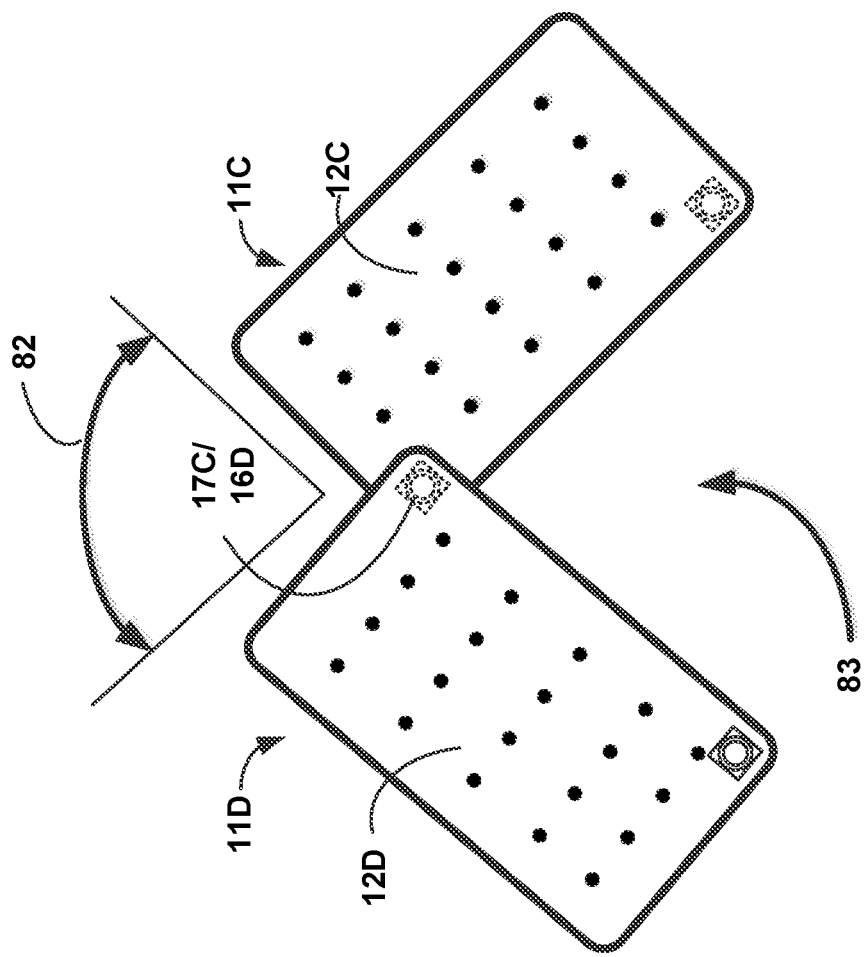

FIG. 4C illustrates another configuration having first warming blanket 11C coupled through opening 17C to inlet 16D of warming blanket 11D. As described above with respect to FIGS. 4A and 4B, the coupling may be accomplished by a coupling device, such as coupling device 50, or may be accomplished by using adhesive(s) as illustrated and described above with respect to FIG. 3. As shown in FIG. 4C, warming blankets 11C and 11D are rotatably oriented relative to coupling 17C/16D so that the top edges of the warming blankets form substantially a 90-degree angle relative to each other, as represented by double-headed arrow 82. Top layer 12C of warming blanket 11C is partially overlapped in an upper corner by warming blanket 11D. This orientation also creates a space, generally indicated by arrow 83, between the lower portions of the warming blankets. In various examples, the orientation illustrated in FIG. 4C may have resulted from an initial orientation as illustrated in FIG. 4A for these warming blankets, and then rotating one or both of the warming blankets around the coupling 17C/16D to achieve the configuration of the warming blankets as illustrated in FIG. 4C.

FIG. 4D illustrates still another configuration having first warming blanket 11C coupled through opening 17C to inlet 16D of warming blanket 11D. As described above with respect to FIGS. 4A-4C, the coupling in FIG. 4D may be accomplished by a coupling device, such as coupling device 50, or may be accomplished by using adhesive(s) as illustrated and described above with respect to FIG. 3. As shown in FIG. 4D, warming blankets 11C and 11D are rotatably oriented relative to coupling 17C/16D so that the bottom end of warming blanket 11C is rotated around warming blanket 12D to the extent that the longitudinal edges of both warming blankets are all co-liner or parallel, as generally indicated by arrow 84. Top layer 12C of warming blanket 11C is partially overlapped in an upper width dimension by a width portion of warming blanket 11D. In this orientation, there is no space between the width edges of the warming blankest due to the overlap. In various examples, the orientation illustrated in FIG. 4D may have resulted from an initial orientation as illustrated in FIG. 4A for these warming blankets, and then rotating one or both of the warming blankets around the coupling 17C/16D to achieve the configuration of the warming blankets as illustrated in FIG. 4D. The arrangements illustrated in FIG. 4D provides a multi-sectional warming blanket with an overall longitudinal dimension that is almost the sum of the longitudinal dimension of each of the warming blankets 11C and 11D.

Figure 5:
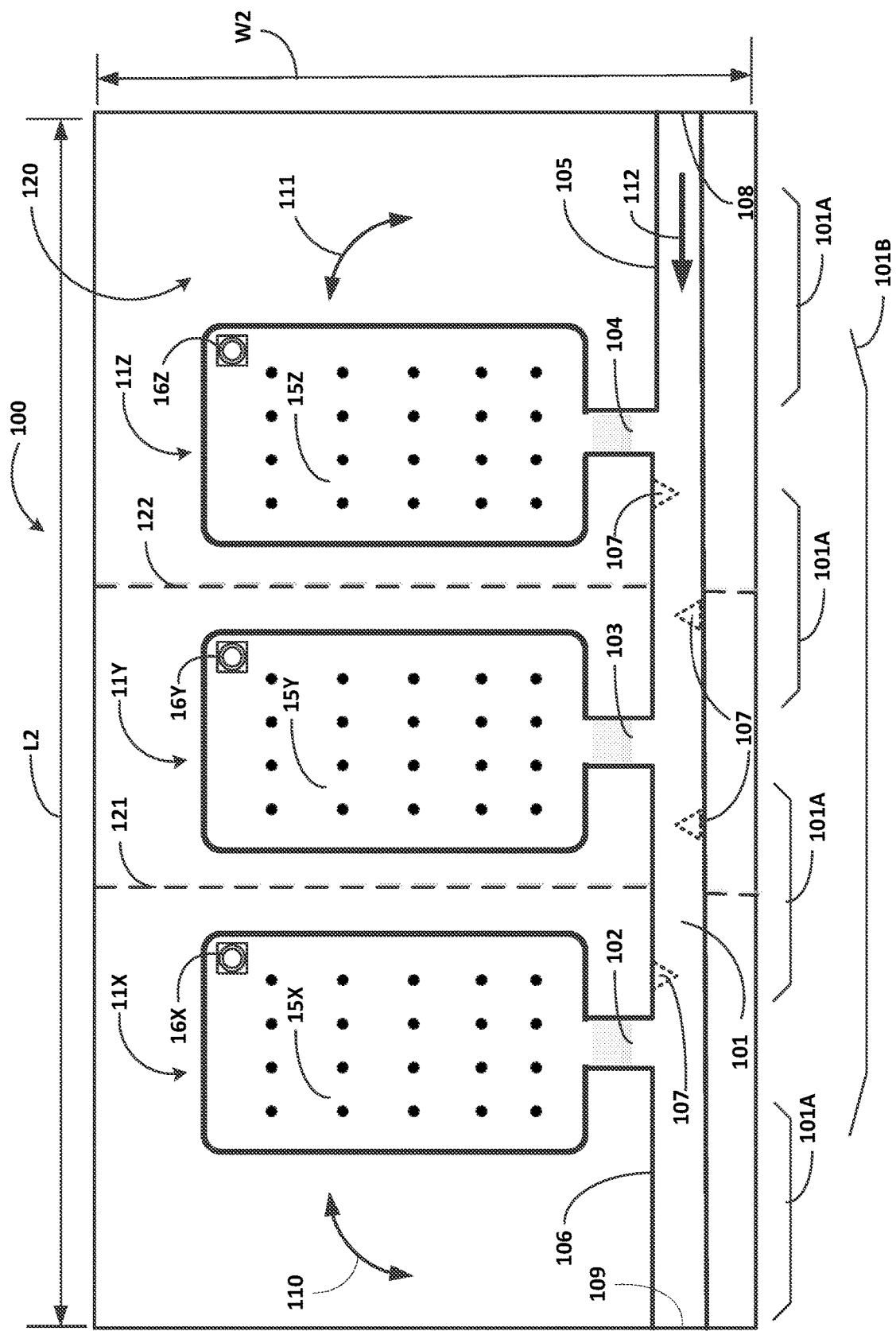
FIG. 5 illustrates a top view of a multi-sectional warming blanket according to various examples implementations and techniques described in this disclosure.

FIG. 5 illustrates a top view of an example multi-sectional warming blanket 100 according to various techniques described in this disclosure. As illustrated, multi-sectional warming blanket 100 (herein after referred to a "warming blanket 100") comprises a plurality of individual sectional warming blankets illustratively shown in FIG. 5 as warming blankets 11X, 11Y, and 11Z, formed on the section of web material each coupled to a common air duct 101. Warming blanket 100 is not limited to having a particular number of sectional warming blankets, and may include more or less sectional warming blankets than the illustrative warming blankets 11X, 11Y, and 11Z shown in FIG. 5. Each of the sectional warming blankets 11X, 11Y, and 11Z may include the features and may provide the functions of any of the example warming blankets described herein, for example warming blanket 11 as illustrated and described with respect to FIG. 1, or for example any of warming blankets 11A, 11B as illustrated and describe with respect to FIG. 2, or any of the examples of warming blankets 11C, 11D illustrated and described with respect to FIG. 3 and FIGS. 4A-4D.

Referring again to FIG. 5, web 120 may be generally rectangular in shape, having a length dimension L2 and a width dimension W2. In various examples, the length of dimension L2 is in a range of about 28 to 120 inches, and the width of dimension W2 is in a range of about 20 to 60 inches. As shown in FIG. 5, each of the warming blankets 11X, 11Y and 11Z includes an input duct coupling the warming blanket to the common air duct 101. Warming blanket 11X is coupled to air duct 101 though input duct 102, wherein input duct 102 may be configured to provide a flow of air from air duct 101 to the passageways 15X of warming blanket 11X. Similarly, warming blanket 11Y is coupled to air duct 101 though input duct 103, wherein input duct 103 may be configured to provide a flow of air from air duct 101 to the passageways 15Y of warming blanket 11Y. Further, warming blanket 11Z is coupled to air duct 101 though input duct 104, wherein input duct 104 may be configured to provide a flow of air from air duct 101 to the passageways 15Z of warming blanket 11Z. The common air duct 101 includes a first open or end 108 at a first side of web 120, and a second opening or end 109 at a second side of web 120.

In various examples, the warming blankets included in warming blanket 100 include an intermediate section between each of the inlet ducts along air duct 101. In various examples, one end 108, 109 of the common air duct 101 may be sealed, and the opposite end may be left unsealed so that the common air duct 101 may be coupled to a source of a flow of air, as illustratively represented by arrow 112. The flow of air 112 delivered to air duct 101 proceeds through air duct 101 and through each of input ducts 102, 103, and 104 to inflate the warming blankets 11X, 11Y, and 11Z, respectively.

In various examples, air duct 101 includes one or more air-guides 107. Air guides 107 may comprise flexible and/or expandable portions of air duct 101, which allows air duct 101 to be bent to a shape other than a straight line shape without creating an obstruction, such as a kink or fold, in the passageway through air duct 101. By providing the air guides 107, and allowing for bending of air duct 101 at various points along the duct, the relative positions of warming blankets 11X, 11Y, and 11Z may be manipulated, for example with respect to the longitudinal orientation relative to each other, as illustratively represented by double-headed arrows 110 and 111. In some examples, manipulation may include bending of air duct 101 so that a general planar orientation of one of the warming blankets 11X, 11Y, or 11Z is non-coplanar with the general planar orientation of another one of the warming blankets 11X, 11Y, or 11Z. Web 120 may include weakened areas 121, 122 in the form or a line of weakness or a perforation in the web 120 that may be torn to further separated warming blanket 11X from 11Y, and warming blanket 11Y from 11Z relative to web 120 while keeping each warming blanket coupled to the common air duct 101. In some examples weakened areas 121, 122 traverse the entire width dimension W2 of web 120. In other examples, weakened areas 121, 122 only travers a portion of the wide dimension W2 of web 120, for example only the areas above common air duct 101 and in-between the portions of web 120 that includes the warming blankets.

Weakened areas 121 and 122 may further aid in the manipulation of the configuration of warming blankets 11X, 11Y, and 11Z relative to each other. For example, sectional warming blanket 11Y may be oriented to lie generally in a first plane, the first plane placing warming blanket 11Y over the torso of a patient (not shown in FIG. 5) while the patient is in a supine positon. Air duct 101 could be manipulated, e.g. bent, so that sectional warming blanked 11X lies generally in a plane that intersects the first plane at some angle, e.g., 90-degrees or less, while leaving the longitudinal dimensions of sectional warming blankets 11X and 11Y parallel to each other, thereby placing warming blanket 11X in a side position relative to the position of sectional warming blanket 11Y. When configure in this matter, sectional warming blanket 11X may be manipulated to be located along the side of the patient when sectional warming blanket 11Y remaining over the top side of the patient while the patient is in the supine position. Similarly, air duct 101 may be further manipulated to place sectional warming blanket 11Z so that sectional warming blanket 11Z lies generally in a plane that intersects the first plane at some angle, e.g., 90-degrees or less, while leaving the longitudinal dimensions of sectional warming blankets 11Y and 11Z parallel to each other. When configured in this matter, sectional warming blanket 11Z may be placed in a positon that allows sectional warming blanket 11Z to warm a side of the patient opposite the side being warmed by sectional warming blanket 11X. The ability to manipulate air duct 101 as described above, or otherwise bend and manipulate air duct 101 allows the multi-sectional warming blanket to be manipulated to better comport to a shape and position of a patient, and thus may provide more efficient warming of the patient, and may be advantageous during various patient warming procedures compared to conventional patient warming blankets that lie generally a single flat planar arrangement.

Examples of warming blanket 100 thus allows for variations in the number of sectional warming blankets that may be included in the system, and also provides for manipulation of the relative positions of the sectional warming blankets that end up being included in the configuration of warming blanket 100. In some examples, one or more of warming blankets 11X, 11Y, and 11Z include an inlet configured to receive a flow of air provided directly to the warming blanket through the inlet. As illustrated, warming blanket 11X includes an inlet 16X, warming blanket 11Y includes an inlet 16Y, and warming blanket 11Z includes an inlet 16Z. In such examples, the input of a flow of air to the warming blanket 100, instead of being provided to air duct 101, may be provided to one or more of inlets 16X, 16Y, and 16Z. In these examples, air duct 101 may be sealed at both ends 108 and 109. The input duct coupled the warming blanket that is directly receiving the flow of warmed air may become an output duct, and provide a flow of the warmed air to air duct 101 from the passageways 15 of the warming blanket, wherein duct 101 then functions as described above to distribute the flow of air to the other warming blankets that are coupled to the air duct.

Many of the example warming blankets illustrated and described in this disclosure are illustrated and described as having substantially a rectangular shape. However, examples of warming blankets described with respect to the figures and throughout this disclosure are not limited to having a particular shape that may be defined by the periphery of the warming blanket as an initial shape and configuration for the warming blanket. Examples of warming blankets 11 and 11A-D as provided in FIGS. 1, 2A-2B, 3A-3B, 4A-4B, and 5 are illustrative of a rectangular shaped warming blanket. However, other shapes, such as but not limited to square shapes and elliptical shapes, are examples of other possible shapes for the periphery of a warming blankets, and are contemplated by the examples provided in this disclosure.

Figure 6A:
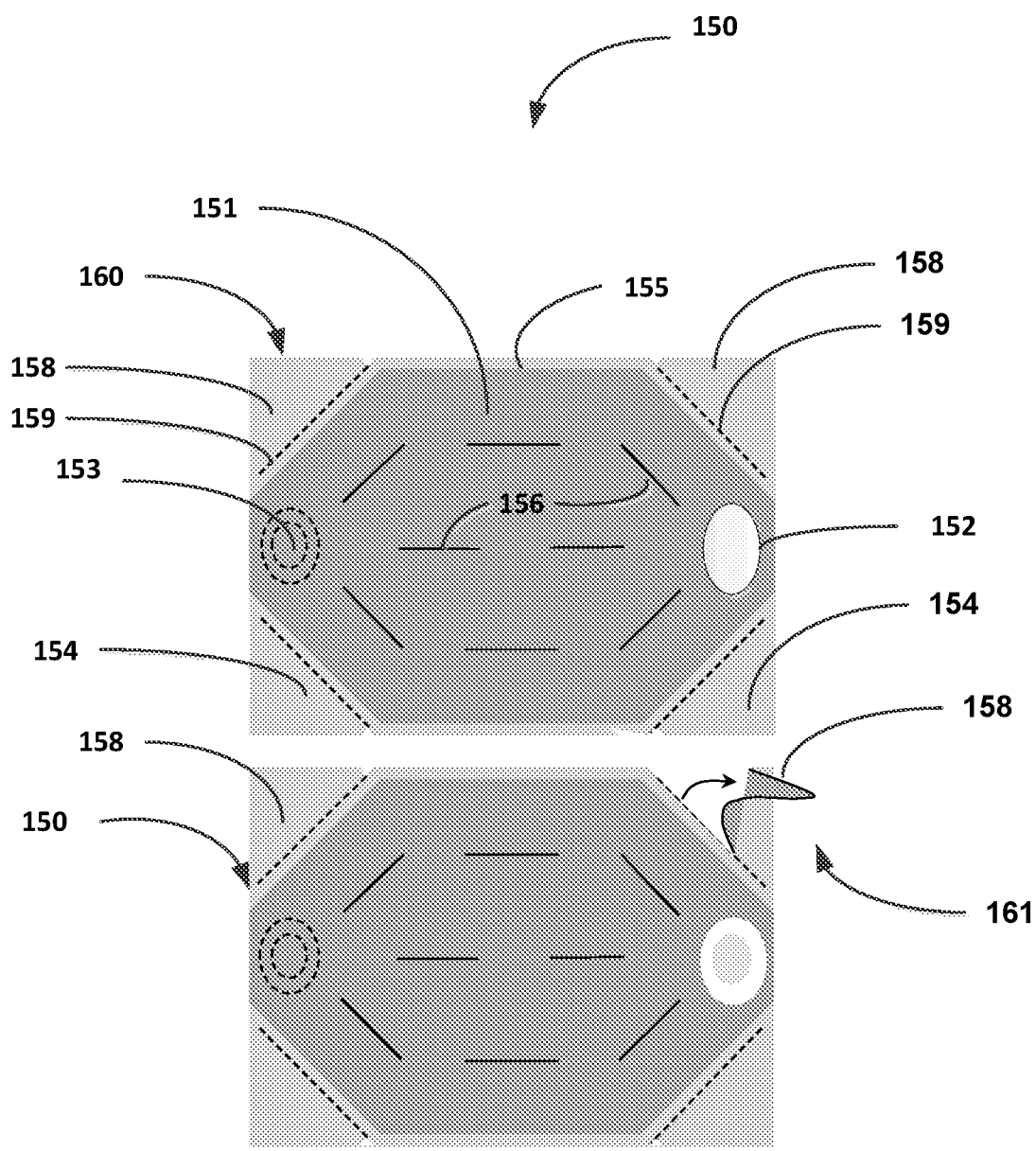
FIG. 6A is an example of a sectional warming blanket according to various examples described in this disclosure.

FIG. 6A is an example of a sectional warming blanket 150 according to various examples described in this disclosure. Sectional warming blanket 150 may be formed from a web material having overlapping layers of film, generally indicated as web material 160, wherein the layers of the web material 160 are processed to bond the layers of the web material to form the interior air passageways 151 for the sectional warming blanket 150. Sectional warming blanket 150 (hereinafter referred to as "warming blankets 150") includes an upper layer formed from a non-porous material, and a bottom layer formed from a porous material or a perforated material, the bottom layer arranged to allow passage of air through the bottom layer. Although in some examples both upper layer and bottom layer are both formed from a porous or perforated material. The upper layer is bonded to the bottom layer along a periphery 155 and at seals 156, in a similar manner as described above for example with respect to warming blanket 11 illustrated and described with respect to FIG. 1, but wherein seals 156 as shown in FIG. 6A provide a linear stake bounding the upper layer and the lower layer along a line having a length dimension.

Referring again to FIG. 6A, in various examples, the periphery 155 of warming blanket 150 may form an irregular octagonal shape, but the shape of warming blanket 150 is not limited to this or any other particular shape. Warming blanket 150 includes an inlet 152 providing a passageway to the interior passageways 151 of warming blanket 150. Inlet 152 may be coupled to a source of a flow of warmed air, and when a flow of warmed air is provided to inlet 152, warming blanket 150 may be inflated to distribute the flow of warmed air to the bottom layer via passageways 151. Warming blanket 150 also includes an opening 153. In various examples, opening 153 is located on the bottom layer of warming blanket 150. Opening 153 in some examples is a re-enforced area of the warming blanket, for example an area with a thicker or a second layer of material, that allow warming blanket to provide another passageway for coupling warming blanket 150 to another warming blanket. In various examples, opening 153 is sealed by the web material 160 or by the second layer of reinforcing material, which may comprise a line or lines of weakness formed in the material, and is configured to be punched or pushed open, for examples by tearing through the material sealing the opening 153 to create a passageway through the web material at opening 153 if warming blanket 150 is to be coupled to another warming blanket. In the alternative, opening 153 may remain sealed (e.g., opening 153 is not "punched" open), and provides a seal of passageways 151 for warming blanket 150 when warming blanket is intended to be used along or is not intended to be coupled to a further warming blanket other than any warming blankets providing the flow of warmed air at inlet 152. Coupling another warming blanket to warming blanket 150 is not limited to any particular mechanism or technique, and may include a coupling device, such as coupling device 50 shown in FIG. 3, or use of an adhesive coupling technique, as described herein and including any equivalents thereof.

Warming blanket may also include one or more external areas 158 formed from the web material 160 surrounding and periphery 155 and extending outside the passageways 151. Each of external areas 158 may include a cutline 159 forming a weakened portion of web material 160 that allows the areas 158 to be partially or completely separated from the warming blanket 150 when cutline 159 is torn, as shown generally by arrow 161. When partially torn away from the warming blanket 150, external areas 158 may be used as secure ties to help fasten the warming blanket 150 to other sectional warming blankets and/or to a patient when the warming blanket is in use.

Figure 6B:
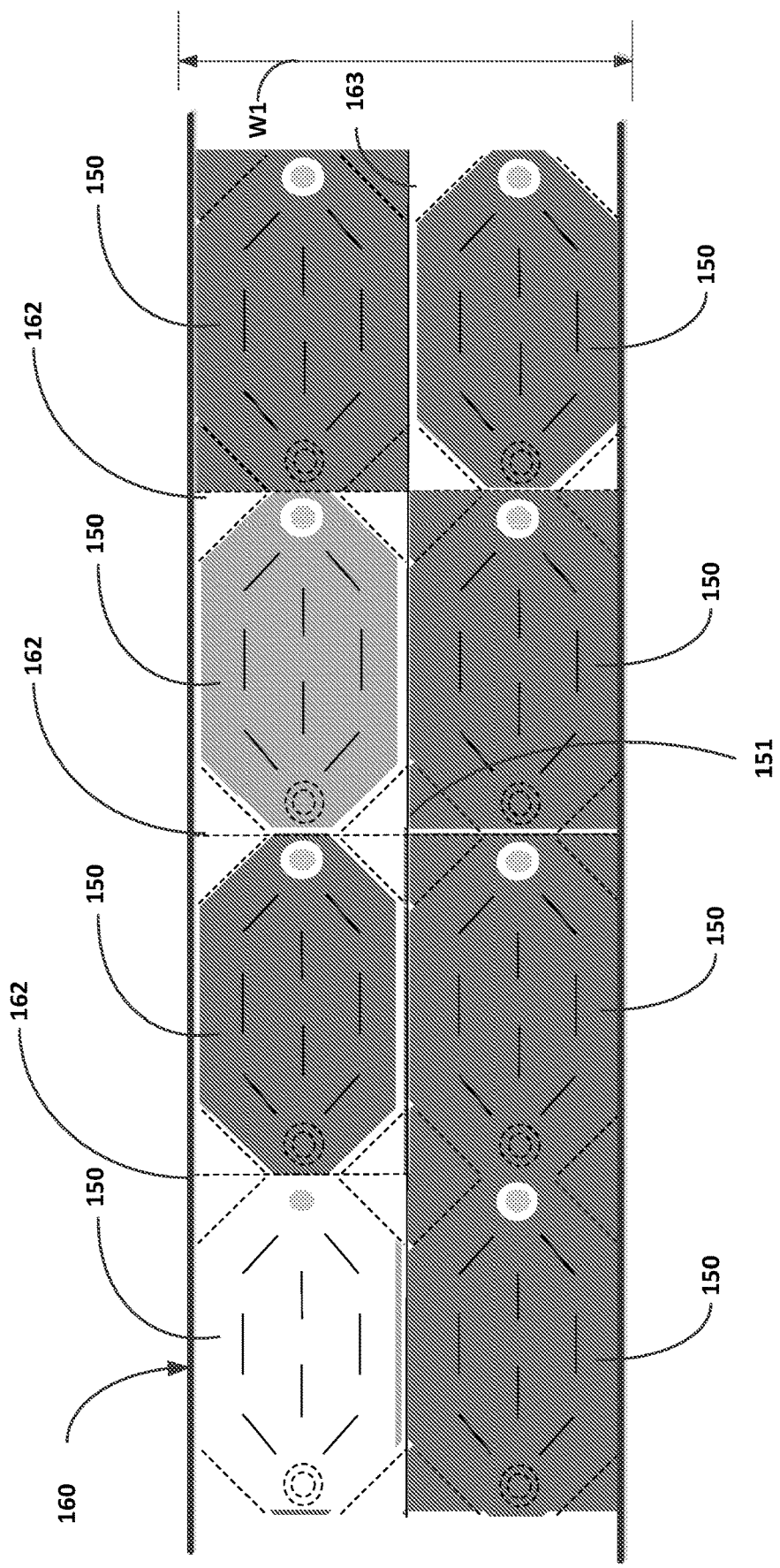
FIG. 6B illustrates a plurality of warming blankets manufactured on a continuous web material in accordance with one or more example implementations and techniques described in this disclosure.

FIG. 6B illustrates a plurality of warming blankets 150 manufactured on a continuous web material 160 in accordance with one or more example implementations and techniques described in this disclosure. In various examples, web material 160 has an undefined length used to provide a series of warming blankets 150 along the length of the web material. Each individual warming blanket 150 provided on the web material 160 is further segmented by cutlines 162 across a width dimension W1 of the web material 160. The width dimension is not limited to any particular width, and in some examples may only be wide enough to provide one row of warming blankets 150 across the width of web material 160. In other examples, the widths dimension may of a width that is capable of providing two or more rows of warming blankets across the width of web material 160.

In examples that include more than one row of warming blankets provided across the width dimension, a separation line 163 may be formed between the row to allow conversion of each row of warming blankets to be separated from the adjacent row or rows. Further processing of web material 160 may include separation of the rows, but leaving warming blankets 150 within each row coupled along cutlines 162. The individual rows may then be further processed, such as formed into a roll, or folded into an accordion shaped manner for packaging and shipment to a customer.

Figure 6C:
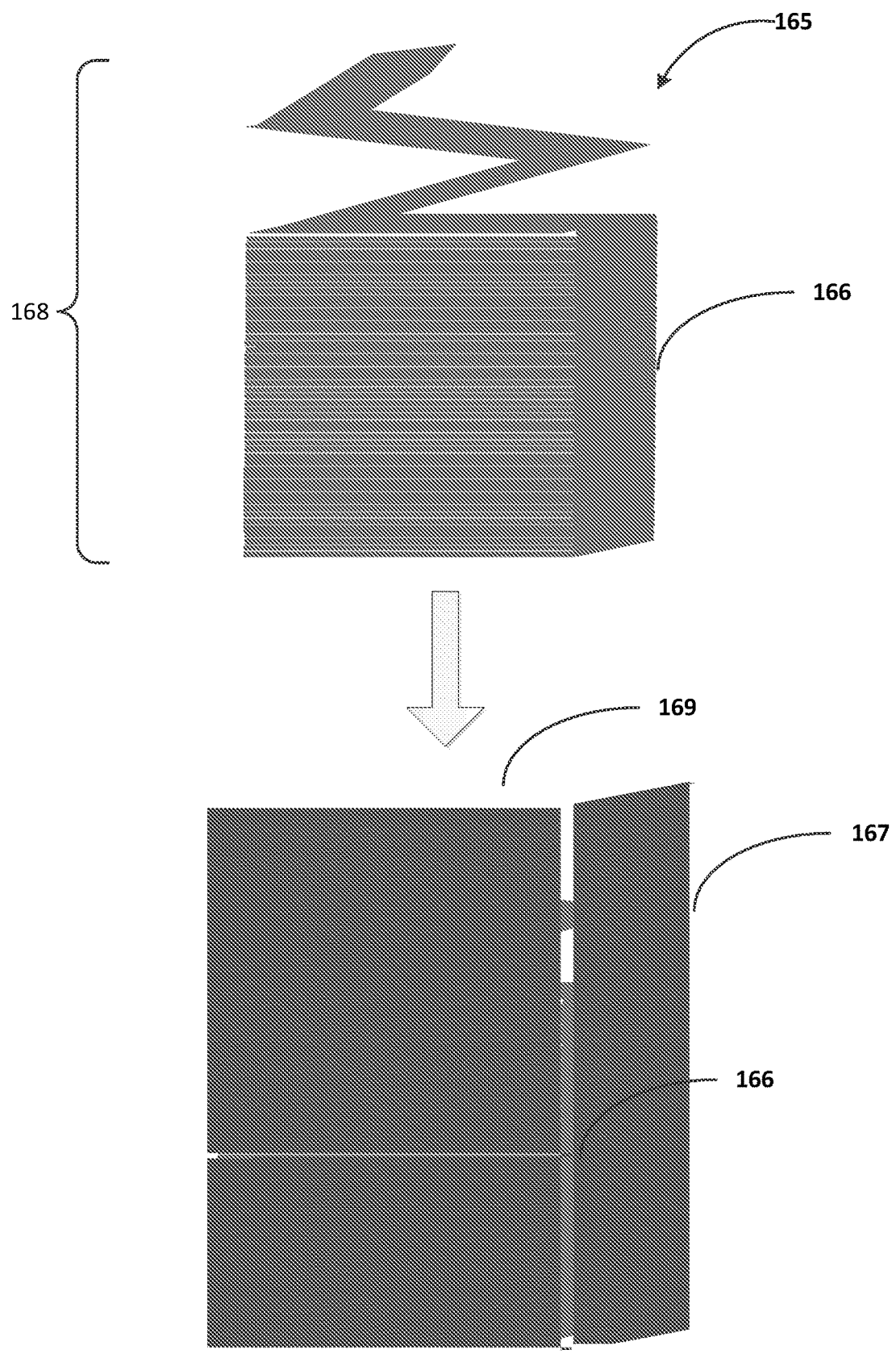
FIG. 6C illustrates a packaging arrangement 165 for packaging sectional warming blankets 166 in accordance with one or more example implementations and techniques described in this disclosure.

FIG. 6C illustrates a packaging arrangement 165 for packaging sectional warming blankets 166 in accordance with one or more example implementations and techniques described in this disclosure. As illustrated, a width of sectional warming blankets, such as warming blankets 150 as illustrated and described in FIG. 6B, are provided on a length of material, such as web material 160, and remain adjoined to each other along the length dimension of the material. In various examples the width of sectional warming blankets 166 provides a single sectional warming blanket across the width dimensions of sectional warming blankets 166, although in alternative examples more than one sectional warming blanket may be provided across a width dimension of the sectional warming blankets 166. The length of sectional warming blankets 166 may be folded as shown in FIG. 6C along each of a plurality of cutlines provided across the width dimension and between each of the sectional warming blankets 166 provide along the length dimension.

The folding of sectional warming blankets allows the length of sectional warming blankets 166 to be provided as a stack 168. The stack 168 may be packaged into a box or other container 167 for shipping to a customer. Container 167 may include an opening 169 that allows the stack 168 to extend through the opening to allow individual sectional warming blankets of the stack 168 to be dispensed from the container 167. For example, as a portion of stack 168 is pulled through opening 169, one or more of the sectional warming blankets 166 may be torn or otherwise separated from stack 168, and the separated sectional warming blanket or blankets further processed for use in providing patient warming to a patient.

Figure 7:
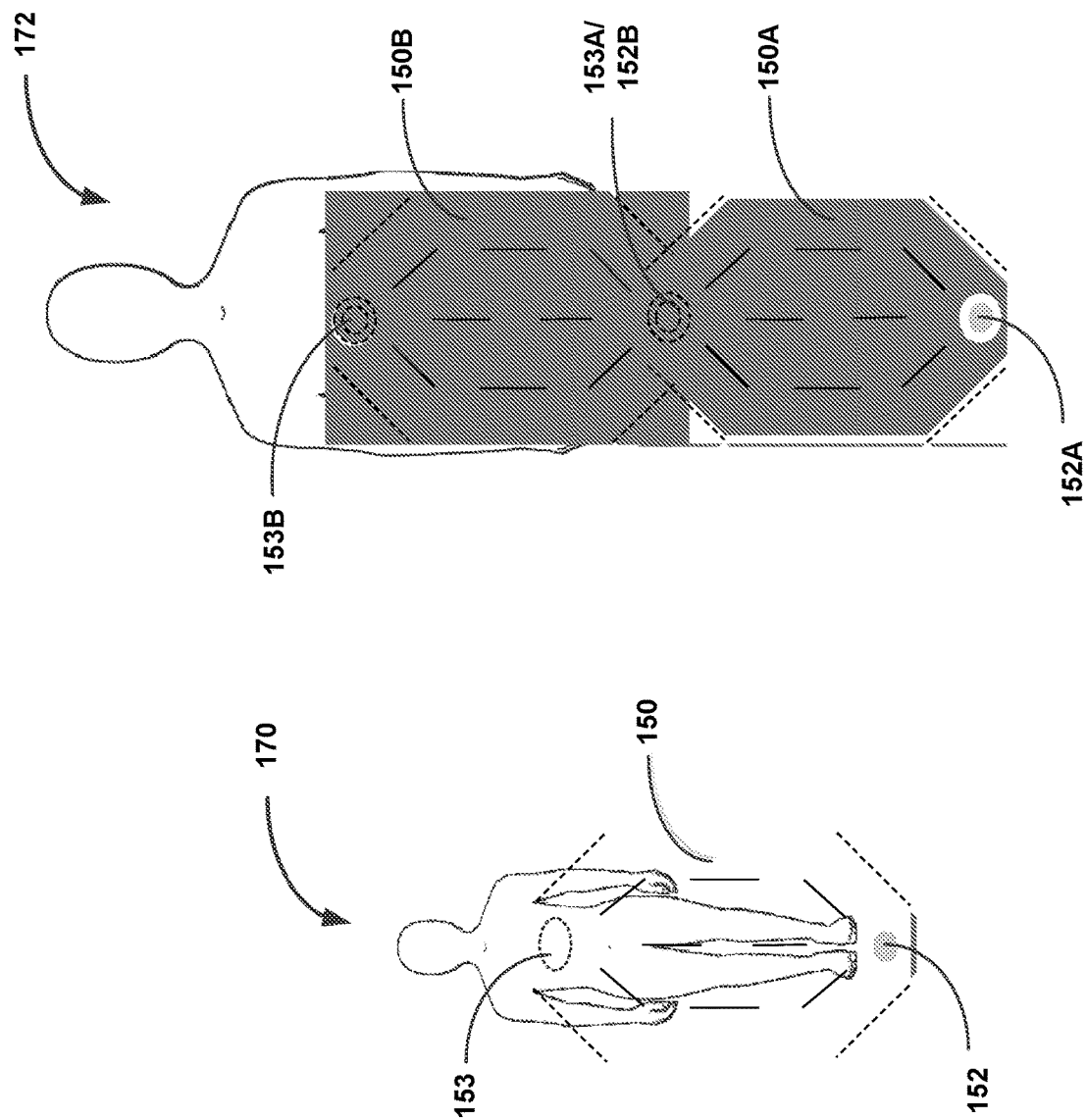
FIG. 7 illustrates use of sectional warming blankets on different size patients in accordance with one or more example implementations and techniques described in this disclosure.

FIG. 7 illustrates use of a sectional warming blanket on different size patients in accordance with one or more example implementations and techniques described in this disclosure. FIG. 7 illustrates use of a sectional warming blanket, such as sectional warming blankets 150 as illustrated and described with respect to FIGS. 6A-C, for warming of different size patients. In FIG. 7, patient 170 is an illustrative representation of a young or pediatric patient, and larger patient 172 is an illustrative representation of a patient who is larger than patient 170, where patient 172 may be an adult patient. As illustrated, a single warming blanket 150 may be adequate to provide the patient warming needed for patient 170 based on the size of patient 170 and the dimensions provided by warming blanket 150. In such examples, a flow of warmed air may be provided an inlet 152, and then distributed to the portions of patient 170 covered by sectional warming blanket 150. In addition, because only the single sectional warming blanket is being used in the warming of patient 170, opening 153 may remain sealed, or is not punched open as described above, so that the air flow provided to inlet 152 is distributed throughout and through the bottom layer of the sectional warming blanket instead of flowing out opening 153.

In contrast, due to the larger size of patient 172, a single one of the sectional warming blankets 150 may not be of adequate dimensions to cover and provide a proper level of patient warming for patient 172. As shown in FIG. 7, a multi-sectional warming blanket is arranged by coupling a first sectional warming blanket 150A to a second sectional warming blanket 150B. The opening 153A of sectional warming blanket 150A is coupled to inlet 152B of sectional warming blanket, for example using a coupling device or any other coupling technique described in this disclosure or any equivalent thereof, to provide a passageway for a flow of air from sectional warming blanket 150A to sectional warming blanket 150B. The inlet 152A of sectional warming blanket 150A is left open to allow coupled to a source of a flow of air, and the opening 153B of sectional warming blanket 150B remains sealed or is not punched open, in order to maintain the inflation of both sectional warming blankets 150A and 150B. The coupled sectional warming blankets 150A and 150B are arranged so that the longitudinal dimensions of the sectional warming blankets are aligned, extending the overall length of the multi-sectional warming blanket configuration to provide warming for patient 172.

Thus, as illustrated by the examples of FIG. 7, a same sectional warming blanket, such as sectional warming blanket 150, may be used as a single unit or coupled to other sectional warming blanket(s) to form a multi-sectional warming blanket, and thus allowing a same type and size of a sectional warming blanket to be utilized for a variety of different size patients. This feature may allow an institution, such as a hospital or a medical clinic, to reduce or eliminate the total number of different sizes and dimension of warming blankets the intuition needs in order to provide the patient warming functions required by different size patients being serviced by the institution. The capability to provide the patient warming functions using a standardized sectional warming blanket that may be easily coupled and arranged to form a variety of multi-sectional warming blanket configurations may reduce cost and save time with respect to ordering, tracking, and stocking of warming blankets due for example to a reduced need to have on hand a number of different sizes and/or types of warming blankets.

Figure 8:
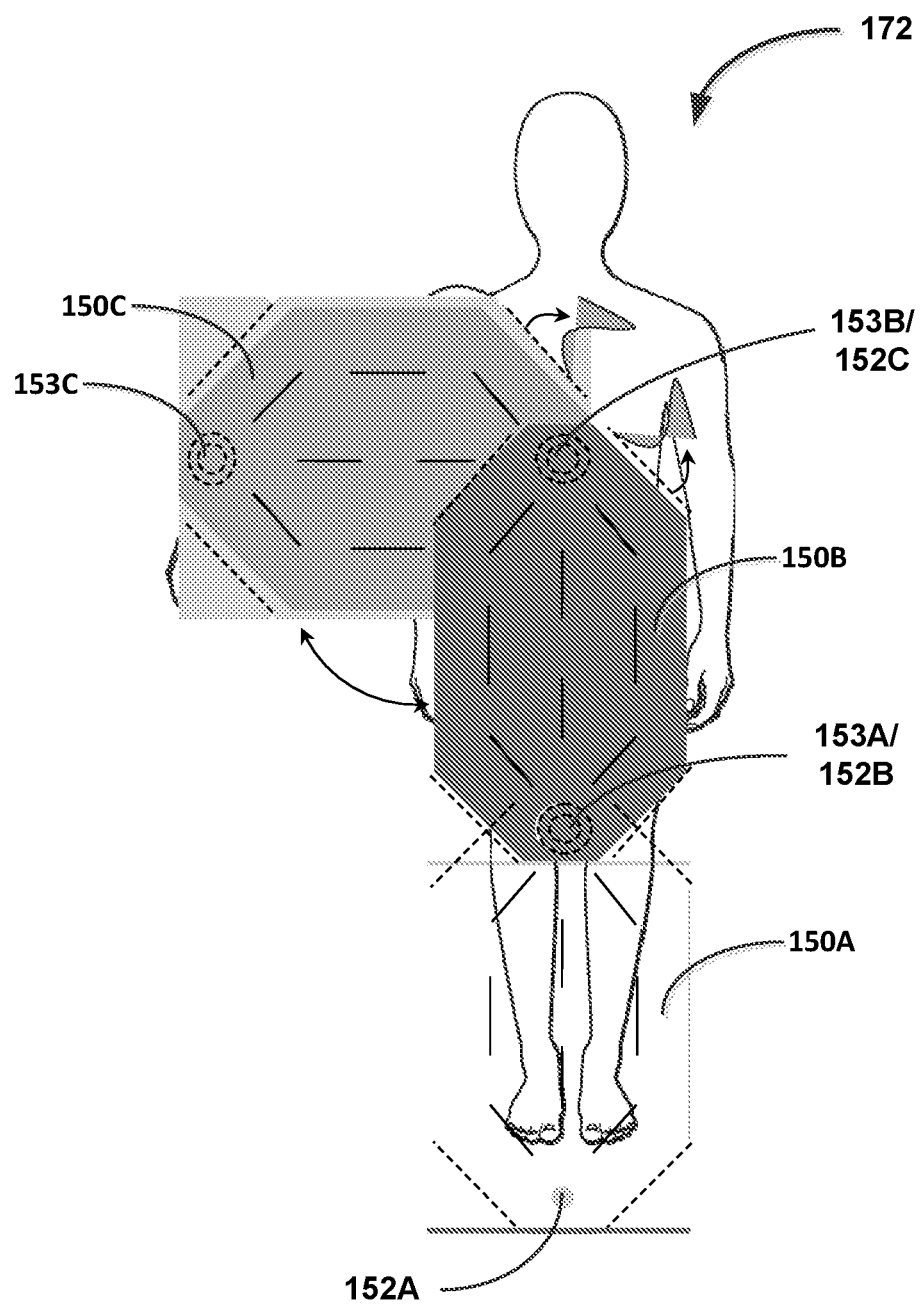
FIG. 8 illustrates use of sectional warming blankets to configure a multi-sectional warming blanket having a non-linear arrangement in accordance with one or more example implementations and techniques described in this disclosure.

FIG. 8 illustrates use of a sectional warming blanket used to configure a multi-sectional warming blanket having a non-linear arrangement in accordance with one or more example implementations and techniques described in this disclosure. In FIG. 8, illustrative adult patient 172 is being covered by a multi-sectional warming blanket comprising three sectional warming blankets 150A, 150B, and 150C. Sectional warming blanket 150A includes inlet 152A configured to receive a flow of air. Opening 153A of sectional warming blanket 150A is coupled to inlet 152B of sectional warming blanket 150B. Opening 153B of sectional warming blanket 150B is coupled to inlet 152C of sectional warming blanket 150C. Opening 153C of sectional warming blanket 153C remains sealed or is not punched open.

Sectional warming blanket 150A cover the feet and lower legs of patient 172. Sectional warming blanket 150B covers the upper legs and lower torso of patient 172, is longitudinally aligned with sectional warming blanket 150A, and is coupled to receive a flow of air from sectional warming blanket 150A. Sectional warming blanket 150C covers an arm (e.g., the left arm) and a portion of the torso of patient 172, is aligned at substantially a right angle relative to sectional warming blanket 150A and 150B, and is coupled to receive a flow of air from sectional warming blanket 150B. The capability to adjust the alignments of sectional warming blankets 150A-C relative to each other, including the capability to rotate the coupling between sectional warming blankets 150B and 150C to allow for a 90-degree orientation between the longitudinal dimensions of these warming blankets, provides the capability to configure a multi-sectional warming blanket, such as the one illustrated in FIG. 8, using a single type and size of sectional warming blanket. The coupling of sectional warming blankets 150A-C is not limited to any particular coupling device or coupling technique, and may include for example using a coupling device or any other coupling technique described in this disclosure or any equivalent thereof.

Thus, as illustrated by the example of FIG. 8, a same sectional warming blanket, such as sectional warming blanket 150, may be used to configure a multi-sectional warming blanket having a non-linear arrangement. Again, this feature may allow an institution, such as a hospital or a medical clinic, to reduce or eliminate the total number of different sizes and types of warming blankets the intuition needs to have available in order to provide the patient warming functions required by different size patients being services by the institution. As described above, this feature may reduce cost and save time with respect to ordering, tracking, and stocking warming blankets due to a reduced need to have on hand a number of different sizes and/or types of warming blankets.

Figure 9:
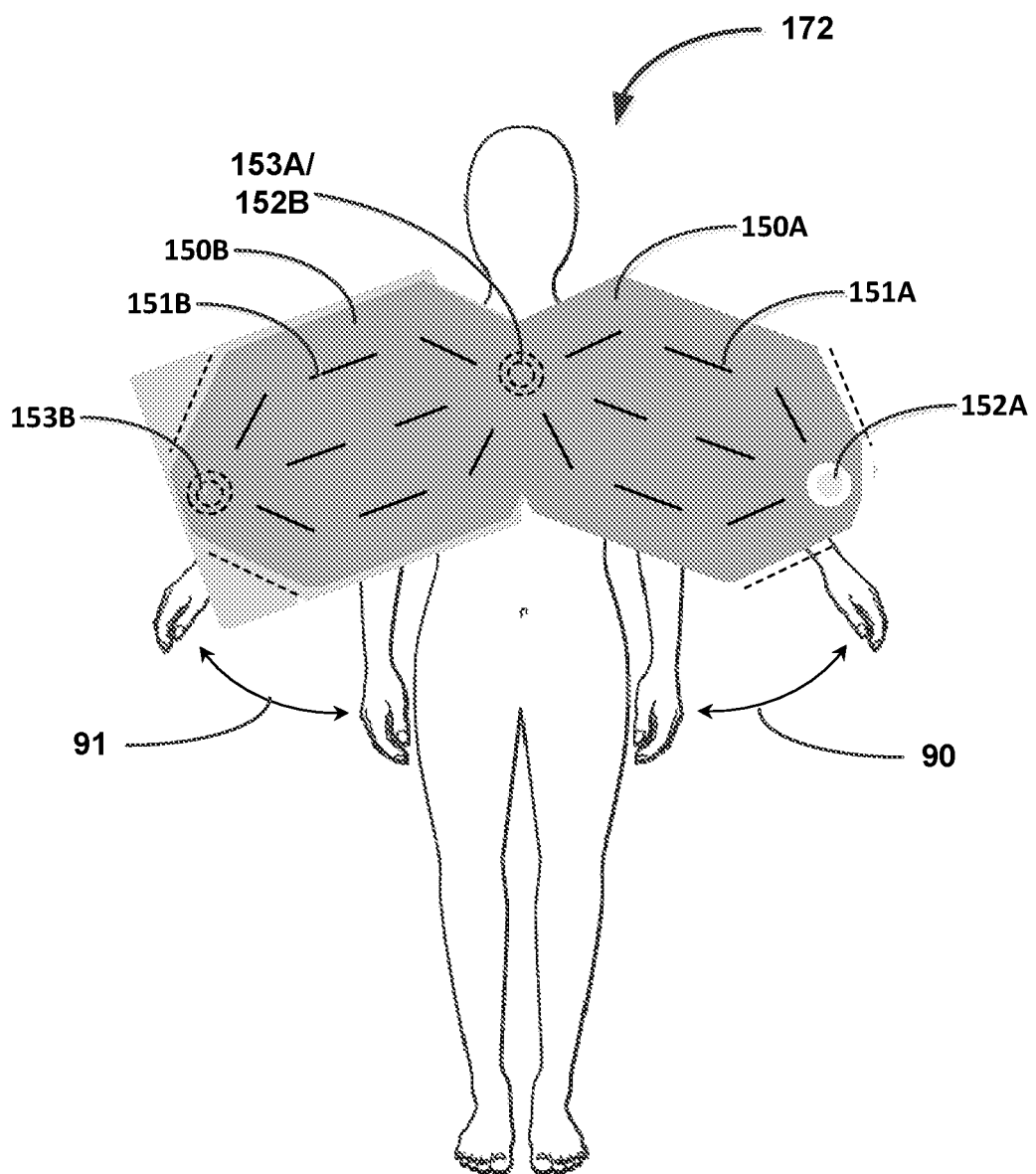
FIG. 9 illustrates use of sectional warming blankets to configure another version of a multi-sectional warming blanket having a movable, non-linear arrangement in accordance with one or more example implementations and techniques described in this disclosure.

FIG. 9 illustrates use of sectional warming blankets to configure another multi-sectional warming blanket having a movable, non-linear arrangement in accordance with one or more example implementations and techniques described in this disclosure. In FIG. 9, illustrative adult patient 172 is being covered by a multi-sectional warming blanket comprising two sectional warming blankets 150A, and 150B. Sectional warming blanket 150A includes inlet 152A configured to receive a flow of air. Opening 153A of sectional warming blanket 150A is coupled to inlet 152B of sectional warming blanket 150B. Opening 153B of sectional warming blanket 150B remains sealed or is not punched open. Sectional warming blanket 150A covers one arm and a portion of the upper torso of patient 172. Sectional warming blanket 150B covers one arm and another portion of the upper torso of patient 172.

The coupling 153A/152B provides a rotatable sealing coupling that allows the relative angle of alignment of the longitudinal dimensions of blankets 150A and 150B to be configured and changed from one angle to a different angle, as illustratively indicated by arrows 90 and 91. The ability to adjust this angle may be useful and/or required when certain procedures are performed on patient 172 that require movement and repositioning of the arms of the patient relative to the body. The coupling of sectional warming blankets 150A and 150B is not limited to any particular coupling device or coupling technique, and may include for example using a coupling device or any other coupling technique described in this disclosure or any equivalent thereof. The capability to provide this flexibility with respect to covering various arm angles using a pair of standardized sectional warming blankets to construct a multi-sectional warming blanket may provide any and all of the benefits as described above with respect to FIGS. 7 and 8.

Figure 10:
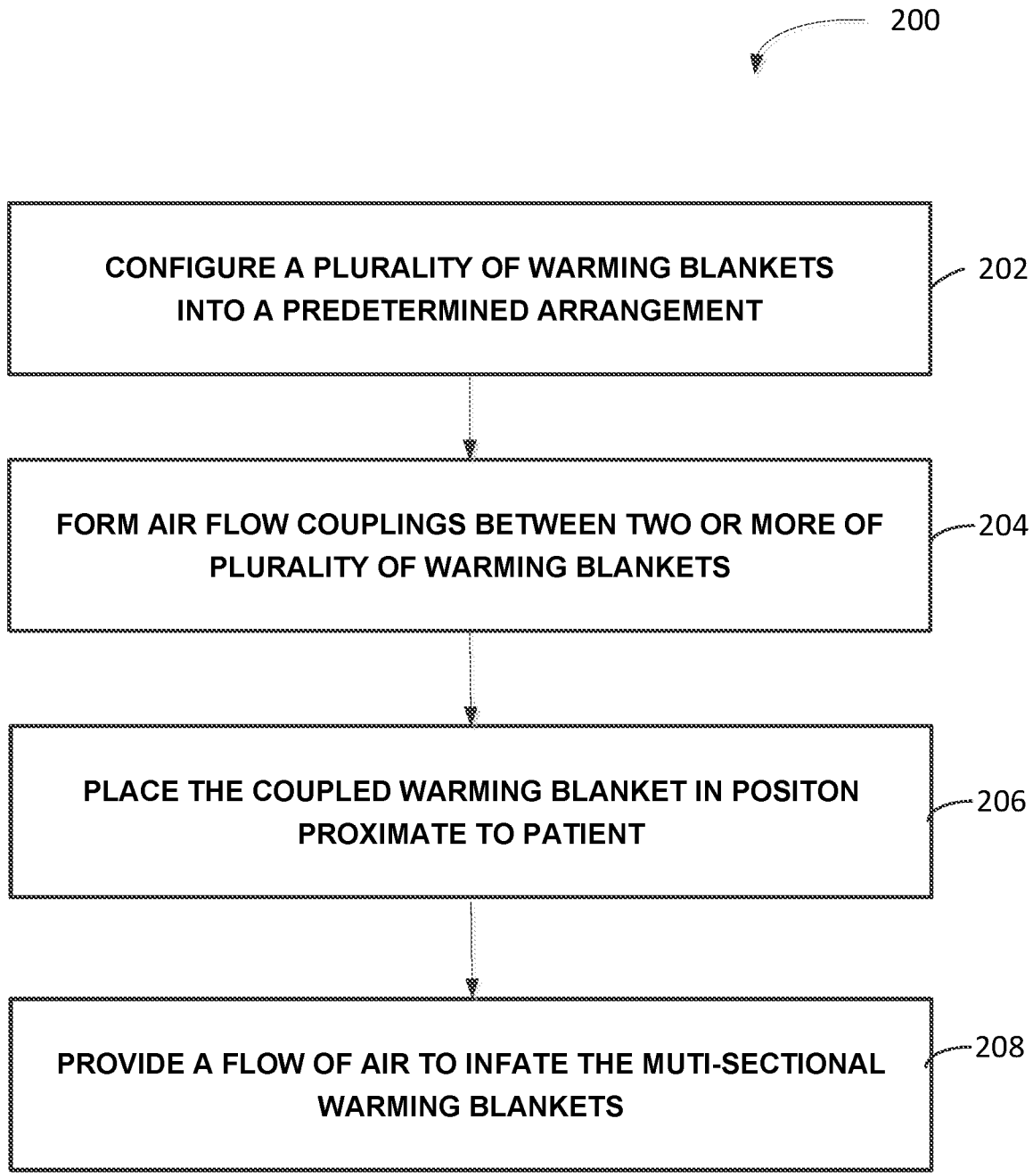
FIG. 10 is a flowchart illustrative of a method in accordance with one or more example implementations and techniques described in this disclosure.

FIG. 10 is a flowchart illustrative of a method 200 in accordance with one or more example implementations and techniques described in this disclosure. Method 200 is described with respect to multi-sectional warming blanket illustrated and described with respect to FIG. 8. However, examples of method 200 are not limited to the example illustrated in FIG. 8, and may be applicable to other multi-sectional blanket systems such as the multi-sectional blanket systems illustrated in FIG. 2, FIG. 3, FIGS. 4A-4D, FIG. 5, FIG. 7, and FIG. 9, and variations thereof. As illustrated in FIG. 10, method 200 includes arranging a plurality of warming blankets 150A, 150B, 150C into a predetermined arrangement (block 202). In various examples, the predetermined arrangement is an arrangement specific to a designated patient position in patient treatment procedure. The patient treatment procedure may or may not be a surgical procedure.

As an illustrative example, sectional warming blanket 150A is positioned so that a longitudinal axis of warming blanket 150A aligns with a longitudinal axis of sectional warming blanket 150B, and inlet 152A is at an end of sectional warming blanket 150A positioned opposite warming blanket 150B, wherein opening 153A of warming blanket 150A is placed over and covers an end of sectional warming blanket 150B including inlet 152B. Sectional warming blanket 150C is positioned so that a longitudinal axis of sectional warming blanket 150C forms a right angle to the longitudinal axes of sectional warming blankets 150A and 150B. An end of sectional warming blanket 150B having opening 153B is placed over an end of sectional warming blanket 150B having inlet 152C.

Method 200 includes forming air flow couplings between one or more of the plurality of warming blankets (block 204). In various examples as illustrated in FIG. 8, forming air flow couplings includes forming an air flow coupling 153A/152B by coupling the opening 153A of sectional warming blanket 150A to the inlet 152B of sectional warming blanket 150B, and forming an air flow coupling 153B/152C by coupling the opening 153B of sectional warming blanket 150B to the inlet 152C of sectional warming blanket 150C. Forming the air flow couplings in some examples includes coupling the sectional warming blankets 150A-C to maintain a same configuration of the plurality of sectional warming blankets as was provided at block 202. In some examples, adjustment to the configuration of the plurality of sectional warming blankets after forming the air flow coupling may be made, for example by rotation of one or both of the sectional warming blankets around the coupled formed as the air flow coupling between these particular sectional warming blankets. Forming the air flow coupling is not limited to any particular device or technique for forming the air flow coupling, and may include use of a coupling device and/or adhesives as described in this disclosure, or any equivalents thereof. Coupling the sectional warming blankets to form the air flow couplings may include any device or technique that allow a flow of air provided to a first one of the sectional warming blankets, such as a flow of air provided at inlet 152A of sectional warming blanket 150A to be distributed to the passageways of each of the sectional warming blanket 150A, 150B, and 150C.

Method 200 may then proceed to placing the configuration of sectional warming blankets in position proximate to the patient 172 (block 206). In various examples, this step may be performed before forming the air flow coupling between the sectional warming blankets. In either examples, once sectional warming blankets 150A-C are coupled by the air flow coupling, the configuration may be referred to as a multi-sectional warming blanket.

Method 200 may further include providing a flow of air to inflate the multi-sectional warming blanket (block 208). In some examples, providing a flow of air to the multi-sectional warming blanket includes coupling an inlet, such as inlet 152A of warming blanket 150A, to a source of a flow of air. The source of a flow of air may provide a flow of warmed air in some examples to provide warming of patient 172, and may provide ambient or cooled air in other examples to patient 172.

Method 200 is not limited using a particular number of warming blankets to for a multi-sectional warming blanket, and may include two or more warming blankets coupled together to form a multi-sectional warming blanket. In addition, the particular configuration and arrangement of the sectional warming blankets is not limited to any particular arrangement or angles of configuration relative to the different warming blankets used to configure the multi-sectional warming blanket, and as describe above, may be arranged to meet the requirement of a specific procedure and/or a specific patent position required as part of a procedure to be performed on the patient.

Figure 11:
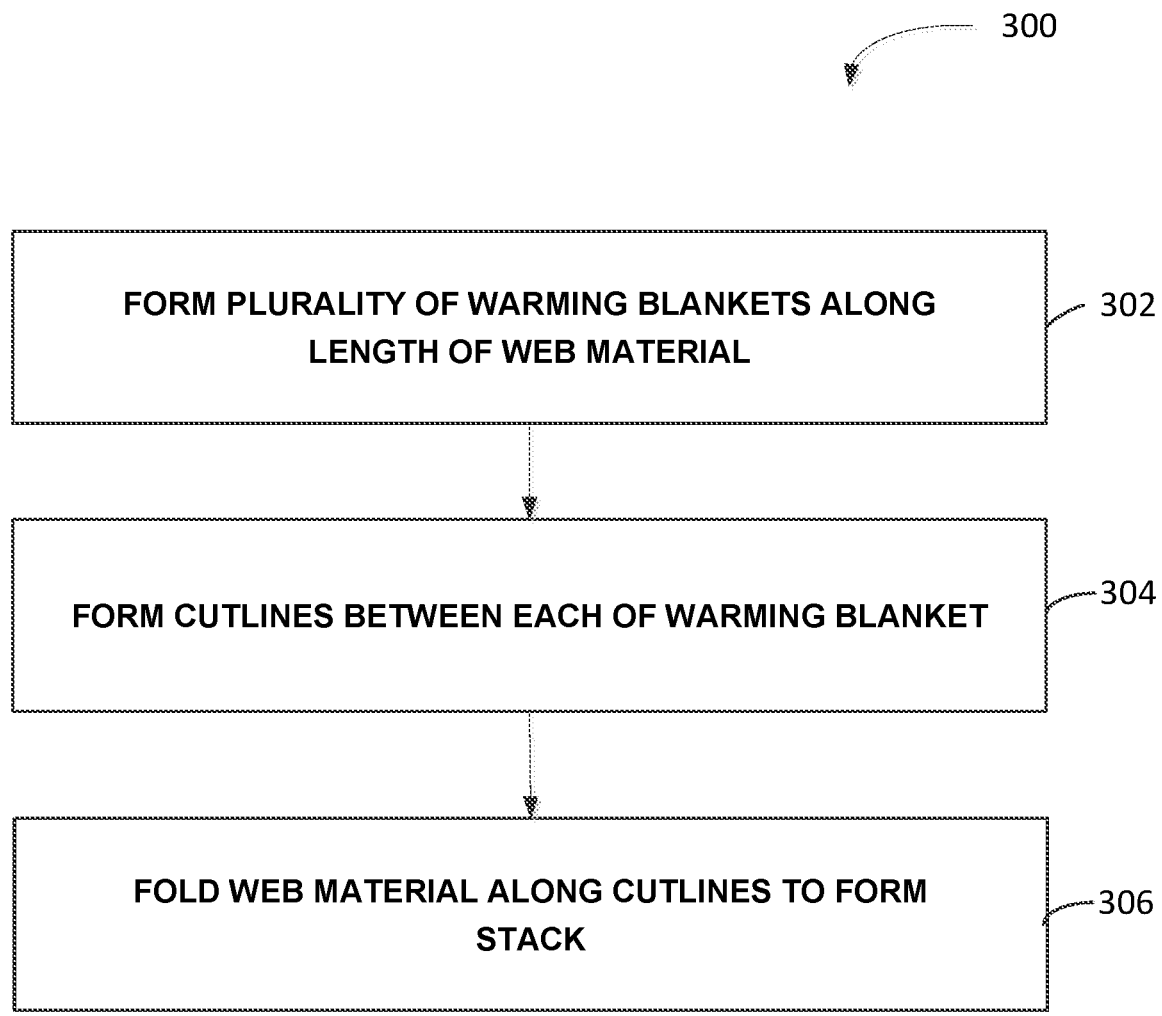
FIG. 11 is a flowchart illustrative of another method in accordance with one or more example implementations and techniques described in this disclosure.

FIG. 11 is a flowchart illustrative of a method 300 in accordance with one or more example implementations and techniques described in this disclosure. Method 300 is described with respect to multi-sectional warming blanket formed on a web material 160 as illustrated and described with respect to FIGS. 6A-C, but examples of method 300 are not limited to the examples illustrated and described with respect to FIG. 6A-C. As illustrated in FIG. 11, method 300 includes forming a plurality of sectional warming blankets 150 along a length of web material 160 (block 302). Method 300 include forming a set of cutlines, each cutline provided across a width dimension of the web material 160 and located between two of the warming blankets along a longitudinal dimension of the web material (block 304). In some examples, the width dimension of the web material includes a single row of warming blankets 150, and in other examples the width dimension of the web material includes two or row of warming blankets 150. In examples where there are two or more rows of warming blankets provided across a width dimension of the web material 160, a separation line 163 may be formed between the rows to allow conversion of each row of warming blankets to be separated from the adjacent row or rows.

Method 300 includes folding the web material 160, including the sectional warming blankets along the set of cutlines to more an accordion shaped stack 168 of warming blankets. Folding of the warming blankets to form a stack 168 may further includes placing the stack 168 into a container 167 for shipment to a customer and to allow dispensing of the sectional warming blankets by the customer.

Figure 12A:
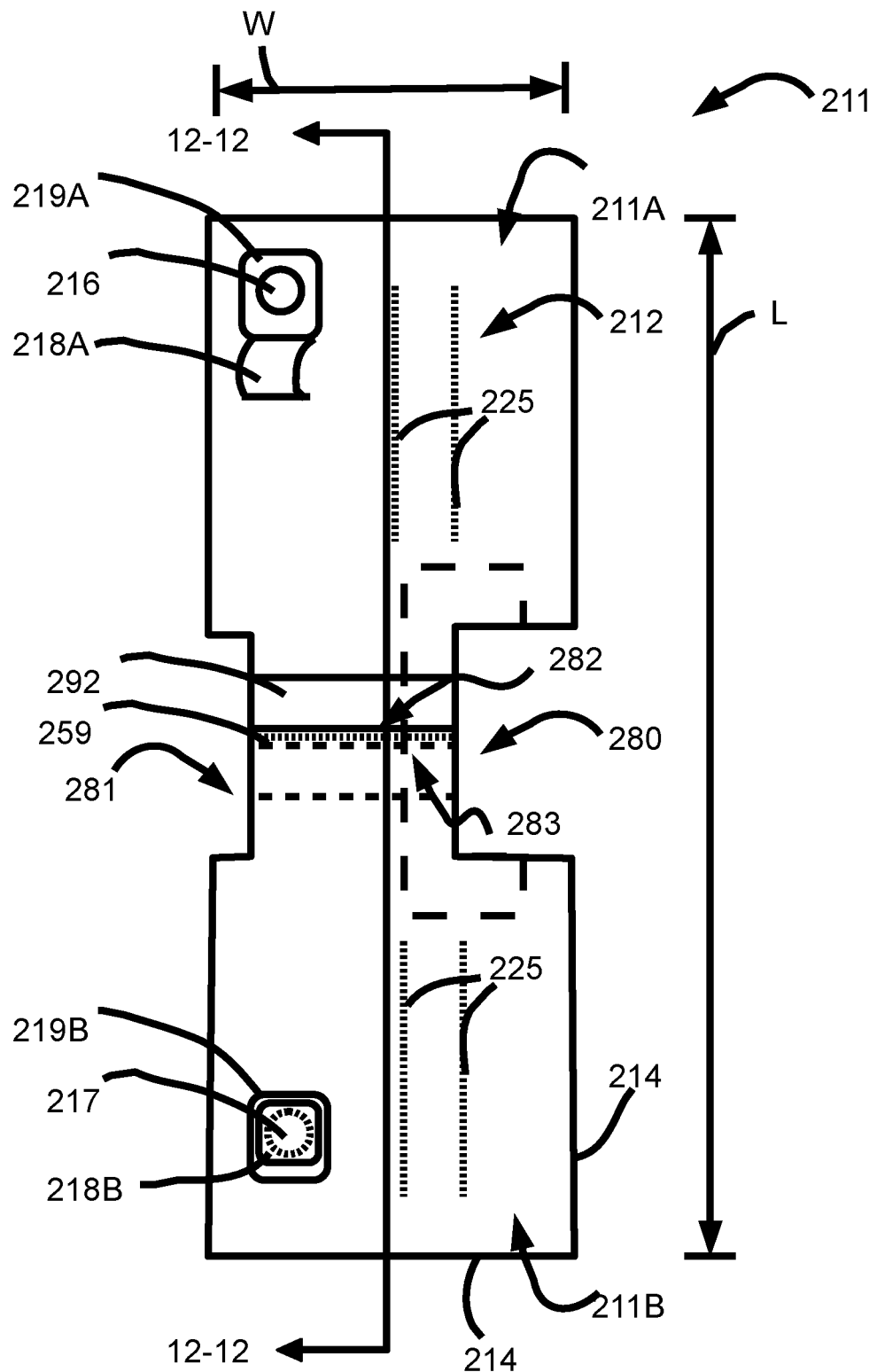
FIG. 12A illustrates a top elevational view of another embodiment of a warming blanket in accordance with one or more example implementations and techniques described in this disclosure.
Figure 12B:
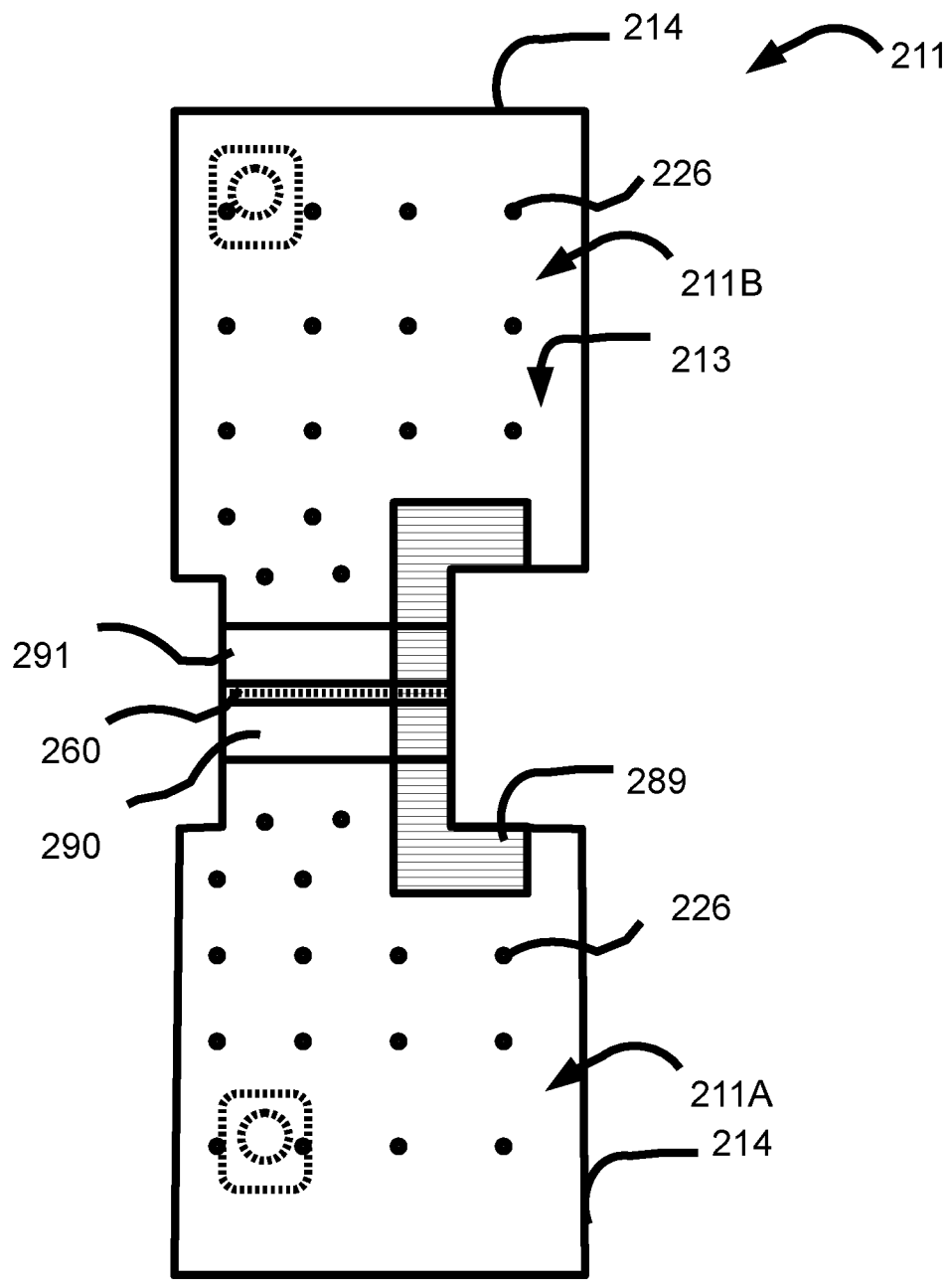
FIG. 12B illustrates an bottom elevational view of the warming blanket of FIG. 12A in accordance with one or more example implementations and techniques described in this disclosure.
Figure 12C:
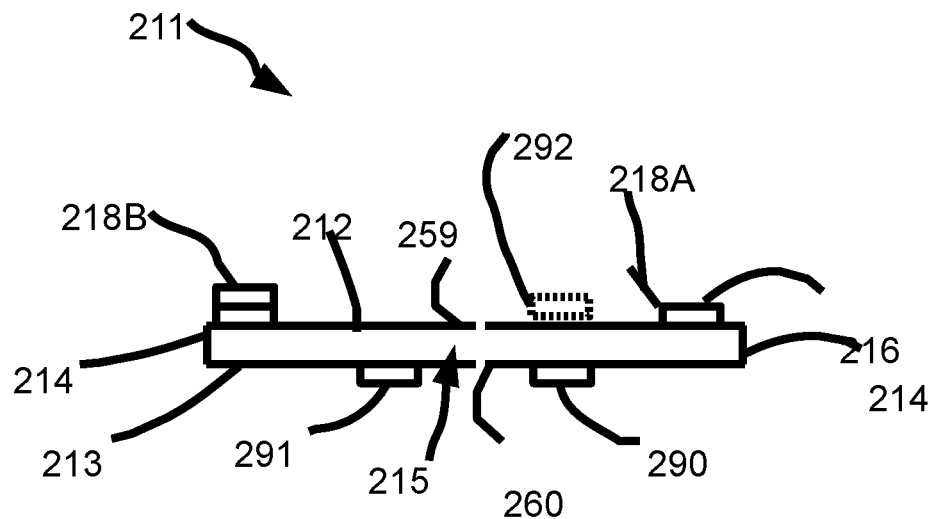
FIG. 12C illustrates a cross-sectional view of the warming blanket of FIGS. 12A-12B taken along the lines of 12-12 in accordance with one or more example implementations and techniques described in this disclosure.

FIG. 12A-12C illustrate an exemplary embodiment of a warming blanket 211. Aspects of the warming blanket 211 can be similar to blanket 11 in FIGS. 1-4, or blanket 150 in FIGS. 6-9.

The warming blanket 211 can have a structure comprising a first layer of material 213 and a second layer of material 212. In at least one embodiment, the first layer 213 and second layer 212 are constructed similarly to the bottom layer 13 and the upper layer 12 of warming blanket 11 in FIG. 1. For example, the first layer 213 of material can form a bottom layer of the warming blanket 211. The bottom layer 213 is configured to allow a profusion of air to pass through the bottom layer through perforations 226 formed therewith or through permeation of the bottom layer 213 itself (i.e., through a non-woven structure).

The second layer 212 of material forms an upper layer of the warming blanket 211. The upper layer is coupled (e.g., heat sealed) to the bottom layer 213 around a periphery 214 of the bottom layer 213 to form an initial shape of the warming blanket 211. An interior space 215 formed between the first layer 213 of material and the second layer 212 of material can be formed. The interior space 215 can also be referred to interchangeably as a plurality of interconnected air passageways. The interconnected air passageways 215 can be further defined by a plurality of seals 225 formed between the upper layer 212 and the bottom layer 213 within the area defined by the periphery 214. As shown in FIG. 12A, the seals 225 are linear seals oriented longitudinally along length L. Other configurations, such as spot/point seals between the layers 213 and 212 within the area defined by the periphery 214 may be used to create custom air passageways.

The periphery 214 of the warming blanket 211 is formed by one or more substantially air-impermeable seals. The air-impermeable seals can be formed by bonding the first layer 213 with the second layer 212. Air can be provided into the interior space 215 and prevented from passing through the periphery 214 by the air-impermeable seals. In at least one embodiment, the periphery 214 can be hourglass-shaped meaning that at least one indented portion (e.g., 280, 281) exists in the middle of the blanket 211. The indented portion 280 or 281 can conform to the neck region of a patient and allow easier handling of the blanket 211. The blanket 211 can have a particular longitudinal dimension L and width dimension W. The longitudinal dimension L can be a longer dimension than the width dimension W.

The blanket 211 can have at least one inlet 216 which may be configured according to inlet 16 of FIG. 1. The inlet 216 is configured to receive a flow of air from a source 240 and to provide the flow of air to the interconnected air passageways 215. In at least one embodiment, the inlet 216 can include a seal 218A that is configured to maintain an air seal when in place over the passageway. The seal 218A can be formed from the second layer 212. A connection port from an air source can puncture the seal 218A and provide and air flow. If the connection port is removed, then the inlet 216 will remain exposed. As shown, the seal 218A is removable to expose the inlet. In at least one embodiment, the inlet 216 can be surrounded by a reinforcing collar 219A. In at least one embodiment, the reinforcing collar 219A can be above the layer 212.

As used herein, an inlet 216 is defined by the ability to receive a flow of air. The blanket 211 can have an inlet 217. If the seal 218B is removed or punctured, and a positive air pressure can be applied through the inlet 217. As used herein, an inlet 217 can refer to an area configured to receive an air hose or an air flow. An inlet does not have to be receiving air flow from a source. An opening can be similar in construction to an inlet but is configured to discharge air to another inlet. An inlet 217 with a seal 218B covering the inlet 217 does not receive air. As shown, the inlet 217 is located on the upper layer 212 but can also be on the bottom layer 213. The inlet 217 can include a seal 218B configured to seal an inlet coupled to the interconnected air passageways 215. For example, the seal 218B is configured to maintain an air seal when in place over the passageway and when the blanket 211 is receiving an air flow. In at least one embodiment, the inlet 217 can be formed by a reinforcing collar 219B.

The warming blanket 211 can also have at least one cutline 259 located within the area bordered by the periphery. The cutline 259 can be a weakened portion of a layer of the blanket 211 such that any manual shear force will separate the warming blanket 211 into at least two sections (e.g., sections 211A and 211B) along the cutline 259. In at least one embodiment, the cutline 259 can include a perforation whereby a marginal amount of air passes through layer 212.

More than one cutline (i.e., a plurality of cutlines) can exist in the warming blanket 211. For example, the first layer 213 can have a first cutline 260 and the second layer 212 can have a second cutline 259. In at least one embodiment, the cutlines 259, 260 divide the warming blanket 211 into a first section 211A and a second section 211B. The first and second sections 211A, 211B can be configured to be used independently from one another.

In at least one embodiment, the warming blanket 211 can have at least one adhesive area 289. The adhesive area 289 can be disposed on the patient facing side of the first layer 213 and be configured to secure the warming blanket 211 to the patient. In at least one embodiment, the adhesive area 289 is a pressure sensitive adhesive but the adhesive area 289 can also be an area of increased friction made from, e.g., rubber, or textured silicone. The adhesive area 289 may be covered with a release liner (not shown) for ease of transport. As shown in FIG. 12B, the adhesive area 289 is shown as a u-shape. The cutline 259 can bisect the adhesive area 289 and form two portions.

In at least one embodiment, the warming blanket 211 includes at least one bonding mechanism (e.g., 290, 291) disposed on a portion of the structure. A bonding mechanism can generally be configured to attach the first layer 213 to the second layer 212.

While not necessarily airtight, the bonding mechanism is configured to resist air flow leaving the blanket 211 such that the air passageways 215 remain inflated when exposed to an air flow. For example, the bonding mechanism can retard the outflow of air from the air passageways 215 such that a majority of a flow rate of air is directed out of the first layer 213 and not the area proximate to the cutline 259.

As shown in FIG. 12B, a plurality of bonding mechanisms are disposed on a portion of the structure. The bonding mechanism can be proximate to or adjacent to the cutline 259. The distance from the bonding mechanism to the cutline 259 can be sufficient to allow an edge formed from the cutline 259 exposed by shear to be folded over and attached to the bonding mechanism. Although shown on the outer surface of the blanket 211, the bonding mechanism can also be disposed on the inner surface of any of the layers 212 or 213. The bonding mechanism is configured to resist the air pressure from a source 240 and allowing the area 225 to inflate. Examples of bonding mechanisms can include adhesives, mechanical fasteners such as hook-and-loop, or even flaps. If an adhesive is used, then a release liner may also be used to cover the adhesive. If a multicomponent bonding mechanism is used (e.g., a hook-and-loop), then one part of the bonding mechanism can be disposed on a portion of the layer 213 while another portion is disposed on another portion (e.g., an inner or outer surface) of either the layer 213 or 212.

In at least one embodiment, the a plurality of bonding mechanisms (e.g., a first bonding mechanism 290 disposed on the first section 211A and a second bonding mechanism 291 disposed on the second section 211B) are disposed on the first layer 213. In some embodiments, it may be advantageous to have an optional third bonding mechanism 292 disposed on the second layer 212 for additional securement.

A fluid such as air can be introduced into the warming blanket 211 through an inlet 216. In some embodiments, a connection port (not pictured) can puncture the cover 218B and enter inlet 217.

Figure 13:
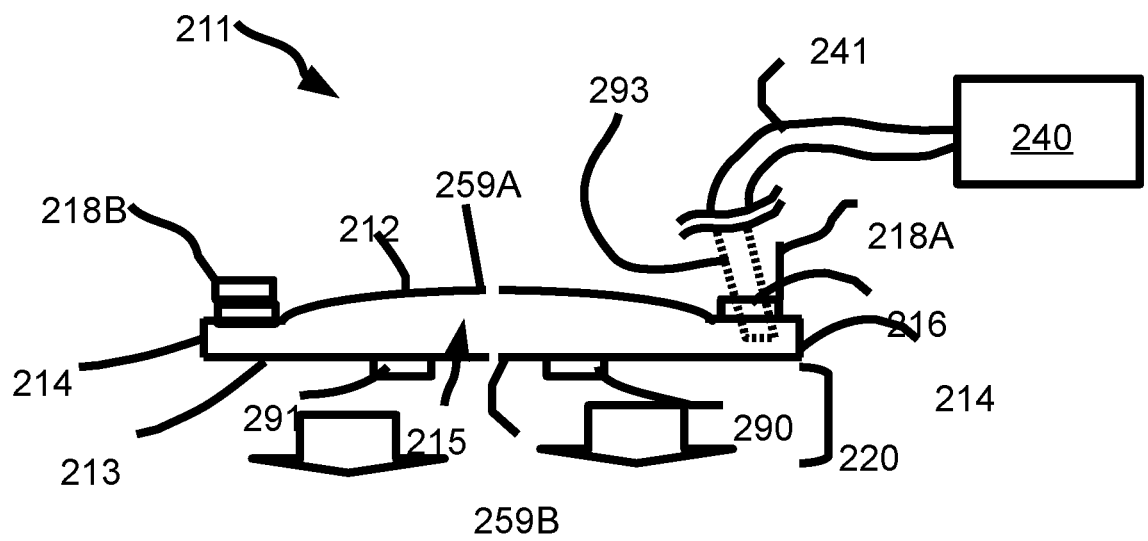
FIG. 13 illustrates a cross-sectional view of the warming blanket of FIGS. 12A-12C shown in an inflated state in accordance with one or more example implementations and techniques described in this disclosure.

FIG. 13 illustrates the warming blanket 211 in an inflated state. An air source 240 can provide a flow of air through a flexible hose 241 similar to source 40 and hose 41 found in FIG. 2. The source 40 provides air through the inlet 216 via a connection port 293. The connection port 293 can couple with a portion of the inlet 216 such as a reinforcing collar 219A. The source 240 can inflate the interconnected air passageways 215 of the blanket 211. Air can be output through the perforations formed from the first layer 213. The airflow is shown as arrows 220. The inflation of blanket 211 can be similar to that described in blanket 11 in FIG. 2 herein.

Figure 14A:
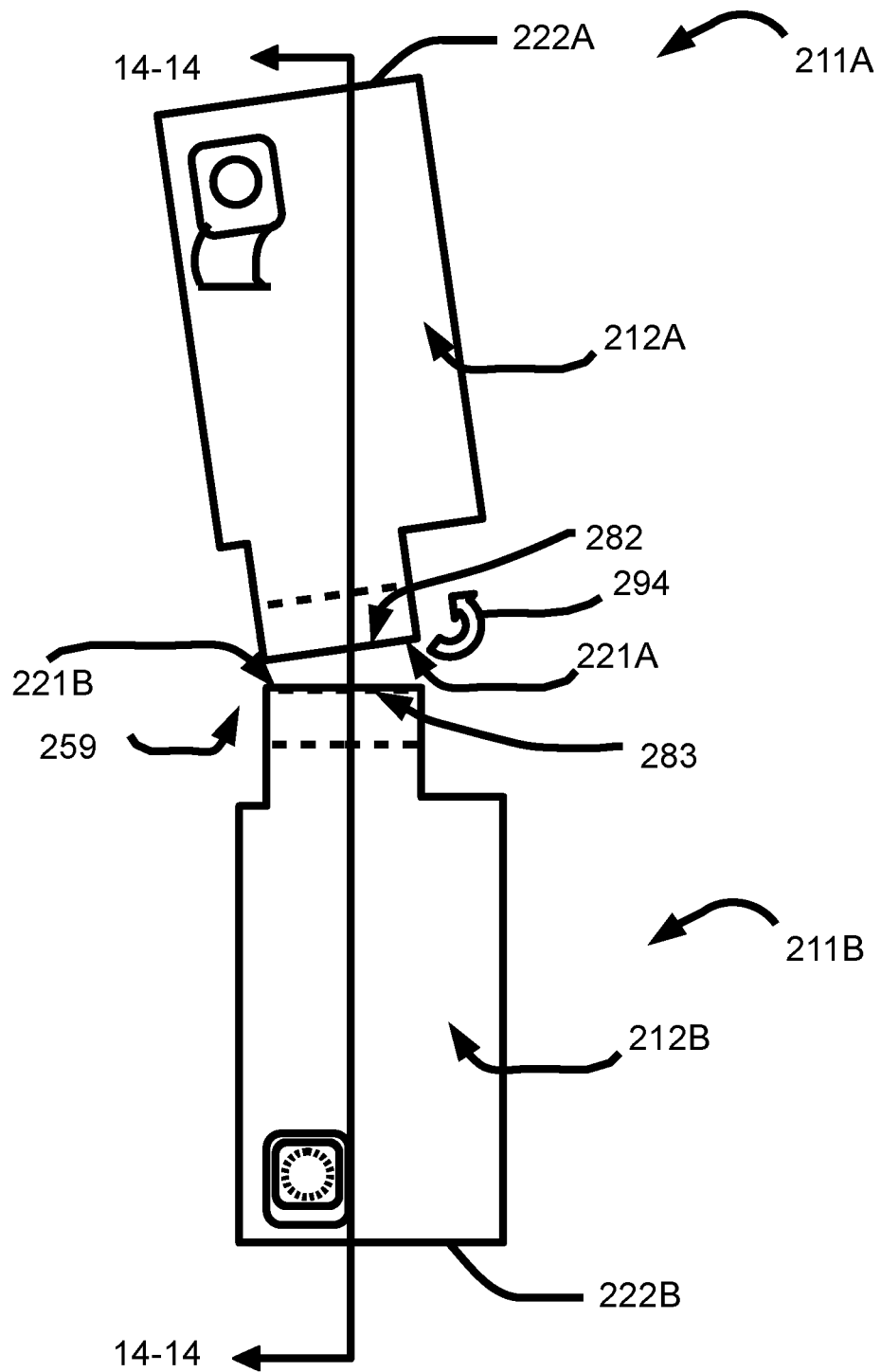
FIG. 14A illustrates a top elevational view of the warming blanket of FIGS. 12A-12C shown in two sections in accordance with one or more example implementations and techniques described in this disclosure.
Figure 14B:
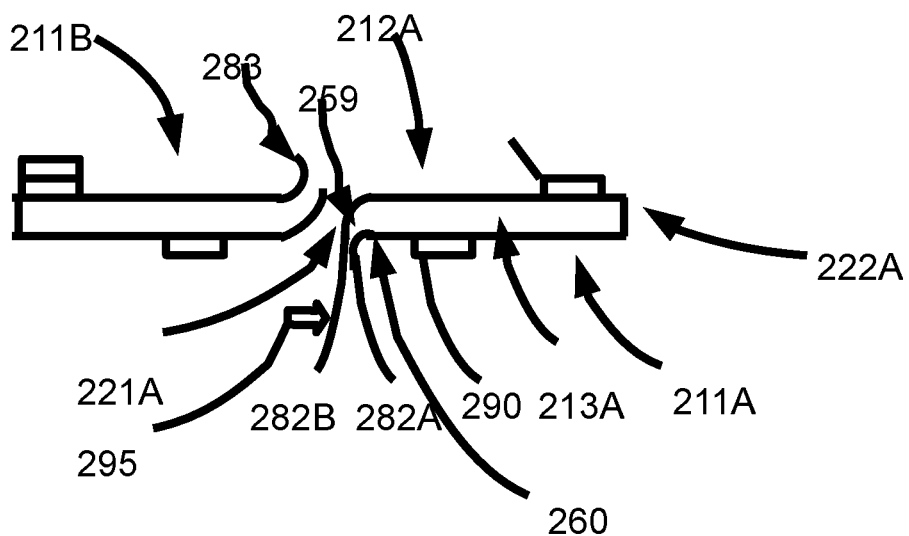
FIG. 14B illustrates a side cross-sectional view of the warming blanket of FIG. 14A taken along the lines of 14-14 in accordance with one or more example implementations and techniques described in this disclosure.

FIGS. 14A-14B illustrate a warming blanket 211 that separates into two independent sections (211A and 211B) along cutlines 259 and 260. A shear or some other tearing force can be applied as indicated by arrow 294.

The first section 211A can have an end 221A and end 222A and an edge portion 282. The edge portion 282 can be formed from forced tearing of the cutlines 259 and 260. The first section 211A can have a first layer 213A and second layer 212A. The cutline 260 on the first layer 213A can form a first edge 282A while the cutline 259 on the second layer 212A can form the second edge 282B. The edge 282A can be separated (i.e., not bonded) from edge 282B or layer 213A. In operation, the edges 282A and 282B can contact each other and be folded inward toward the end 222A according to the arrow 295.

Similarly, the second section 211B, can have an end 221B and end 222B. The second section 211B can have an edge portion 283. The section 211B can be similar in construction to section 211A.

Figure 15:
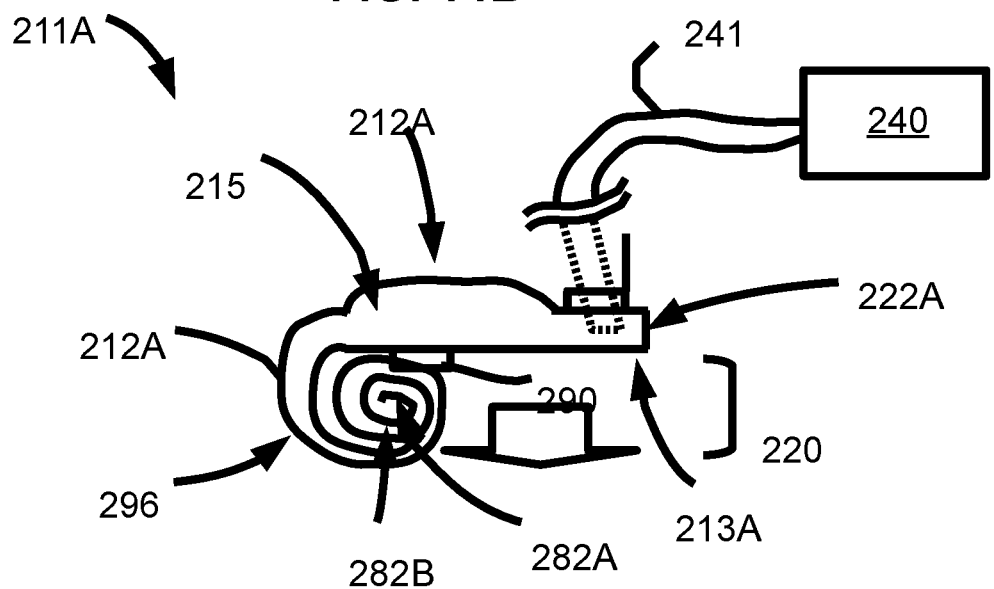
FIG. 15 illustrates a side cross-sectional view of one section of the warming blanket of FIGS. 14A-14B shown in an inflated state in accordance with one or more example implementations and techniques described in this disclosure.

FIG. 15 illustrates the first section 211A in a folded an inflated state. For example, layer 212A can contact layer 213A, specifically edge 282A can contact edge 282B prior to being rolled up or folded sufficient to retain air within the air passageway 215. The first section 211A can have the edge 282A/282B mechanically sealed to form a sealed portion 296. The sealed portion 296 can be sufficiently fluidically sealed such that air leakage from an area adjacent to the sealed portion 296 is less than the air leakage from the first layer 213A when air from an air source 240 is supplied through a hose 241.

In at least one embodiment, the sealed portion 296 can be formed from at least one bonding mechanism 290. For example, the sealed portion 296 can be formed from any portion of the distance from the bonding mechanism 290 to the edge 282A. In section 211A, a portion of the first layer 213A contacts another portion of the first layer 213A. An outer surface of the second layer 212A can contact the bonding mechanism 290. In at least one embodiment, the bonding mechanism 290 may be an adhesive fastener. Thus, one bonding mechanism 290 disposed on the first surface 213A may be effective to prevent the sealed portion 296 from releasing. The bonding mechanism can be a mechanical fastener such as a hook-and-loop fastener. If a hook-and-loop fastener is used, then the bonding mechanism 290 can be a hook or a loop and a third bonding mechanism (corresponding to a corresponding hook or loop) can be disposed on either layer 213A or 212A between the bonding mechanism 290 and edge 282 (not pictured).

In at least one embodiment, the section 211A can be inflated by the air source 240 and through hose 241 in a similar manner to that described herein. Pressurized air can inflate the air passageways 215 and the pressurized air can be output through the layer 213A as shown by arrows 220.

Figure 16A:
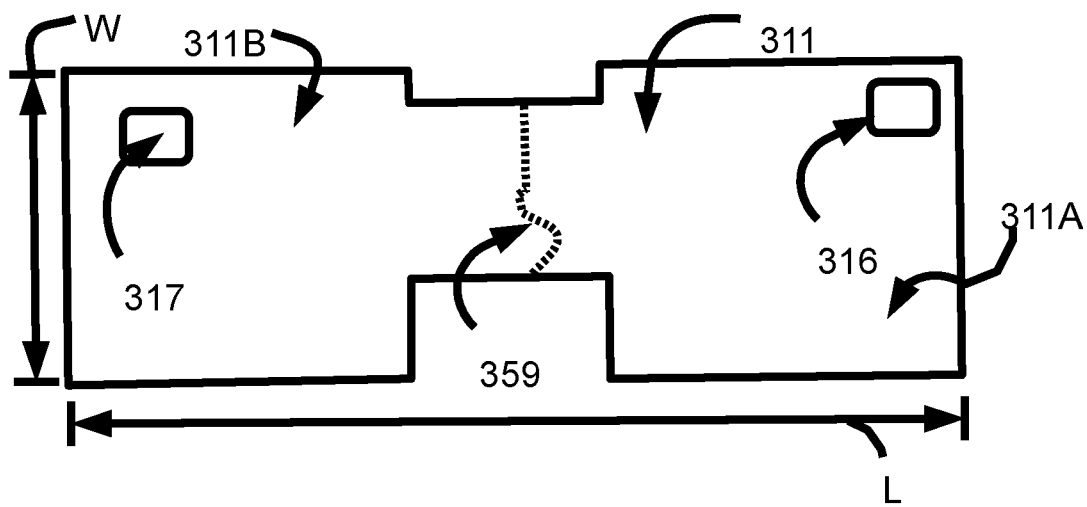
FIGS. 16A-16D illustrates a top elevational view of various embodiments of a warming blanket in accordance with one or more example implementations and techniques described in this disclosure.
Figure 16B:
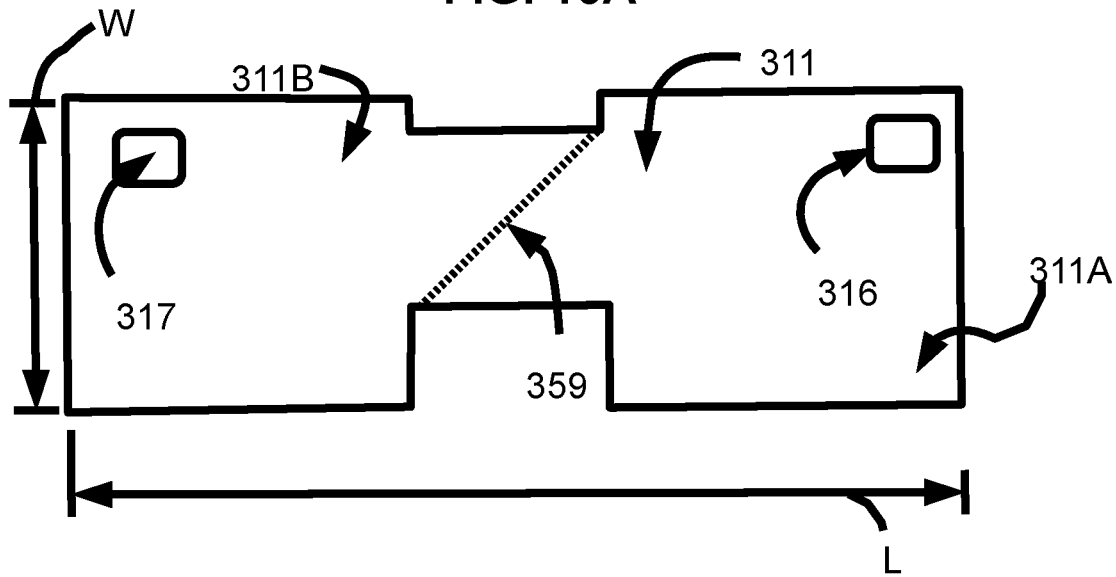
Figure 16C:
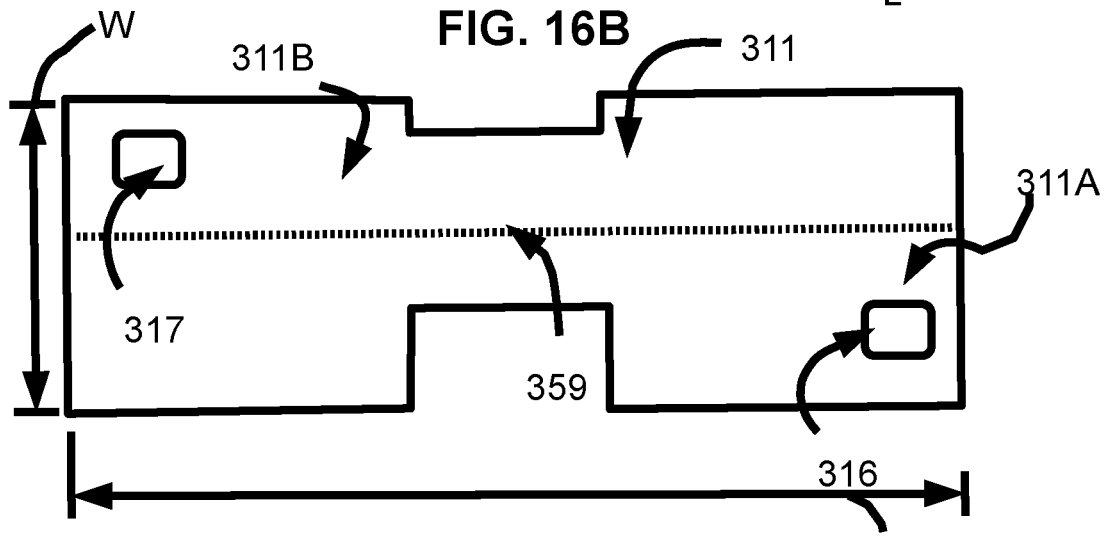

FIGS. 16A-16C illustrate different configurations of the cutline 359. In FIGS. 16A-16C, the blanket 311 forms a first section 311A and a second section 311B. Numbering of the blanket 311 components may correspond to blanket 211 in FIGS. 12-15. The first section 311A can have an inlet 316 and the second section 311B can have an inlet 317. The blanket has a longitudinal dimension L and a width dimension W. The cutline 359 can separate the first section 311A from the second section 311B.

In FIG. 16A, the cutline 359 has at least one curved portion. The cutline 359 is also shown with at least one linear portion that is substantially parallel to the width dimension defined by width W. The cutline 359 is also shown substantially perpendicular to the longitudinal dimension L. When separated into a first section 311A and second section 311B, part of the curved portion can be sealed asymmetrically which can enhance the configurable nature of the cutline 359.

In FIG. 16B, the cutline 359 is linear and shown oriented askew to the longitudinal dimension L. As used herein, askew means that a linear cutline 359 forms an angle from 1 to 89 degrees with the longitudinal dimension L. As shown in FIG. 16B, the angle is approximately 45 degrees.

In FIG. 16C, the cutline 359 is linear and shown parallel to the longitudinal dimension L. The inlet 316 can be disposed lower relative to FIGS. 16A-B in order for the first portion 311A to have an air inlet that is separate from an air inlet of the second portion 311B. The configuration in FIG. 16C may be advantageous when a longer section is desired. However, a longer bonding mechanism disposed longitudinally may be beneficial.

Figure 16D:
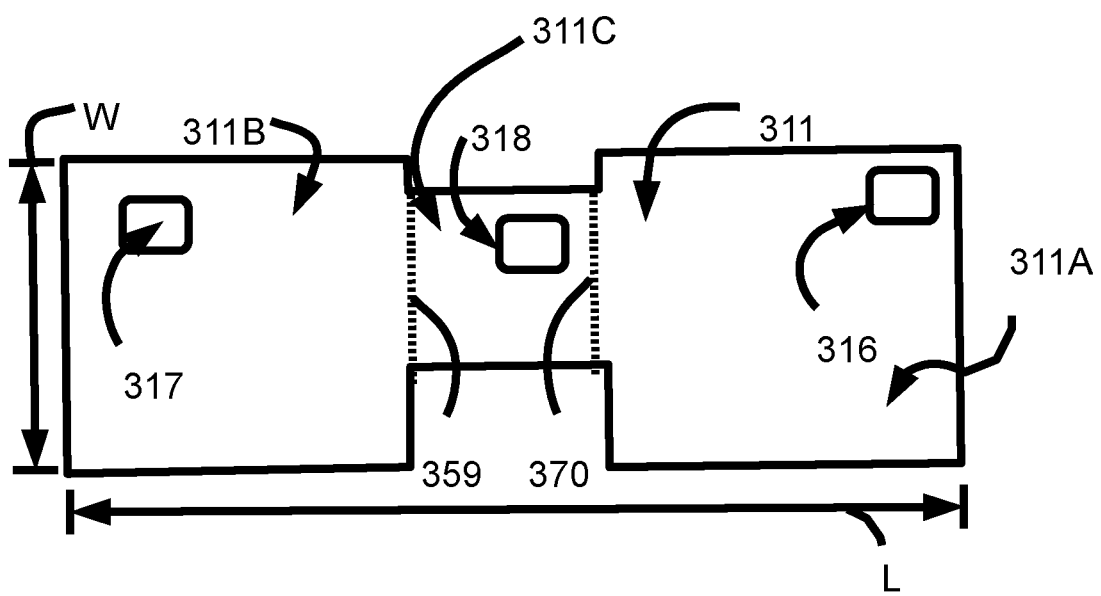

In FIG. 16D, the blanket 311 comprises a first cutline 359 and a second cutline 370. The first cutline 359 can establish a boundary for the second portion 311B. The second cutline 360 can establish a boundary for the first portion 311A. The first portion 311B and the first portion 311A can seal using a bonding mechanism. A third portion 311C with an inlet 318 can form from the tearing of the first cutline 359 and the second cutline 370. Additional bonding mechanisms can allow the third portion 311C to function independently from the first portion 311A and second portion 311B. In at least one embodiment, one cutline (e.g., 370) may be untorn which can allow the use of two portions (311A and 311C).

Figure 17A:
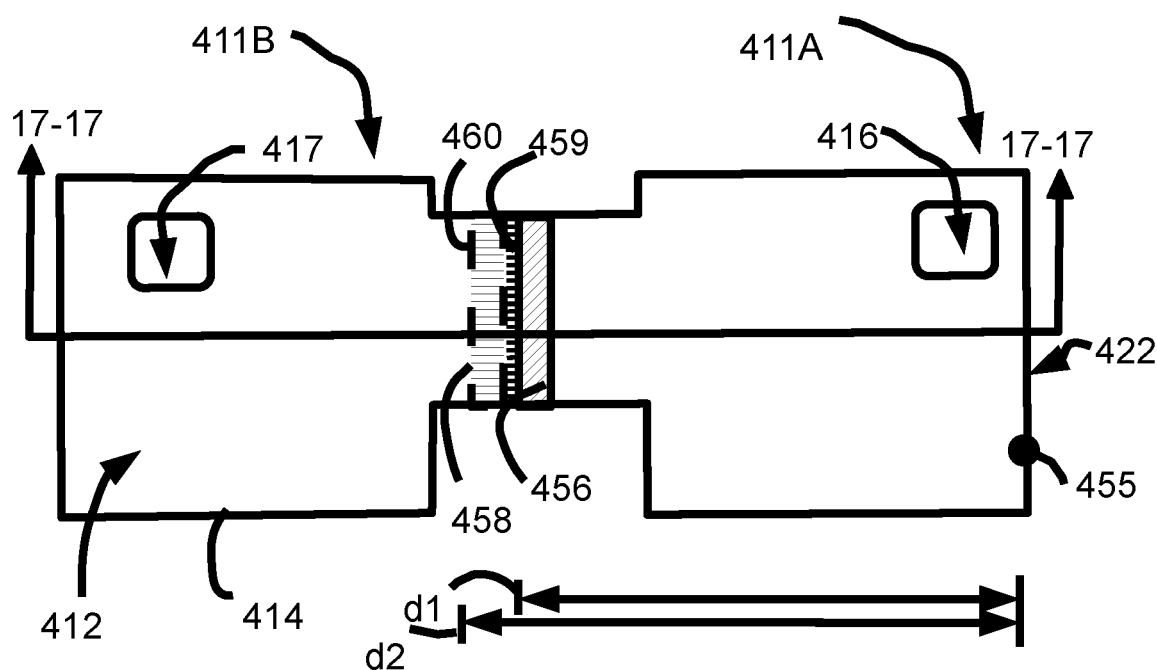
FIG. 17A illustrates a top elevational view of another embodiment of a warming blanket in accordance with one or more example implementations and techniques described in this disclosure.
Figure 17B:
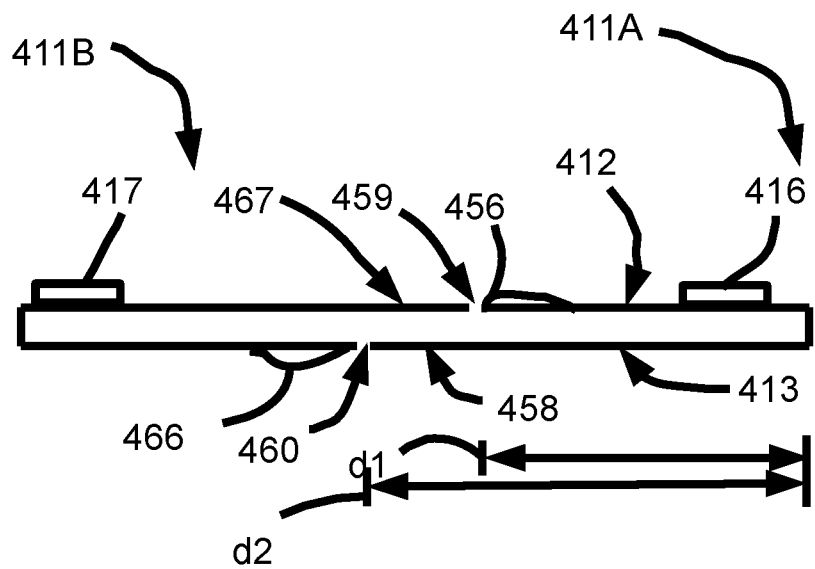
FIG. 17B illustrates a side cross-sectional view of the warming blanket of FIG. 17A taken along lines 17-17 in accordance with one or more example implementations and techniques described in this disclosure.

In FIGS. 17A-B, the bonding mechanism of the blanket 411 can be a flap (e.g., flap 456). FIGS. 17A-17B illustrate a blanket 411 having two portions, 411A and 411B that are attached. The blanket 411 can be constructed similarly to the blanket 211 except that the bonding mechanism is a flap. The numbering of components can correspond to the number of blanket 211.

The blanket 411 can have two layers a first layer 413 and a second layer 412 bonded at least along the periphery 414. The blanket 411 can have an end 422. The first layer 413 has cutline 460 and the second layer has cutline 459. The cutlines 459 and 460 are weakened portions of the layers 413 and 412 respectively and form a divide between the first section 411A and the second section 411B. The second layer 412 can also have a plurality of inlets (e.g., 417, 416) (which are shown as not receiving an air source).

Along the periphery 414 and at end 422, a point 455 can be established. The cutline 459 is positioned at a distance d1 from point 455. The cutline 460 is positioned at a distance d2 from point 455. In at least one embodiment, the distance d1 is different from distance d2. In other embodiments, the distance d1 is the same as distance d2.

In at least one embodiment, the bonding mechanism is a flap and is disposed on a layer. For example, flap 466 is disposed on the first layer 413 and flap 456 is disposed on the second layer 412 The flap can a folded-over portion of the material of the layer. For example, the second layer 412 further comprises a flap 456 that is folded opposite the cutline 459 and folded over an outer surface of the second layer 412 and bonded along the periphery 414. The first layer 413 comprises a flap 466 that is folded opposite the cutline 460 and folded over an outer surface of the first layer 413 and bonded along the periphery.

Also present may be a loose flap formed from a layer. For example, flap 458 can be formed from layer 413 and flap 467 can be formed from layer 412. A flap (e.g., flap 458) can be established by the cutline 460, the periphery 414, and the cutline 459. For example, the flap 458 can have a dimension equal to the difference between d2 and d1.

Each section can have at least one flap and an inlet 416. For example, section 411B can have a flap 467 and flap 466. Sections 411A and 411B can be created by applying force to the cutlines 459 and 460 and removing the seals between the cutlines 459 and 460 along the periphery 414 at the dimension established by d2-d1.

Figure 18A:
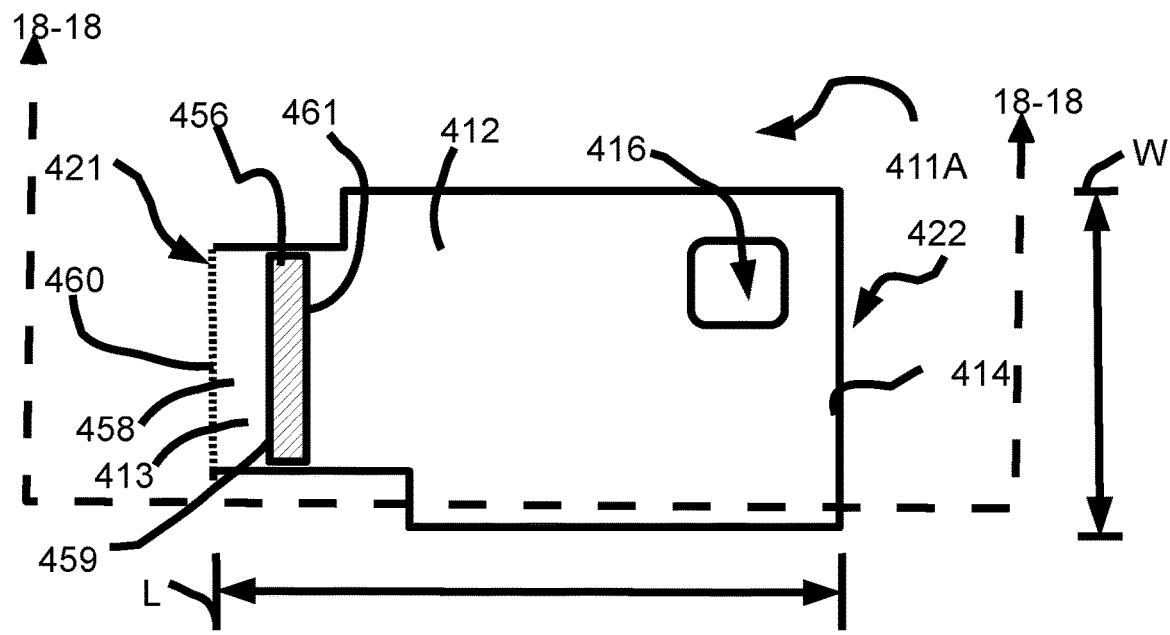
FIG. 18A illustrates one section of the warming blanket of FIGS. 17A-17B in accordance with one or more example implementations and techniques described in this disclosure.
Figure 18B:
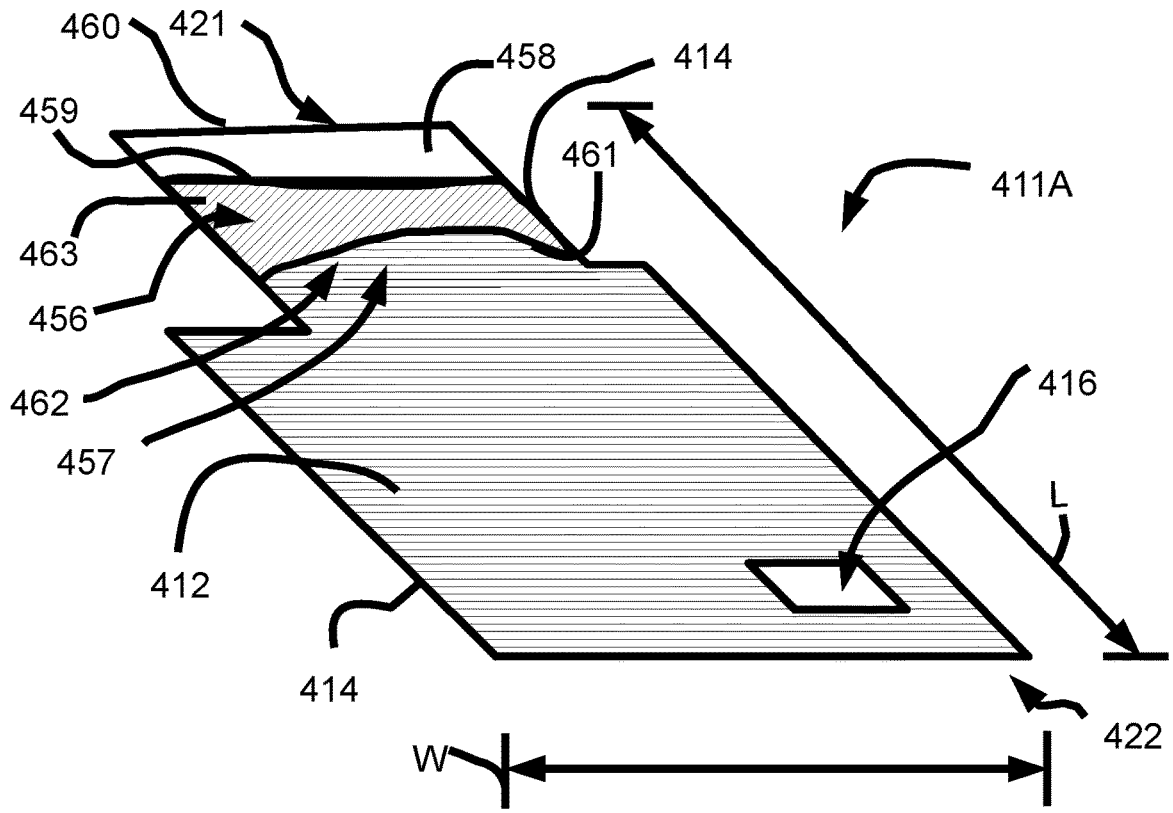
FIG. 18B illustrates a side cross-sectional view of the warming blanket of FIG. 18A taken along lines 18-18 in accordance with one or more example implementations and techniques described in this disclosure.

FIGS. 18A-18B illustrate an enhanced view of portion 411A. Portion 411B may be constructed similarly. The section 411A can comprise at least two layers, the first layer 413 and the second layer 412. The first layer 413 can be bound to the second layer 412 along a periphery 414 and/or various heat seals (not shown) within the periphery 414. The first layer 413 and the second layer 412 can be separated (i.e., unbonded) at the end 421.

The end 421 can have an edge formed from cutline 460 and cutline 459 The section 411A can have a flap 458, and flap 456 positioned at least proximate or adjacent to the end 421. Flap 458 can be formed by the layer 413 and be unattached. The flap 456 can be the same length as flap 458 and can be folded toward end 422 and heat sealed to the periphery 414.

The section 411A can have a width dimension W along end 422. The section 411A can also have a longitudinal dimension L. Opposite end 422 are cutlines 459 and 460. Cutline 460 exists on the first layer 413 while the second cutline 459 exists on the second layer 412. In at least one embodiment, the cutline 459 can form an edge of the flap 456.

The flap 456 can be sealed along the periphery 414 and be bordered by the cutline 459 and have an edge 461. The flap 456 can be formed from the layer 412 and folded over adjacent to or at the cutline 460. In at least one embodiment, the flap 456 is formed from a separate layer that is distinct from layer 412 and sealed with layer 412 at the cutline 460. The flap 456 can be arranged to form a pocket 457 therein. In at least one embodiment, the pocket 457 is formed from the inner surface 462 and the outer surface of layer 412 and the seals of the periphery 414. In at least one embodiment, the outer surface 463 of the flap 456 (generally coplanar with the outer surface of layer 412) can be the same as the inner surface of layer 412.

Figure 19A:
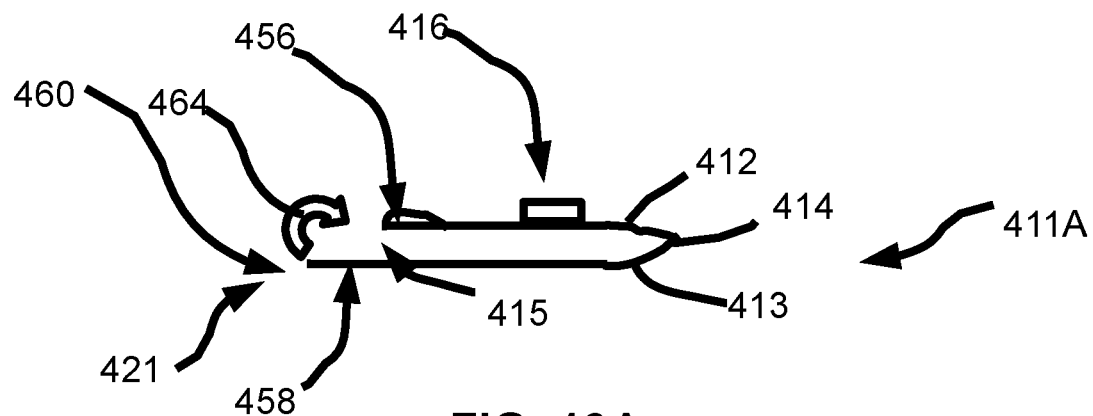
FIGS. 19A-19C illustrates one section of the warming blanket of FIGS. 16A-16B being sealed in accordance with one or more example implementations and techniques described in this disclosure.
Figure 19B:
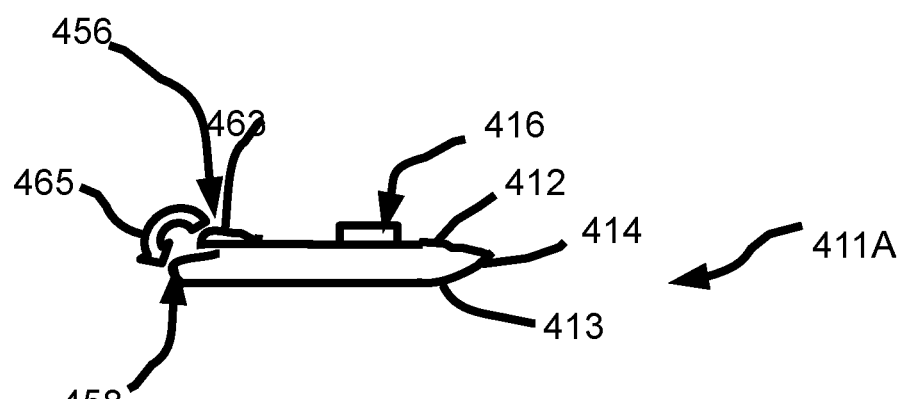
Figure 19C:
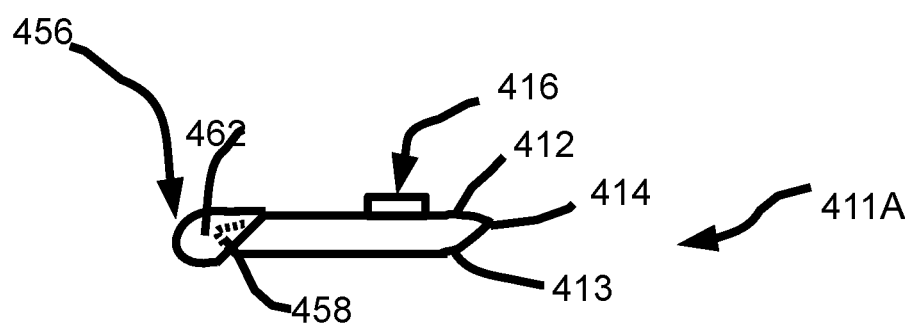

FIGS. 19A-19C illustrate the folding of the flap 456 of the blanket portion 411A. The components of portion 411A are identical to the components described in FIGS. 18A-18B.

In FIG. 19A, the flap 458 at the cutline 460 is folded into a passageway 415 formed between the first layer 413 and the second layer 412. The arrow 464 indicates the direction of movement of the cutline 460. In at least one embodiment, the cutline 459 may contact a portion of the inner surface of layer 412.

In FIG. 19B, the flap 456 is folded such that the surface 463 contacts a portion of the layer 413, specifically a portion of the flap 458, according to the direction arrow 465. The flap 456 can be turned "inside-out" such that the surface 462 (forming a pocket 457 in FIG. 18B) is exposed as shown in FIG. 19C.

When inflated, the flap 456 may have sufficient mechanical strength to retain the air pressure from a source. The air can flow through perforations (not shown) on the layer 413.

Figure 20:
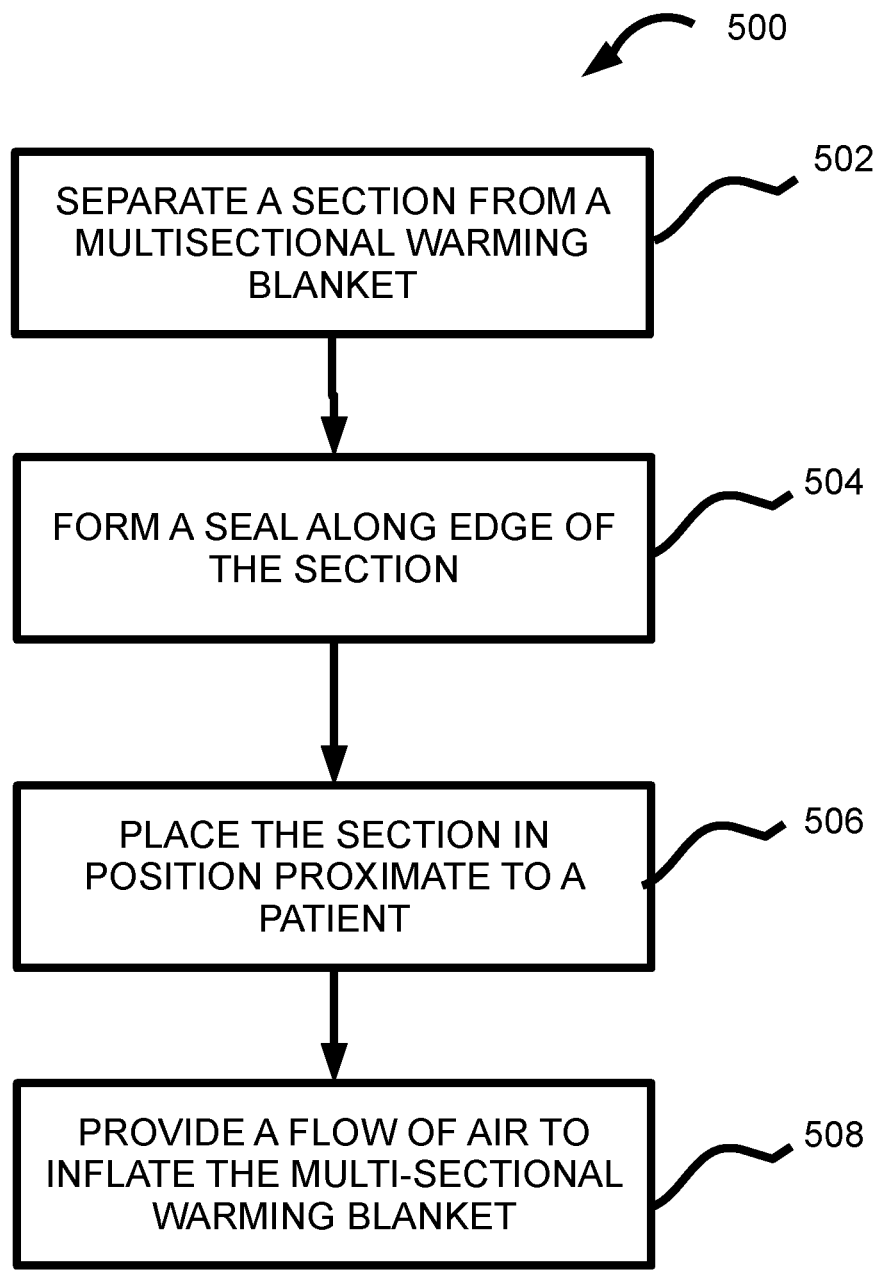
FIG. 20 is a flowchart illustrative of a method in accordance with one or more example implementations and techniques described in this disclosure.

FIG. 20 illustrates a flowchart of a method 500 of using any of the warming blankets described in FIGS. 12-19. As an illustrative example, the blanket of FIGS. 14-15 will be used to describe the method.

The method 500 can begin at block 502 where a section (e.g., 211A or 211B) can be separated from a multi-sectional warming blanket 211. The section can be separated by tearing along cutlines 259 and 260. For example, blanket 211 can have a shear force applied at the cutlines 259 and 260. Once torn, the blanket 211 can exist in independent sections 211A and 211B.

In block 504, a sealed portion 296 can be formed along an edge 282 of at least one of the sections 211A. In some embodiments, the first layer 213 and the second layer 212 can be mechanically linked together (i.e., by adhesive) to one another forming a seal. In at least some embodiments, the mechanical seal can be a fluidic seal and prevent the leakage of pressurized air from a source. In at least one embodiment, a bonding mechanism 290 can be disposed on a portion of the first layer 213A. The bonding mechanism 290 can contact either layer 213A or 212A to form a sealed portion 296. Blocks 506 and 508 can correspond to blocks 206 and 208 in method 200.

The following examples describe one or more aspects of the disclosure.

Example 1

A sectional warming blanket for patient warming, the sectional warming blanket comprising: a structure comprising a first layer of material and a second layer of material, the first layer of material forming a bottom layer of the warming blanket, the bottom layer configured to allow a profusion of air to pass through the bottom layer, and the second layer of material forming an upper layer of the warming blanket, the upper layer coupled to the bottom layer around a periphery of the bottom layer to form an initial shape of the warming blanket and to form an interior space between the first layer of material and the second layer of material comprising a plurality of interconnected air passageways, wherein the passageways are defined by a plurality of seals formed between the upper layer and the bottom layer within the area defined by the periphery; an inlet located on the upper layer or the bottom layer, the inlet comprising an inlet passageway configured to receive a flow of air from a source and to provide the flow of air to the interconnected air passageways; and an opening located on the upper layer or the bottom layer, the opening comprising a removable seal configured to seal an opening passageway coupled to the interconnected air passageways, the removable seal configured to maintain an air seal when in place over the opening passageway.

Example 2

The sectional warming blanket of example 1, therein the inlet is located on the upper layer of the warming blanket and the opening is located on the bottom layer of the warming blanket.

Example 3

The sectional warming blanket of any of examples 1 or 2, wherein the opening is configured to receive a coupling device comprising a first end, a second end, and a hollow shaft coupling the first end and the second end, the first end configured to be received in the opening, the second end configured to be receive in an inlet of the additional sectional warming blanket, the hollow shaft providing an air passageway coupling the sectional warming blanket and the additional sectional warming blanket.

Example 4

The sectional warming blanket of any of examples 1-3, wherein the opening further comprises an adhesive that is configured to affix the opening to an inlet of the additional warming blanket when the adhesive is brought into contact with a portion of the inlet of the additional warming blanket.

Example 5

The sectional warming blanket of any of examples 1-4, wherein the adhesive of provided on a carrier having a first carrier side and a second carrier side, the first carrier side facing the opening and bonding the carrier to the opening, and the second carrier side providing a surface where the adhesive is located.

Example 6

The sectional blanket of any of examples 1-5, wherein an inlet is configured to receive the flow of air by a direct coupling between the inlet and the source generating and providing the flow of air.

Example 7

The sectional blanket of any of examples 1-6, wherein an inlet is configured to be coupled to an opening of the additional sectional warming blanket, and to receive the flow of air from the additional sectional warming blanket as the source of the flow of air.

Example 8

The sectional warming blanket of example 7, wherein the inlet is configured to receive a coupling device comprising a first end, a second end, and a hollow shaft coupling the first end and the second end, the first end configured to be received in the inlet, and the second end configured to be receive in the opening of the additional sectional warming blanket, the hollow shaft providing an air passageway coupling the sectional warming blanket and the additional sectional warming blanket.

Example 9

The sectional warming blanket of example 7, wherein the inlet is configured to be coupled to the opening of the additional warming blankets when an adhesive located on the opening of the additional sectional warming blanket is brought into contact with a portion of the inlet.

Example 10

The sectional warming blanket of example 9, wherein the adhesive located on the opening of the additional sectional warming blanket is provided on a carrier having a first carrier side and a second carrier side, the first carrier side facing the opening and bonding the carrier to the opening, and the second carrier side providing a surface where the adhesive is located.

Example 11

A multi-sectional warming blanket system, the system comprising a plurality of sectional warming blankets coupled together through one or more air flow couplings and arranged into a predetermined arrangement, the predetermined arrangement specific to a designated patient position in patient treatment procedure; and a source of a flow of air coupled to at least one of the plurality of sectional warming blankets, the source configured to deliver a flow of air to the multi-sectional warming blanket at a rate of flow adequate to inflate each of the plurality of sectional warming blankets; wherein each of the sectional warming blankets comprises a structure comprising a first layer of material and a second layer of material, the first layer of material forming a bottom layer of the warming blanket, the bottom layer configured to allow a profusion of air to pass through the bottom layer, and the second layer of material forming an upper layer of the warming blanket, the upper layer coupled to the bottom layer around a periphery of the bottom layer to form an initial shape of the warming blanket and to form an interior space between the first layer of material and the second layer of material comprising a plurality of interconnected air passageways, wherein the passageways are defined by a plurality of seals formed between the upper layer and the bottom layer within the area defined by the periphery, and an inlet located on the upper layer or the bottom layer, the inlet comprising an inlet passageway configured to receive a flow of air from a source and to provide the flow of air to the interconnected air passageways; and an opening located on the upper layer or the bottom layer, the opening comprising a removable seal configured to seal an opening passageway coupled to the interconnected air passageways, the removable seal configured to maintain an air seal when in place over the opening passageway.

Example 12

The system of example 11, wherein the plurality of sectional warming blankets are configured to allow direct coupling of the opening of a first sectional warming blanket of the plurality of sectional warming blankets to an inlet of a second sectional warming blanket of the plurality of sectional warming blankets.

Example 13

The system of any of examples 11 or 12, wherein at least one of the plurality of sectional blankets is configured to directly couple the inlet of the at least one sectional blanket to a hose coupled to the source, and to receive the flow of air from the source at the inlet.

Example 14

The system of any of examples 11-13, wherein at least one of the plurality of sectional blankets is configured so that the opening of the at least one sectional blanket remains sealed and is not coupled to any other of the plurality of sectional blankets through the opening.

Example 15

The system of any of examples 11-14, wherein the predetermined arrangement is configured to be formed by coupling the plurality of the section warming blankets in the predetermined arrangement prior to inflation of the multi-sectional warming blanket using the flow of air.

Example 16

A method of forming a multi-sectional warming blanket, the method comprising: configuring a plurality of sectional warming blankets into a predetermined arrangement, the predetermined arrangement, the predetermined arrangement specific to a designated patient position in patient treatment procedure; forming an air flow coupling between at least two of the plurality of sectional warming blankets to form a multi-sectional warming blanket; and providing a flow of air to at least one of the plurality of sectional warming blankets to inflate each of the sectional warming blankets included in the multi-sectional warming blanket.

Example 17

The method of example 16, further comprising: placing the multi-sectional warming blanket in a position proximate to a patient prior to inflating the multi-sectional warming blanket.

Example 18

The method of any of examples 16-17, wherein configuring the plurality of sectional warming blankets in the predetermined arrangements includes having a first longitudinal axis a first one of the plurality of sectional warming blankets aligned with a second longitudinal axis of a second one of the plurality of sectional warming blankets.

Example 19

The method of any of examples 16-18, wherein configuring the plurality of sectional warming blankets in the predetermined arrangements includes having a first longitudinal axis of a first one of the plurality of sectional warming blankets aligned at an angle with a second longitudinal axis of a second one of the plurality of sectional warming blankets.

Example 20

The method of any of examples 16-19, wherein the angle is about 90-degrees.

Example 21

A method comprising: forming a plurality of sectional warming blankets along a length of web material, each of the sectional warming blankets comprising a bottom layer configured to provide a profusion of air through the bottom layer; forming a set of cutlines, each cutline provided across a width dimension of the web material and located between two of the warming blankets along a longitudinal dimension of the web material; and folding the web material including the sectional warming blankets along the set of cutlines form a stack of sectional warming blankets coupled at the cutlines, each of the sectional warming blankets comprising an inlet located on an upper layer couple to the bottom layer, the inlet comprising an inlet passageway configured to receive a flow of air from a source and to provide the flow of air to an interconnected air passageway located between the upper layer and the bottom layer; and each of the sectional warming blankets further comprising an opening located on the bottom layer, the opening comprising a removable seal configured to seal an opening passageway coupled to the interconnected air passageways, the removable seal configured to maintain an air seal when in place over the opening passageway and to be removed to allow the opening to be coupled to an additional sectional warming blanket to form a multi-sectional warming blanket.

Example 22

The method of example 21, wherein the opening is configured to receive a coupling device comprising a first end, a second end, and a hollow shaft coupling the first end and the second end, the first end configured to be received in the opening, the second end configured to be receive in an inlet of the additional sectional warming blanket, the hollow shaft providing an air passageway coupling the sectional warming blanket and the additional sectional warming blanket.

Example 23

The method of any of examples 21 or 22, wherein the opening further comprises an adhesive that is configured to affix the opening to an inlet of the additional warming blanket when the adhesive is brought into contact with a portion of the inlet of the additional warming blanket.

Example 24

A sectional warming blanket for patient warming, the sectional warming blanket comprising:
a structure comprising a first layer of material and a second layer of material,
the first layer of material forming a bottom layer of the warming blanket, the bottom layer configured to allow a profusion of air to pass through the bottom layer, and
the second layer of material forming an upper layer of the warming blanket, the upper layer coupled to the bottom layer around a periphery of the bottom layer to form an initial shape of the warming blanket and to form an interior space between the first layer of material and the second layer of material comprising a plurality of interconnected air passageways, wherein the passageways are defined by a plurality of seals formed between the upper layer and the bottom layer within the area defined by the periphery;
an inlet located on the upper layer or the bottom layer, the inlet comprising an inlet passageway configured to receive a flow of air from a source and to provide the flow of air to the interconnected air passageways; and
wherein at least a portion of the structure has at least one cutline.

Example 24a

The warming blanket of example 24, wherein the at least one cutline is fluidically coupled to the interior space of the structure.

Example 25

The warming blanket of example 24, further comprising a second inlet.

Example 26

The warming blanket of example 25, wherein the structure comprises a first section and a second section, wherein the second inlet is formed within the second section and the first inlet is formed within the first section.

Example 27

The warming blanket of example 26, wherein at least one cutline divides the first section and the second section.

Example 28

The warming blanket of any of examples 24-27, wherein the at least one cutline is located within the periphery.

Example 29

The warming blanket of any of examples 24-28, wherein the at least one cutline has at least one curved portion.

Example 30

The warming blanket of any of examples 24-29, wherein the at least one cutline is linear.

Example 31

The warming blanket of any of examples 24-30, wherein the blanket has a longitudinal dimension and a width dimension, wherein the at least one cutline is oriented askew to the longitudinal dimension.

Example 32

The warming blanket of any of examples 24-31, wherein the at least one cutline forms an angle from 1 degree to 89 degrees with the longitudinal dimension.

Example 33

The warming blanket of any of examples 24-32, wherein the at least one cutline is oriented perpendicular to the longitudinal dimension.

Example 34

The warming blanket of any of examples 24-33, wherein the at least one cutline is oriented parallel to the width dimension.

Example 35

The warming blanket of any of examples 24-34, wherein the first layer has a first cutline formed therewith.

Example 36

The warming blanket of any of examples 24-35, wherein the second layer has a second cutline formed therewith.

Example 37

The warming blanket of any of examples 24-36, wherein the first cutline is positioned at a first distance from a point on the width dimension.

Example 38

The warming blanket of any of examples 24-37, wherein the second cutline is positioned at a second distance from the point Example 39

The warming blanket of example 38, wherein the second distance is different from the first distance.

Example 40

The warming blanket of example 38, wherein the second distance is equal to the first distance.

Example 41

The warming blanket of example 38, wherein the second distance is greater than the first distance.

Example 42

The warming blanket of any of examples 24-41, further comprising a bonding mechanism disposed on the a portion of the structure.

Example 43

The warming blanket of any of examples 24-42, wherein a first bonding mechanism is disposed on the first layer.

Example 44

The warming blanket of any of examples 24-43, wherein a second bonding mechanism is disposed on the second layer.

Example 45

The warming blanket of any of examples 42-44, wherein the bonding mechanism is a flap.

Example 46

The warming blanket of any of examples 42-45, wherein the first layer further comprises a first flap that is folded opposite the first cutline over an outer surface of the first layer and bonded along the periphery.

Example 47

The warming blanket of any of examples 42-46, wherein the second layer further comprises a second flap that is folded opposite the second cutline and folded over an outer surface of the second layer and bonded along the periphery.

Example 48

The warming blanket of any of examples 42-47, wherein the bonding mechanism is configured to attach the first layer and the second layer.

Example 48a

The warming blanket of any of examples 42-47, wherein the bonding mechanism is configured to attach the first layer and the second layer sufficient to form a seal.

Example 49

The warming blanket of any of examples 42-48, wherein the bonding mechanism is disposed adjacent to the cutline.

Example 50

The warming blanket of example 48 or 49, wherein the attachment between the first layer and the second layer is configured to resist air flow leaving the blanket such that the blanket remains inflated.

Example 51

The warming blanket of any one of examples 42-44, wherein the bonding mechanism is an adhesive.

Example 52

The warming blanket of example 51, further comprising a release liner disposed on the adhesive.

Example 53

The warming blanket of any of examples 42-44, wherein the bonding mechanism is a mechanical fastener with one portion disposed on the first layer and the second portion disposed on the outside surface of the second layer.

Example 54

The warming blanket of any of examples 24-53, comprising:
a first section having a border formed from a portion of the periphery and a first end,
wherein the first end is formed from a portion of at least one cutline,
wherein the first end comprises an opening formed from a first edge portion of the first layer and a second edge portion of the second layer.

Example 55

The warming blanket of example 54, further comprising:
a second section having a border formed from a portion of the periphery and a first end,
wherein the second end is formed from a portion of at least one cutline,
wherein the second end comprises an opening formed from a first edge portion of the first layer and a second edge portion of the second layer.

Example 56

The warming blanket of example 54 or 55, wherein the at least one cutline separates the first section from the second section within a layer.

Example 57

The warming blanket of example 54 or 55, wherein the at least one cutline releasably attaches the first section with the second section within a layer.

Example 58

The warming blanket of any of examples 24-56, wherein a cutline is a line of weakness in a layer.

Example 59

The warming blanket of any of examples 24-57, wherein the at least one cutline is a printed pattern disposed on a layer.

Example 60

A method, comprising:
separating a first section from the warming blanket of any of examples 24-58;
forming a seal along the edge portion of the first section;
placing the first section in a position proximate to a patient; and
providing a flow of air into the inlet of the warming blanket.

Example 61

The method of example 60, wherein the separating the first section comprises:
securing the first section and the second section;
tearing the first section away from the second section along the cutline.

Example 62

The method of example 60 or 61, wherein forming a seal along the edge portion of the first section comprises:
attaching a portion of a layer to a bonding mechanism sufficient to create a seal.

Example 63

The method of example 62, further comprising:
bonding the first layer to the second layer along the cutline.

Example 64 the system of any of examples 1-15, or the method of any of examples 16-23, wherein the opening is formed from a portion of the upper layer therein.

Example 65 the system of any of examples 1-15, or the method of any of examples 16-23, wherein the opening is formed from the upper layer therein.

Example 66

The system of any of examples 1-15, or the method of any of examples 16-23, wherein the opening is formed from a portion of the bottom layer therein.

Example 67

The warming blanket of any of examples 24-59, or the method of any of examples 60-64, wherein the interconnected air passageway is formed from a portion of the first layer or the second layer therein.

Various examples of techniques associated with multi-sectional patient warming blankets have been described in this disclosure. These and other examples are within the scope of the following claims.

What is claimed is:

1. A system of patient warming, comprising:
a first sectional warming blanket and a second sectional warming blanket, each comprising:
a structure comprising a first layer of material and a second layer of material,
the first layer of material forming a bottom layer of the first or second sectional warming blanket, the bottom layer configured to allow a profusion of air to pass through the bottom layer, and
the second layer of material forming an upper layer of the first or second sectional warming blanket, the upper layer coupled to the bottom layer around a periphery of the bottom layer to form an initial shape of the first or second sectional warming blanket and to form an interior space between the first layer of material and the second layer of material comprising a plurality of interconnected air passageways, wherein the passageways are defined by a plurality of seals formed between the upper layer and the bottom layer within an area defined by the periphery;
an inlet located on the upper layer or the bottom layer, the inlet comprising an inlet passageway configured to receive a flow of air from a source and to provide the flow of air to the interconnected air passageways; and
an opening located on the upper layer or the bottom layer, the opening comprising a removable seal configured to seal an opening passageway coupled to the interconnected air passageways, the removable seal configured to maintain an air seal when in place over the opening passageway, wherein the opening opposes the inlet;
wherein an inlet from the first sectional warming blanket is configured to be coupled to an opening of the second sectional warming blanket, and to receive the flow of air from the second sectional warming blanket as the source of the flow of air.

2. The system of claim 1, wherein the inlet of the first or second sectional warming blanket is located on the upper layer of the first or second sectional warming blanket and the opening of the first or second sectional warming blanket is located on the bottom layer.

3. The system of claim 1, wherein the upper layer of the second sectional warming blanket contacts the bottom layer of the first sectional warming blanket.

4. The system of claim 1, wherein the bottom layer of the first sectional warming blanket contacts the bottom layer of the second sectional warming blanket.

5. The system of claim 1, further comprising:
a coupling device comprising a first end, a second end, and a hollow shaft coupling the first end and the second end, the hollow shaft providing an air passageway coupling the first sectional warming blanket and the second sectional warming blanket.

6. The system of claim 5, wherein the first end configured to be received in the opening of the first sectional warming blanket, the second end configured to be received in the inlet of the second sectional warming blanket.

7. The system of claim 5, wherein the first end configured to be received in the inlet of the first sectional warming blanket, the second end configured to be received in the opening of the second sectional warming blanket.

8. The system of claim 1, wherein the opening of the first sectional warming blanket further comprises an adhesive that is configured to affix the opening of the first sectional warming blanket directly to the inlet of the second sectional warming blanket when the adhesive is brought into contact with a portion of the inlet of the second sectional warming blanket.

9. The system of claim 8, wherein the adhesive is provided on a carrier having a first carrier side and a second carrier side, the first carrier side facing the opening of the first sectional warming blanket and bonding the carrier to the opening of the first sectional warming blanket, and the second carrier side providing a surface where the adhesive is located.

10. The system of claim 1, wherein the inlet of the first sectional warming blanket is configured to receive the flow of air by a direct coupling between the inlet of the first sectional warming blanket and the source generating and providing the flow of air.

11. The system of claim 1, wherein the inlet of the first sectional warming blanket is configured to be coupled to an opening of the second sectional warming blanket when an adhesive located on the opening of the second sectional warming blanket is brought into contact with a portion of the inlet.

12. The system of claim 11, wherein the adhesive located on the opening of the second sectional warming blanket is provided on a carrier having a first carrier side and a second carrier side, the first carrier side facing the opening of the second sectional warming blanket and bonding the carrier to the opening, and the second carrier side providing a surface where the adhesive is located.

13. The system of claim 1, wherein the first sectional warming blanket and the second warming blanket are configurable to have a non-linear arrangement.

* * * * *